US010517882B2

(12) United States Patent
Tamarkin et al.

(10) Patent No.: US 10,517,882 B2
(45) Date of Patent: *Dec. 31, 2019

(54) METHOD FOR HEALING OF AN INFECTED ACNE LESION WITHOUT SCARRING

(71) Applicant: Foamix Pharmaceuticals Ltd., Rehovot (IL)

(72) Inventors: Dov Tamarkin, Maccabim (IL); Elana Gazal, Rehovot (IL); Rita Keynan, Rehovot (IL); Meir Eini, Ness Ziona (IL); David Schuz, Gimzu (IL)

(73) Assignee: Foamix Pharmaceuticals Ltd., Rehovot (IL)

( * ) Notice: Subject to any disclaimer, the term of this patent is extended or adjusted under 35 U.S.C. 154(b) by 257 days.

This patent is subject to a terminal disclaimer.

(21) Appl. No.: 15/816,850

(22) Filed: Nov. 17, 2017

(65) Prior Publication Data
US 2018/0147218 A1 May 31, 2018

Related U.S. Application Data

(63) Continuation of application No. 13/831,396, filed on Mar. 14, 2013, now Pat. No. 9,849,142, which is a continuation-in-part of application No. 13/499,475, filed as application No. PCT/IB2010/002617 on Oct. 1, 2010, now Pat. No. 8,871,184, said application No. 13/831,396 is a continuation-in-part of application No. 13/499,501, filed as application No. PCT/IB2010/002612 on Oct. 1, 2010, now Pat. No. 8,945,516, said application No. 13/831,396 is a continuation-in-part of application No. 13/499,727, filed as application No. PCT/IB2011/001374 on May 4, 2011, said application No. 13/831,396 is a continuation-in-part of application No. 13/499,709, filed on Sep. 10, 2012, now Pat. No. 10,029,013, and a continuation-in-part of application No. 13/100,724, filed on May 4, 2011, now Pat. No. 8,618,081, which is a continuation-in-part of application No. PCT/IB2010/002617, filed on Oct. 1, 2010, said application No. 13/831,396 is a continuation-in-part of application No. PCT/IB2010/002612, filed on Oct. 1, 2010, said application No. 13/100,724 is a continuation-in-part of application No. PCT/IB2010/002613, filed on Oct. 1, 2010, said application No. 13/499,709 is a continuation-in-part of application No. PCT/IB2010/002613, filed on Oct. 1, 2010.

(60) Provisional application No. 61/780,074, filed on Mar. 13, 2013, provisional application No. 61/779,953, filed on Mar. 13, 2013, provisional application No. 61/748,603, filed on Jan. 3, 2013, provisional application No. 61/611,232, filed on Mar. 15, 2012, provisional application No. 61/388,884, filed on Oct. 1, 2010, provisional application No. 61/385,385, filed on Sep. 22, 2010, provisional application No. 61/380,568, filed on Sep. 7, 2010, provisional (Continued)

(51) Int. Cl.
| A61K 31/65 | (2006.01) |
| A61K 9/00 | (2006.01) |
| A61K 47/10 | (2017.01) |
| A61K 47/12 | (2006.01) |
| A61K 9/12 | (2006.01) |
| A61K 47/44 | (2017.01) |
| A61P 17/10 | (2006.01) |
| A61K 47/06 | (2006.01) |
| A61K 47/24 | (2006.01) |
| A61K 9/06 | (2006.01) |

(52) U.S. Cl.
CPC ............ *A61K 31/65* (2013.01); *A61K 9/0014* (2013.01); *A61K 9/06* (2013.01); *A61K 9/122* (2013.01); *A61K 47/06* (2013.01); *A61K 47/10* (2013.01); *A61K 47/12* (2013.01); *A61K 47/24* (2013.01); *A61K 47/44* (2013.01)

(58) Field of Classification Search
None
See application file for complete search history.

(56) References Cited

U.S. PATENT DOCUMENTS 1,159,250 A   11/1915   Moulton
1,666,684 A   4/1928   Carstens (Continued)

FOREIGN PATENT DOCUMENTS

AU   198780257 A   9/1986
AU   782515 B2   12/2005

(Continued)

OTHER PUBLICATIONS

"Everything but the Olive." The Olive Oil Source 1998-2016 [online]. Retrieved from the Internet: http://www.oliveoilsource.com/pageA chemical-characteristics.

(Continued)

*Primary Examiner* — Bethany P Barham
*Assistant Examiner* — Peter Anthopolos
(74) *Attorney, Agent, or Firm* — Finnegan, Henderson, Farabow, Garrett & Dunner, LLP

(57) ABSTRACT

Methods of treatment and dosage regimes using hydrophobic gel or foam compositions comprising a tetracycline antibiotic for accelerating the return of skin integrity and or in treating or alleviating a disorder including impetigo, acne, rosacea, a skin disease caused by a bacteria or a tetracycline antibiotic responsive disease, wherein the foam composition or gel is administered topically to a target area on a subject having the disorder and wherein the target area comprises an area of skin, or mucosa or an eye.

8 Claims, 11 Drawing Sheets

Related U.S. Application Data application No. 61/349,911, filed on May 31, 2010, provisional application No. 61/331,126, filed on May 4, 2010, provisional application No. 61/322,148, filed on Apr. 8, 2010, provisional application No. 61/248,144, filed on Oct. 2, 2009.

(56) References Cited

U.S. PATENT DOCUMENTS

| | | |
|---|---|---|
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,334,147 A | 8/1967 | Brunelle et al. |
| 3,342,845 A | 9/1967 | Sayigh et al. |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,383,280 A | 5/1968 | Kuehns |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,824,303 A | 7/1974 | Lanzet et al. |
| 3,841,525 A | 10/1974 | Siegel |
| 3,849,569 A | 11/1974 | Mead |
| 3,849,580 A | 11/1974 | Weinstein et al. |
| 3,865,275 A | 2/1975 | De Nunzio |
| 3,866,800 A | 2/1975 | Schmitt |
| 3,878,118 A | 4/1975 | Watson |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,912,667 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,953,591 A | 4/1976 | Snyder |
| 3,959,160 A | 5/1976 | Horsier et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,052,513 A | 10/1977 | Kaplan |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,278,206 A | 7/1981 | Prussin |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,338,211 A | 7/1982 | Stiros |
| 4,352,808 A | 10/1982 | Rane et al. |
| 4,363,806 A | 12/1982 | Bergstrom et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,607,101 A | 8/1986 | Bernstein |
| 4,612,193 A | 9/1986 | Gordon et al. |
| 4,627,973 A | 12/1986 | Moran et al. |
| 4,628,063 A | 12/1986 | Haines et al. |
| 4,661,340 A | 4/1987 | Nagy et al. |
| 4,661,524 A | 4/1987 | Thomson et al. |
| 4,672,078 A | 6/1987 | Sakai et al. |
| 4,673,569 A | 6/1987 | Shernov et al. |

(56) References Cited

U.S. PATENT DOCUMENTS

| | | |
|---|---|---|
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,849,211 A | 7/1989 | Schrauzer |
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,876,083 A | 10/1989 | Grollier et al. |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mon et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,530 A | 6/1993 | Janchitraponvej et al. |
| 5,221,534 A | 6/1993 | DesLauriers et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,305 A | 2/1995 | Repinec et al. |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |

(56) References Cited

U.S. PATENT DOCUMENTS

| | | |
|---|---|---|
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,705,472 A | 1/1998 | Hayes et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,854,246 A | 12/1998 | Francois et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,939,376 A | 8/1999 | Durbut et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,017,912 A | 1/2000 | Bussell |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,060,041 A | 5/2000 | Candau et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,310 A | 7/2000 | Heinkel |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,133,327 A | 10/2000 | Kimura et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,662 B1 | 1/2001 | Lanzendorfer et al. |
| 6,180,669 B1 | 1/2001 | Tamarkin |
| 6,183,762 B1 | 2/2001 | Deckers et al. |

(56) References Cited

U.S. PATENT DOCUMENTS

| | | |
|---|---|---|
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,241,971 B1 | 6/2001 | Fox et al. |
| 6,251,369 B1 | 6/2001 | Stoltz |
| 6,258,374 B1 | 7/2001 | Friess et al. |
| 6,261,544 B1 | 7/2001 | Coury et al. |
| 6,264,964 B1 | 7/2001 | Mohammadi |
| 6,270,781 B1 | 8/2001 | Gehlsen |
| 6,271,295 B1 | 8/2001 | Powell et al. |
| 6,274,150 B1 | 8/2001 | Simonnet et al. |
| 6,283,336 B1 | 9/2001 | Dwyer et al. |
| 6,284,802 B1 | 9/2001 | Bissett et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,352,727 B1 | 3/2002 | Takahashi |
| 6,355,230 B2 | 3/2002 | Gers-Barlag et al. |
| 6,358,541 B1 | 3/2002 | Goodman |
| 6,358,924 B1 | 3/2002 | Hoffmann |
| 6,364,854 B1 | 4/2002 | Ferrer et al. |
| 6,372,234 B1 | 4/2002 | Deckers et al. |
| 6,375,936 B1 | 4/2002 | Allard et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,423,329 B1 | 7/2002 | Sine et al. |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,433,068 B1 | 8/2002 | Morrison et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,060 B1 | 11/2002 | Jones et al. |
| 6,479,532 B1 | 11/2002 | Kamimura et al. |
| 6,482,810 B1 | 11/2002 | Brem et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,551,604 B1 | 4/2003 | Beck et al. |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,607,716 B1 | 8/2003 | Smith et al. |
| 6,610,315 B2 | 8/2003 | Scholz et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,706,290 B1 | 3/2004 | Kajander et al. |
| 6,709,663 B2 | 3/2004 | Espinoza |
| 6,723,309 B1 | 4/2004 | Deane |
| 6,730,288 B1 | 5/2004 | Abram |
| 6,736,860 B2 | 5/2004 | Patel et al. |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,841,547 B2 | 1/2005 | Brown et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |
| 6,914,057 B1 | 7/2005 | Ryan et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,986,883 B2 | 1/2006 | Pellico |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |

(56) References Cited

U.S. PATENT DOCUMENTS

| | | |
|---|---|---|
| 7,270,828 B2 | 9/2007 | Masuda et al. |
| 7,455,195 B2 | 11/2008 | Meketa |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | Van Der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,842,791 B2 | 11/2010 | Britten et al. |
| 7,960,416 B2 | 6/2011 | Sato et al. |
| 8,114,385 B2 | 2/2012 | Tamarkin et al. |
| 8,119,106 B2 | 2/2012 | Tamarkin et al. |
| 8,119,109 B2 | 2/2012 | Tamarkin et al. |
| 8,119,150 B2 | 2/2012 | Tamarkin et al. |
| 8,158,109 B2 | 4/2012 | Abram et al. |
| 8,192,749 B2 | 6/2012 | Ashley |
| 8,211,874 B2 | 7/2012 | Theobald et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,374 B2 | 7/2013 | Tamarkin et al. |
| 8,486,375 B2 | 7/2013 | Tamarkin et al. |
| 8,486,376 B2 | 7/2013 | Friedman et al. |
| 8,512,718 B2 | 8/2013 | Eini et al. |
| 8,518,376 B2 | 8/2013 | Tamarkin et al. |
| 8,518,378 B2 | 8/2013 | Tamarkin et al. |
| 8,592,380 B2 | 11/2013 | Trumbore et al. |
| 8,617,100 B2 | 12/2013 | Eini et al. |
| 8,618,081 B2 | 12/2013 | Tamarkin et al. |
| 8,623,330 B2 | 1/2014 | Gurge et al. |
| 8,636,982 B2 | 1/2014 | Tamarkin et al. |
| 8,652,443 B2 | 2/2014 | Varanasi et al. |
| 8,709,385 B2 | 4/2014 | Tamarkin et al. |
| 8,722,021 B2 | 5/2014 | Friedman et al. |
| 8,735,377 B1 | 5/2014 | Sipos |
| 8,741,265 B2 | 6/2014 | Tamarkin et al. |
| 8,778,365 B1 | 7/2014 | Hardas et al. |
| 8,784,780 B2 | 7/2014 | Gurge et al. |
| 8,795,635 B2 | 8/2014 | Tamarkin et al. |
| 8,795,693 B2 | 8/2014 | Tamarkin et al. |
| 8,840,869 B2 | 9/2014 | Friedman et al. |
| 8,846,039 B2 | 9/2014 | Chung et al. |
| 8,865,139 B1 | 10/2014 | Tamarkin et al. |
| 8,871,184 B2 | 10/2014 | Tamarkin et al. |
| 8,895,536 B2 | 11/2014 | Bannister et al. |
| 8,900,553 B2 | 12/2014 | Tamarkin et al. |
| 8,900,554 B2 | 12/2014 | Tamarkin et al. |
| 8,945,516 B2 | 2/2015 | Tamarkin et al. |
| 8,992,896 B2 | 3/2015 | Tamarkin et al. |
| 9,050,253 B2 | 6/2015 | Tamarkin et al. |
| 9,072,667 B2 | 7/2015 | Tamarkin et al. |
| 9,101,662 B2 | 8/2015 | Tamarkin et al. |
| 9,161,916 B2 | 10/2015 | Tamarkin et al. |
| 9,167,813 B2 | 10/2015 | Tamarkin et al. |
| 9,192,558 B2 | 11/2015 | Chen et al. |
| 9,211,259 B2 | 12/2015 | Friedman et al. |
| 9,265,725 B2 | 2/2016 | Tamarkin et al. |
| 9,265,740 B2 | 2/2016 | Johnston et al. |
| 9,320,705 B2 | 4/2016 | Tamarkin et al. |
| 9,439,857 B2 | 9/2016 | Tamarkin et al. |
| 9,474,720 B2 | 10/2016 | Yamamoto |
| 9,492,412 B2 | 11/2016 | Tamarkin et al. |
| 9,539,208 B2 | 1/2017 | Tamarkin et al. |
| 9,539,266 B2 | 1/2017 | Mansouri |
| 9,549,898 B2 | 1/2017 | Tamarkin et al. |
| 9,572,775 B2 | 2/2017 | Tamarkin et al. |
| 9,592,246 B2 | 3/2017 | Salman et al. |
| 9,622,947 B2 | 4/2017 | Tamarkin et al. |
| 9,636,405 B2 | 5/2017 | Tamarkin et al. |
| 9,662,298 B2 | 5/2017 | Tamarkin et al. |
| 9,668,972 B2 | 6/2017 | Tamarkin et al. |
| 9,675,700 B2 | 6/2017 | Tamarkin et al. |
| 9,682,021 B2 | 6/2017 | Tamarkin et al. |
| 9,713,643 B2 | 7/2017 | Friedman et al. |
| 9,795,564 B2 | 10/2017 | Tamarkin et al. |
| 9,849,142 B2 | 12/2017 | Tamarkin et al. |
| 9,884,017 B2 | 2/2018 | Tamarkin et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0033838 A1 | 10/2001 | Farmer |
| 2001/0036450 A1 | 11/2001 | Verite et al. |
| 2001/0054574 A1 | 12/2001 | Navarro |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0031478 A1 | 3/2002 | Keller et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Halswanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0182234 A1 | 12/2002 | Riedel et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0013692 A1 | 1/2003 | Gullans et al. |
| 2003/0017181 A1 | 1/2003 | Rood et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0077301 A1 | 4/2003 | Maibach et al. |
| 2003/0078172 A1 | 4/2003 | Guiramand et al. |
| 2003/0082120 A1 | 5/2003 | Milstein |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0118527 A1 | 6/2003 | Jager et al. |
| 2003/0129259 A1 | 7/2003 | Mahalingam et al. |
| 2003/0130247 A1 | 7/2003 | Gans et al. |
| 2003/0148949 A1 | 8/2003 | Podolsky |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0185861 A1 | 10/2003 | Hon et al. |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215418 A1 | 11/2003 | Asmus et al. |
| 2003/0215472 A1 | 11/2003 | Bonda et al. |
| 2003/0235597 A1 | 12/2003 | Withiam et al. |
| 2004/0002550 A1 | 1/2004 | Mecurio |
| 2004/0018228 A1 | 1/2004 | Fischel) et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |

(56) References Cited

U.S. PATENT DOCUMENTS

| | | |
|---|---|---|
| 2004/0105825 A1 | 6/2004 | Henning |
| 2004/0106688 A1 | 6/2004 | Koike et al. |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0198706 A1 | 10/2004 | Carrara |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0258627 A1 | 12/2004 | Riedel et al. |
| 2004/0258628 A1 | 12/2004 | Riedel et al. |
| 2004/0258643 A1 | 12/2004 | Yaqub et al. |
| 2005/0002976 A1 | 1/2005 | Wu |
| 2005/0013853 A1 | 1/2005 | Gil-Ad et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0075407 A1 | 4/2005 | Tamarkin et al. |
| 2005/0079139 A1 | 4/2005 | Jacques et al. |
| 2005/0079228 A1 | 4/2005 | Jaiswal et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0148552 A1 | 7/2005 | Ryan et al. |
| 2005/0153943 A1 | 7/2005 | Ashley |
| 2005/0164993 A1 | 7/2005 | Ashley |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Meketa |
| 2006/0057168 A1 | 3/2006 | Larm et al. |
| 2006/0099151 A1 | 5/2006 | Neubourg |
| 2006/0108377 A1 | 5/2006 | Glynn et al. |
| 2006/0110415 A1 | 5/2006 | Gupta |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0015739 A1 | 1/2007 | Walker et al. |
| 2007/0017696 A1 | 1/2007 | Lin et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0111956 A1 | 5/2007 | Matsushima et al. |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0141086 A1 | 6/2007 | Ohara et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0166274 A1 | 7/2007 | Mazur et al. |
| 2007/0224143 A1 | 9/2007 | Konis |
| 2007/0237724 A1 | 10/2007 | Abram et al. |
| 2007/0264317 A1 | 11/2007 | Yosha et al. |
| 2007/0271235 A1 | 11/2007 | Frank et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0050317 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |

(56) References Cited

U.S. PATENT DOCUMENTS

| | | |
|---|---|---|
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0311167 A1 | 12/2008 | Oronsky et al. |
| 2008/0317679 A1 | 12/2008 | Tamarkin et al. |
| 2009/0017147 A1 | 1/2009 | Lintner et al. |
| 2009/0053290 A1 | 2/2009 | Sand et al. |
| 2009/0061001 A1 | 3/2009 | Hougaz |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0214628 A1 | 8/2009 | De Rijk |
| 2009/0291917 A1 | 11/2009 | Akama et al. |
| 2010/0111879 A1 | 5/2010 | Tamarkin et al. |
| 2010/0221194 A1 | 9/2010 | Loupenok |
| 2010/0247449 A1 | 9/2010 | Graupe et al. |
| 2010/0286417 A1 | 11/2010 | Mendes et al. |
| 2011/0002969 A1 | 1/2011 | Serraima et al. |
| 2011/0097279 A1 | 4/2011 | Tamarkin et al. |
| 2011/0207765 A1 | 8/2011 | Van Den Bussche et al. |
| 2011/0262542 A1 | 10/2011 | Ashley |
| 2012/0064136 A1 | 3/2012 | Baker, Jr. et al. |
| 2012/0082632 A1 | 4/2012 | Phillips et al. |
| 2012/0087872 A1 | 4/2012 | Tamarkin et al. |
| 2012/0128598 A1 | 5/2012 | Trumbore et al. |
| 2012/0141384 A1 | 6/2012 | Tamarkin |
| 2012/0148503 A1 | 6/2012 | Tamarkin et al. |
| 2012/0156144 A1 | 6/2012 | Tamarkin et al. |
| 2012/0164087 A1 | 6/2012 | Carter |
| 2012/0181201 A1 | 7/2012 | Heggie |
| 2012/0237453 A1 | 9/2012 | Tamarkin et al. |
| 2013/0011342 A1 | 1/2013 | Tamarkin et al. |
| 2013/0053353 A1 | 2/2013 | Tamarkin et al. |
| 2013/0115173 A1 | 5/2013 | Trumbore et al. |
| 2013/0161351 A1 | 6/2013 | Eini et al. |
| 2013/0164225 A1 | 6/2013 | Tamarkin et al. |
| 2013/0189195 A1 | 7/2013 | Tamarkin et al. |
| 2013/0189196 A1 | 7/2013 | Tamarkin et al. |
| 2013/0251644 A1 | 9/2013 | Majhi et al. |
| 2013/0261565 A1 | 10/2013 | Wong et al. |
| 2013/0295022 A1 | 11/2013 | Friedman et al. |
| 2013/0296387 A1 | 11/2013 | Saad |
| 2014/0066524 A1 | 3/2014 | Tamarkin et al. |
| 2014/0086848 A1 | 3/2014 | Tamarkin et al. |
| 2014/0121188 A1 | 5/2014 | Tamarkin et al. |
| 2014/0140937 A1 | 5/2014 | Gurge et al. |
| 2014/0182585 A1 | 7/2014 | Tamarkin et al. |
| 2014/0186269 A1 | 7/2014 | Tamarkin et al. |
| 2014/0221320 A1 | 8/2014 | Joks et al. |
| 2014/0228355 A1 | 8/2014 | Kortagere et al. |
| 2014/0242016 A1 | 8/2014 | Binks et al. |
| 2015/0025060 A1 | 1/2015 | Tamarkin et al. |
| 2015/0098907 A1 | 4/2015 | Tamarkin et al. |
| 2015/0141381 A1 | 5/2015 | Levy et al. |
| 2015/0157586 A1 | 6/2015 | Tamarkin et al. |
| 2015/0164922 A1 | 6/2015 | Tamarkin et al. |
| 2015/0174144 A1 | 6/2015 | Bowser et al. |
| 2015/0196570 A1 | 7/2015 | Tamarkin et al. |
| 2015/0209296 A1 | 7/2015 | Yamamoto |
| 2015/0374625 A1 | 12/2015 | Tamarkin et al. |
| 2016/0101184 A1 | 4/2016 | Tamarkin et al. |
| 2016/0128944 A1 | 5/2016 | Chawrai et al. |
| 2016/0158261 A1 | 6/2016 | Friedman et al. |
| 2016/0213757 A1 | 7/2016 | Edelson et al. |
| 2016/0279152 A1 | 9/2016 | Chen et al. |
| 2016/0287615 A1 | 10/2016 | Chan et al. |
| 2016/0354473 A1 | 12/2016 | Tamarkin et al. |
| 2016/0361252 A1 | 12/2016 | Franke |
| 2016/0361320 A1 | 12/2016 | Zhao et al. |
| 2017/0014517 A1 | 1/2017 | Tamarkin |
| 2017/0049712 A1 | 2/2017 | Bhalani et al. |
| 2017/0119665 A1 | 5/2017 | Tamarkin et al. |
| 2017/0157175 A1 | 6/2017 | Tamarkin et al. |
| 2017/0172857 A1 | 6/2017 | Tamarkin et al. |
| 2017/0181970 A1 | 6/2017 | Tamarkin et al. |
| 2017/0216334 A1 | 8/2017 | Tamarkin et al. |
| 2017/0231909 A1 | 8/2017 | Tamarkin et al. |
| 2017/0274084 A1 | 9/2017 | Friedman et al. |
| 2017/0340743 A1 | 11/2017 | Tamarkin et al. |
| 2017/0348418 A1 | 12/2017 | Tamarkin et al. |
| 2017/0354597 A1 | 12/2017 | Tamarkin et al. |
| 2017/0360705 A1 | 12/2017 | Tamarkin et al. |
| 2018/0000734 A1 | 1/2018 | Tamarkin et al. |

FOREIGN PATENT DOCUMENTS

| | | |
|---|---|---|
| CA | 2114537 A1 | 2/1993 |
| CA | 2154438 A1 | 1/1996 |
| CA | 2422244 A1 | 9/2003 |
| CA | 2502986 A1 | 5/2004 |
| CA | 2534372 A1 | 10/2005 |
| CH | 639913 A5 | 12/1983 |
| DE | 1 882 100 U | 11/1963 |
| DE | 1926796 A1 | 3/1970 |
| DE | 2 608 226 A1 | 9/1977 |
| DE | 4140474 A1 | 6/1993 |
| DE | 10009233 A1 | 8/2000 |
| DE | 10138495 A1 | 2/2003 |
| DE | 102004016710 A1 | 10/2005 |
| EP | 0 052 404 A2 | 5/1982 |
| EP | 0 156 507 A1 | 10/1985 |
| EP | 0 186 453 A2 | 7/1986 |
| EP | 0 213 827 A2 | 3/1987 |
| EP | 0 214 865 A2 | 3/1987 |
| EP | 0 270 316 A2 | 6/1988 |
| EP | 0 297 436 A2 | 1/1989 |
| EP | 0 336 812 A2 | 10/1989 |
| EP | 0 414 920 A1 | 3/1991 |
| EP | 0 211 550 B1 | 4/1991 |
| EP | 0 216 856 B1 | 7/1991 |
| EP | 0 454 102 A2 | 10/1991 |
| EP | 0 326 196 B2 | 3/1992 |
| EP | 0 484 530 A1 | 5/1992 |
| EP | 0 485 299 A1 | 5/1992 |
| EP | 0 488 089 A1 | 6/1992 |
| EP | 0 528 190 A1 | 2/1993 |
| EP | 0 552 612 A2 | 7/1993 |
| EP | 0 569 773 A2 | 11/1993 |
| EP | 0 404 376 B1 | 3/1994 |
| EP | 0 598 412 A2 | 5/1994 |
| EP | 0 391 124 B1 | 6/1995 |
| EP | 0 662 431 A2 | 7/1995 |
| EP | 0 535 327 B1 | 10/1996 |
| EP | 0 738 516 A1 | 10/1996 |
| EP | 0 757 959 A1 | 2/1997 |
| EP | 0 824 911 A2 | 2/1998 |
| EP | 0 829 259 A1 | 3/1998 |
| EP | 0 676 198 B1 | 10/1998 |
| EP | 0 979 654 A1 | 2/2000 |
| EP | 0 993 827 A1 | 4/2000 |
| EP | 1 025 836 A1 | 8/2000 |
| EP | 1 055 425 A2 | 11/2000 |
| EP | 0 506 197 B2 | 7/2001 |
| EP | 1 215 258 A2 | 6/2002 |
| EP | 1 287 813 A1 | 3/2003 |
| EP | 1 308 169 A1 | 5/2003 |
| EP | 1 375 386 A1 | 1/2004 |
| EP | 0 504 301 B1 | 3/2004 |
| EP | 1 428 521 A2 | 6/2004 |
| EP | 1 438 946 A1 | 7/2004 |
| EP | 1 189 579 B1 | 9/2004 |
| EP | 1 475 381 A1 | 11/2004 |
| EP | 1 500 385 A1 | 1/2005 |
| EP | 1 537 916 A1 | 6/2005 |
| EP | 1 600 185 A1 | 11/2005 |
| EP | 0 928 608 B1 | 3/2006 |
| EP | 1 653 932 A1 | 5/2006 |
| EP | 1 734 927 A1 | 12/2006 |
| EP | 1 758 547 A1 | 3/2007 |
| EP | 1 483 001 B1 | 11/2007 |
| EP | 1 584 324 B1 | 11/2007 |
| EP | 1 889 609 A2 | 2/2008 |
| EP | 1 902 706 A1 | 3/2008 |

(56) References Cited

FOREIGN PATENT DOCUMENTS

| | | |
|---|---|---|
| EP | 2 129 383 A1 | 12/2009 |
| EP | 2 422 768 A2 | 2/2012 |
| EP | 2 494 959 A1 | 9/2012 |
| FR | 2 456 522 A1 | 12/1980 |
| FR | 2 591 331 A1 | 6/1987 |
| FR | 2 640 942 A2 | 6/1990 |
| FR | 2 736 824 A1 | 1/1997 |
| FR | 2 774 595 A1 | 8/1999 |
| FR | 2 789 371 A1 | 8/2000 |
| FR | 2 793 479 A1 | 11/2000 |
| FR | 2 814 959 A1 | 4/2002 |
| FR | 2 833 246 A1 | 6/2003 |
| FR | 2 840 903 A1 | 12/2003 |
| FR | 2 843 373 A1 | 2/2004 |
| FR | 2 845 672 A1 | 4/2004 |
| FR | 2 848 998 A1 | 6/2004 |
| FR | 2 860 976 | 4/2005 |
| FR | 2 915 891 A1 | 11/2008 |
| GB | 808 104 A | 1/1959 |
| GB | 808 105 A | 1/1959 |
| GB | 922 930 A | 4/1963 |
| GB | 933 486 A | 8/1963 |
| GB | 998 490 A | 7/1965 |
| GB | 1 026 831 A | 4/1966 |
| GB | 1 033 299 A | 6/1966 |
| GB | 1 081 949 A | 9/1967 |
| GB | 1 121 358 A | 7/1968 |
| GB | 1 162 684 A | 8/1969 |
| GB | 1 170 152 A | 11/1969 |
| GB | 1 201 918 A | 8/1970 |
| GB | 1 347 950 A | 2/1974 |
| GB | 1 351 761 A | 5/1974 |
| GB | 1 351 762 A | 5/1974 |
| GB | 1 353 381 A | 5/1974 |
| GB | 1 376 649 A | 12/1974 |
| GB | 1 397 285 A | 6/1975 |
| GB | 1 408 036 A | 10/1975 |
| GB | 1 457 671 A | 12/1976 |
| GB | 1 489 672 A | 10/1977 |
| GB | 2 004 746 A | 4/1979 |
| GB | 1 561 423 A | 2/1980 |
| GB | 2 114 580 A | 8/1983 |
| GB | 2 166 651 A | 5/1986 |
| GB | 2 153 686 B | 7/1987 |
| GB | 2 172 298 B | 11/1988 |
| GB | 2 206 099 A | 12/1988 |
| GB | 2 337 461 A | 11/1999 |
| GB | 2 367 809 A | 4/2002 |
| GB | 2 406 330 A | 3/2005 |
| GB | 2 406 791 B | 2/2008 |
| GB | 2 474 930 A | 5/2011 |
| IL | 49491 A | 9/1979 |
| IL | 152 486 A | 5/2003 |
| JP | 55-069682 A | 5/1980 |
| JP | 56-039815 A | 4/1981 |
| JP | 57-044429 A | 3/1982 |
| JP | 60-001113 A | 1/1985 |
| JP | 61-275395 A | 12/1986 |
| JP | 62-241701 A | 10/1987 |
| JP | 63-119420 A | 5/1988 |
| JP | 01-100111 A | 4/1989 |
| JP | 01-156906 A | 6/1989 |
| JP | 02-184614 A | 7/1990 |
| JP | 02-255890 A | 10/1990 |
| JP | 03-050289 A | 3/1991 |
| JP | 04-51958 A | 2/1992 |
| JP | 04-282311 A | 10/1992 |
| JP | 04-312521 A | 11/1992 |
| JP | 05-070340 A | 3/1993 |
| JP | 05-213734 A | 8/1993 |
| JP | 06-100414 A | 4/1994 |
| JP | 06-263630 A | 9/1994 |
| JP | 06-329532 A | 11/1994 |
| JP | 07-215835 A | 8/1995 |
| JP | 08-040899 A | 2/1996 |
| JP | 08-501529 A | 2/1996 |
| JP | 08-119831 A | 5/1996 |
| JP | 08-165218 A | 6/1996 |
| JP | 08-277209 A | 10/1996 |
| JP | 09-84855 A | 3/1997 |
| JP | 09-099553 A | 4/1997 |
| JP | 09-110636 A | 4/1997 |
| JP | 10-114619 A | 5/1998 |
| JP | 10-332456 A | 12/1998 |
| JP | 11-501045 A | 1/1999 |
| JP | 11-250543 A | 9/1999 |
| JP | 2000-017174 A | 1/2000 |
| JP | 2000-080017 A | 3/2000 |
| JP | 2000-128734 A | 5/2000 |
| JP | 2000-191429 A | 7/2000 |
| JP | 2000-239140 A | 9/2000 |
| JP | 2000-351726 A | 12/2000 |
| JP | 2000-354623 A | 12/2000 |
| JP | 2001-002526 A | 1/2001 |
| JP | 2001-019606 A | 1/2001 |
| JP | 2001-072963 A | 3/2001 |
| JP | 2002-012513 A | 1/2002 |
| JP | 2002-047136 A | 2/2002 |
| JP | 2002-524490 A | 8/2002 |
| JP | 2002-302419 A | 10/2002 |
| JP | 2003-012511 A | 1/2003 |
| JP | 2003-055146 A | 2/2003 |
| JP | 2004-047136 A | 2/2004 |
| JP | 2004-250435 A | 9/2004 |
| JP | 2004-348277 A | 12/2004 |
| JP | 2005-314323 A | 11/2005 |
| JP | 2005-350378 A | 12/2005 |
| JP | 2006-008574 A | 1/2006 |
| JP | 2006-036317 A | 2/2006 |
| JP | 2006-103799 A | 4/2006 |
| JP | 2006-525145 A | 11/2006 |
| JP | 2007-131539 A2 | 5/2007 |
| JP | 2007-155667 A | 6/2007 |
| JP | 2007-326996 A | 12/2007 |
| KR | 0143232 A | 7/1998 |
| KR | 2001-003063 A | 1/2001 |
| NZ | 520014 A | 5/2005 |
| NZ | 540166 A | 6/2007 |
| RU | 2277501 C2 | 6/2006 |
| UA | 66796 C2 | 7/2001 |
| WO | WO 82/001821 A1 | 6/1982 |
| WO | WO 86/05389 A1 | 9/1986 |
| WO | WO 88/01502 A1 | 3/1988 |
| WO | WO 88/01863 A1 | 3/1988 |
| WO | WO 88/08316 A1 | 11/1988 |
| WO | WO 89/06537 A1 | 7/1989 |
| WO | WO 90/05774 A1 | 5/1990 |
| WO | WO 91/11991 A1 | 8/1991 |
| WO | WO 92/00077 A1 | 1/1992 |
| WO | WO 92/005142 A1 | 4/1992 |
| WO | WO 92/05763 A1 | 4/1992 |
| WO | WO 92/11839 A1 | 7/1992 |
| WO | WO 92/13602 A1 | 8/1992 |
| WO | WO 93/025189 A1 | 12/1993 |
| WO | WO 94/006440 A1 | 3/1994 |
| WO | WO 96/03115 A1 | 2/1996 |
| WO | WO 96/19921 A1 | 7/1996 |
| WO | WO 96/24325 A1 | 8/1996 |
| WO | WO 96/26711 A1 | 9/1996 |
| WO | WO 96/27376 A1 | 9/1996 |
| WO | WO 96/39119 A1 | 12/1996 |
| WO | WO 97/03638 A1 | 2/1997 |
| WO | WO 97/39745 A1 | 10/1997 |
| WO | WO 98/17282 A1 | 4/1998 |
| WO | WO 98/18472 A1 | 5/1998 |
| WO | WO 98/19654 A1 | 5/1998 |
| WO | WO 98/21955 A1 | 5/1998 |
| WO | WO 98/23291 A1 | 6/1998 |
| WO | WO 98/31339 A1 | 7/1998 |
| WO | WO 98/36733 A2 | 8/1998 |
| WO | WO 98/52536 A1 | 11/1998 |
| WO | WO 99/08649 A2 | 2/1999 |
| WO | WO 99/20250 A1 | 4/1999 |
| WO | WO 99/37282 A2 | 7/1999 |

(56) References Cited

FOREIGN PATENT DOCUMENTS

| | | |
|---|---|---|
| WO | WO 99/53923 A1 | 10/1999 |
| WO | WO 2000/09082 A1 | 2/2000 |
| WO | WO 2000/15193 A1 | 3/2000 |
| WO | WO 2000/23051 A1 | 4/2000 |
| WO | WO 2000/33825 A2 | 6/2000 |
| WO | WO 2000/38731 A1 | 7/2000 |
| WO | WO 2000/61076 A1 | 10/2000 |
| WO | WO 2000/62776 A1 | 10/2000 |
| WO | WO 2000/72805 A1 | 12/2000 |
| WO | WO 2000/76461 A2 | 12/2000 |
| WO | WO 2001/01949 A1 | 1/2001 |
| WO | WO 2001/05366 A1 | 1/2001 |
| WO | WO 2001/08681 A1 | 2/2001 |
| WO | WO 2001/10961 A1 | 2/2001 |
| WO | WO 2001/53198 A1 | 7/2001 |
| WO | WO 2001/54212 A1 | 7/2001 |
| WO | WO 2001/54679 A2 | 8/2001 |
| WO | WO 2001/62209 A2 | 8/2001 |
| WO | WO 2001/70242 A2 | 9/2001 |
| WO | WO 2001/76579 A1 | 10/2001 |
| WO | WO 2001/82880 A3 | 11/2001 |
| WO | WO 2001/82890 A1 | 11/2001 |
| WO | WO 2001/85102 A2 | 11/2001 |
| WO | WO 2001/85128 A2 | 11/2001 |
| WO | WO 2001/95728 A1 | 12/2001 |
| WO | WO 2002/00820 A1 | 1/2002 |
| WO | WO 2002/07685 A2 | 1/2002 |
| WO | WO 2002/15860 A1 | 2/2002 |
| WO | WO 2002/15873 A2 | 2/2002 |
| WO | WO 2002/24161 A1 | 3/2002 |
| WO | WO 2002/28435 A1 | 4/2002 |
| WO | WO 2002/41847 A1 | 5/2002 |
| WO | WO 2002/43490 A1 | 6/2002 |
| WO | WO 2002/062324 A2 | 8/2002 |
| WO | WO 2002/078667 A1 | 10/2002 |
| WO | WO 2002/087519 A2 | 11/2002 |
| WO | WO 2003/000223 A1 | 1/2003 |
| WO | WO 2003/002082 A1 | 1/2003 |
| WO | WO 2003/005985 A1 | 1/2003 |
| WO | WO 2003/013984 A1 | 2/2003 |
| WO | WO 2003/015699 A2 | 2/2003 |
| WO | WO 2003/051294 A2 | 6/2003 |
| WO | WO 2003/053292 A1 | 7/2003 |
| WO | WO 2003/055445 A2 | 7/2003 |
| WO | WO 2003/055454 A1 | 7/2003 |
| WO | WO 2003/070301 A1 | 8/2003 |
| WO | WO 2003/071995 A1 | 9/2003 |
| WO | WO 2003/075851 A2 | 9/2003 |
| WO | WO 2003/092641 A1 | 11/2003 |
| WO | WO 2003/094873 A1 | 11/2003 |
| WO | WO 2003/097002 A1 | 11/2003 |
| WO | WO 2004/017962 A2 | 3/2004 |
| WO | WO 2004/037197 A2 | 5/2004 |
| WO | WO 2004/037225 A2 | 5/2004 |
| WO | WO 2004/003284 A1 | 8/2004 |
| WO | WO 2004/064769 A2 | 8/2004 |
| WO | WO 2004/064833 A1 | 8/2004 |
| WO | WO 2004/071479 A1 | 8/2004 |
| WO | WO 2004/078158 A2 | 9/2004 |
| WO | WO 2004/078896 A1 | 9/2004 |
| WO | WO 2004/093895 A1 | 11/2004 |
| WO | WO 2004/112780 A1 | 12/2004 |
| WO | WO 2005/009416 A1 | 2/2005 |
| WO | WO 2005/011567 A2 | 2/2005 |
| WO | WO 2005/018530 A2 | 3/2005 |
| WO | WO 2005/032522 A1 | 4/2005 |
| WO | WO 2005/044219 A1 | 5/2005 |
| WO | WO 2005/063224 A1 | 7/2005 |
| WO | WO 2005/065652 A1 | 7/2005 |
| WO | WO 2005/076697 A2 | 8/2005 |
| WO | WO 2005/097068 A1 | 10/2005 |
| WO | WO 2005/102282 A1 | 11/2005 |
| WO | WO 2005/102539 A1 | 11/2005 |
| WO | WO 2005/117813 A1 | 12/2005 |
| WO | WO 2006/003481 A2 | 1/2006 |
| WO | WO 2006/010589 A2 | 2/2006 |
| WO | WO 2006/011046 A1 | 2/2006 |
| WO | WO 2006/020682 A1 | 2/2006 |
| WO | WO 2006/028339 A1 | 3/2006 |
| WO | WO 2006/031271 A2 | 3/2006 |
| WO | WO 2006/045170 A2 | 5/2006 |
| WO | WO 2006/079632 A1 | 8/2006 |
| WO | WO 2006/081327 A2 | 8/2006 |
| WO | WO 2006/091229 A2 | 8/2006 |
| WO | WO 2006/100485 A1 | 9/2006 |
| WO | WO 2006/120682 A2 | 11/2006 |
| WO | WO 2006/121610 A2 | 11/2006 |
| WO | WO 2006/122158 A2 | 11/2006 |
| WO | WO 2006/129161 A2 | 12/2006 |
| WO | WO 2006/131784 A1 | 12/2006 |
| WO | WO 2007/007208 A2 | 1/2007 |
| WO | WO 2007/010494 A1 | 1/2007 |
| WO | WO 2007/012977 A2 | 2/2007 |
| WO | WO 2007/023396 A2 | 3/2007 |
| WO | WO 2007/031621 A2 | 3/2007 |
| WO | WO 2007/039825 A2 | 4/2007 |
| WO | WO 2007/054818 A2 | 5/2007 |
| WO | WO 2007/072216 A2 | 6/2007 |
| WO | WO 2007/082698 A1 | 7/2007 |
| WO | WO 2007/085902 A2 | 8/2007 |
| WO | WO 2007/099396 A2 | 9/2007 |
| WO | WO 2007/111962 A2 | 10/2007 |
| WO | WO 2008/008397 A2 | 1/2008 |
| WO | WO 2008/010963 A2 | 1/2008 |
| WO | WO 2008/038147 A2 | 4/2008 |
| WO | WO 2008/041045 A1 | 4/2008 |
| WO | WO 2008/075207 A2 | 6/2008 |
| WO | WO 2008/087148 A2 | 7/2008 |
| WO | WO 2008/104734 A1 | 9/2008 |
| WO | WO 2008/110872 A2 | 9/2008 |
| WO | WO 2008/152444 A2 | 12/2008 |
| WO | WO 2009/007785 A2 | 1/2009 |
| WO | WO 2009/069006 A2 | 6/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/090558 A2 | 7/2009 |
| WO | WO 2009/098595 A2 | 8/2009 |
| WO | WO 2011/006026 A1 | 1/2011 |
| WO | WO 2011/013008 A2 | 2/2011 |
| WO | WO 2011/013009 A2 | 2/2011 |
| WO | WO 2011/026094 A2 | 3/2011 |
| WO | WO 2011/039637 A2 | 4/2011 |
| WO | WO 2011/039638 A2 | 4/2011 |
| WO | WO 2011/064631 A1 | 6/2011 |
| WO | WO 2011/106026 A1 | 9/2011 |
| WO | WO 2011/138678 A2 | 11/2011 |
| WO | WO 2013/136192 A2 | 9/2013 |
| WO | WO 2014/134394 A1 | 9/2014 |
| WO | WO 2014/134427 A1 | 9/2014 |
| WO | WO 2014/151347 A1 | 9/2014 |
| WO | WO 2014/201541 A1 | 12/2014 |
| WO | WO 2015/075640 A1 | 5/2015 |
| WO | WO 2015/114320 A1 | 8/2015 |
| WO | WO 2015/153864 A2 | 10/2015 |
| WO | WO 2017/029647 A1 | 2/2017 |
| WO | WO 2017/030555 A1 | 2/2017 |

OTHER PUBLICATIONS

"Suppositories?" CareCure Community, SCI Forum [online]. http://sci.rutgers.edu/forum/showthread.php?4176-Suppositories. Published: Apr. 16, 2002, 3 pages.

1058. Benzalkonium Chloride; 2350. Citric Acid; 6143. Methyl Salicylate. The Merck Index: An Encyclopedia of Chemicals, Drugs, and Biologicals. 13th Edition, 2001, pp. 181, 405-406, 1090-1091, 1556.

242. Allantoin, The Merck Index: An Encyclopedia of Chemicals, Drugs, and Biologicals. 10th edition, Merck & Co., Inc., 1983, p. 39.

Abdullah, G.Z. et al. (Jan. 2013) "Carbopol 934, 940 and Ultrez 10 as viscosity modifiers of palm olein esters based nano-scaled emulsion containing ibuprofen" *Pak J Pharm Sci*, 26(1):75-83.

(56) References Cited

OTHER PUBLICATIONS

Abrams et al., "Ciclopirox gel treatment of scalp seborrheic dermatitis," in: Shuster, S. (ed.) Hydroxy-Piridones as Antifungal Agents with Special Emphasis on Onychomycosis. Springer, Berlin, Heidelberg; 1999, Chapter 8, pp. 45-50.
Adachi, "Storage and Oxidative Stability of O/W/ Nano-emulsions," Foods Food Ingredients J. Jpn., 2004, 209(11), 1 page (Abstract).
Adisen et al., "Topical tetracycline in the treatment of acne vulgaris," J Drugs Dermatol., Oct. 2008, 7(10):953-955.
Alcohol SDA 40B, 200 Proof. Material Safety Data Sheets [online]. Retrieved from the Internet: http://www.pharmco-prod.com/pages/MSDS/SDA.sub.--40B.sub.--200.pdf, on Dec. 9, 2008. MSDS 044, Revision 2.1, Revision Date Dec. 2005, 2 pages.
Alcohol, Wikipedia, the free encyclopedia [online]. Last modified on Apr. 23, 2014. Retrieved on May 17, 2014, http://en.wikipedia.org/wiki/Alcohol, 17 pages.
ALDARA™ (imiquimod) Cream. Highlights of Prescribing Information, Graceway Pharmaceuticals, LLC, Mar. 2007, 29 pages.
Allantoin, Römpp Online, retrieved on Sep. 23, 2015, https://roempp.thieme.de/roempp4.0/do/data/RD-O 1-01552, 5 pages.
Al-Mughrabi et al., "Effectiveness of Essential Oils and Their Combinations with Aluminum Starch Octenylsuccinate on Potato Storage Pathogens," TEOP, 2013, 16(1):23-31.
Ambrose et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, Sep. 1991, 35(9):1799-1803.
Aminobenzoic Acid, Knovel, 2006, retrieved on Apr. 18, 2012, http://www.knovel.com/web/portal/knovel_content?p_p_id=EXT_KNOVEL_CONTENT . . . , 2 pages.
Anton et al., "Water-in-oil nano-emulsion formation by the phase inversion temperature method: a novel and general concept, a new template for nanoencapsulation," Proceedings of the 33rd Annual Meeting and Exposition of the Controlled Release Society, Jul. 2006, Vienna, Austria, 2 pages.
Arct et al., "Common cosmetic hydrophilic ingredients as penetration modifiers of flavonoids," International Journal of Cosmetic Science, Dec. 2002, 24(6):357-366 (Abstract Only).
Arisan, Kozmetic ve Kisisel Bakim Urunleri Grubu, retrieved on Dec. 10, 2008, http://www.arisankimya.com/kozmetik.htm, 8 pages.
Arquad HTL8-MS, AkzoNobel Functional Applications, retrieved on Mar. 18, 2013, Retrieved from the Internet: <URL: http://sc.akzonobel.com/en/fa/Pages/product-detail.aspx?prodID=8764>, 1 page.
Aslam et al. (2015) "Emerging drugs for the treatment of acne" *Expert Opin Emerging Drugs*, 20:91-101.
Atopic Dermatitis/Eczema, ibabydoc.com, Copyright 2000, retrieved on Jan. 30, 2010, http://www.ibabydoc.com/online/diseaseeczema.asp 6 pages.
Ausburger and Shangraw, "Bubble size analysis of high consistency aerosol foams and its relationship to foam rheology; Effects fo Container Emptying, Propellent Type, and Time," J. Pharma Sci, Apr. 1968, 57(4):624-631.
Austria, et al., "Stability of vitamin C derivatives in solution and topical formulations", Journal of Pharmaceutical and Biomedical Analysis, 1997, 15:795-801.
Barry and Badal, "Stability of minocycline, doxycycline, and tetracycline stored in agar plates and microdilution trays," Current Microbiology, 1978, 1:33-36.
Barry and Woodford, "Comparative bio-availability and activity of proprietary topical corticosteroid preparations: vasoconstrictor assays on thirty-one ointments," British J. Dermatology, 1975, 93:563-571.
Baskaran et al., "Poloxamer-188 improves capillary blood flow and tissue viability in a cutaneous burn wound," J. Surg. Res., 2001, 101(1):56-61.
Beauty Banter, "Interesting list of comedogenic ingredients!!!!!!!!!!!!" QVC blog, Interesting list of comedogenic ingredients, 2014, 1-14.

Bell-Syer et al., "A systematic review of oral treatments for fungal infections of the skin of the feet," J. Dermatology. Treat, 2001, 12:69-74.
Ben-Et and Tatarsky "Application of NMR for the Determination of HLB Values of Nonionic Surfactants," Journal of the American Oil Chemists Society,Mar. 20, 1972, 49:499-500.
Bernstein and Harrison, "Effects of the Immunomodulating Agent R837 on Acute and Latent Herpes Simplex Virus Type 2 Infections," Antimicrobial Agents and Chemotherapy, Sep. 1989, 33(9):1511-1515.
Beuchat (Feb. 1983) "Influence of Water Activity on Growth, Metabolic Activities and Survival of Yeasts and Molds" *J Food Prot*, 46(2):135-141.
Blaney and Cook, "Topical use of tetracycline in the treatment of acne," Arch Dermatol, Jul. 1976, 112:971-973.
Blute et al., "Phase behaviour of alkyl glycerol ether surfactants", Physikalische Chemie/Physical Chemistry Tenside Surf. Det., 1998, 35(3):207-212.
Boehm et al., "Synthesis of high specific activity [.sup.3 H]-9-cis-retinoic acid and its application for identifying retinoids with unusual binding properties," J. Med. Chem., 1994, 37:408-414.
Brenes, et al., "Stability of Copigmented Anthocyanins and Ascorbic Acid in a Grape Juice Model System", J. Agric Food Chem, 2005, 53(1):49-56 (Abstract Only).
Brisaert, M. et al. (1996) "Investigation on the chemical stability of erythromycin in solutions using an optimization system" *Pharm World Sci*, 18(5):182-186.
Bronopol, 2-BROMO-2-NURO-1,3-PROPANEDIOL, Chemical land, Jul. 17, 2006, retrieved on Jun. 4, 2011, http://chemicalland21.com/specialtychem/perchem/BRONOPOL.html, 4 pages.
Brown et al., "Structural dependence of flavonoid interactions with Cu2+ ions: implications for their antioxidant properties," Biochem. J., 1998, 330:1173-1178.
Buck and Guth, "Treatment of Vaginal Intraepithelial Neoplasia (Primarily Low Grade) with Imiquimod 5% Cream", Journal of Lower Genital Tract Disease, 2003, 7(3):290-293.
Bucks et al., "Bioavailability of Topically Administered Steroids: A "Mass Balance" Technique," J. Investigative Dermatology, 1988, 91(1):29-33.
Bunker and Dowd, "Alterations in Scalp Blood Flow after the Epicutaneous Application of 3% Minoxidil and 0.1% Hexyl Nicotinate in Alopecia," British Society for Investigative Dermatology, Sep. 1986, 117(5):668-669.
Burn Patients Need Vitamin D Supplements, NUTRAingredients.com, Jan. 23, 2004, retrieved on May 5, 2010, http://www.nutraingredients.com/Research/Burn-patients-need-vitamin-D-supplements, 1page.
Burton and Marshall, "Hypertrichosis due to minoxidil," British J. Dermatology, 1979, 101:593-595.
C12-15 Alkyl Benzoate, Paula's Choice Skincare, retrieved on Oct. 24, 2010, http://www.cosmeticscop.com/cosmetic-ingredient-dictionary/definition/259/c12-15-alkyl-benzoate.aspx, 1 page.
Campos and Silva, "Ascorbic Acid and Its Derivatives in Cosmetic Formulations", Cosmetics and Toiletries, 2000, 115(6):59-62 (Abstract Only).
Can Tuberous Sclerosis Be Prevented?, Sharecare, 2002, retrieved on Aug. 29, 2013, <URL: http://www.sharecare.com/health/autosomal-dominant-genetic-disorders/can-tuberous-sclerosis-be-prevented;jsessionid=850579B60520A907DE75930E061E60E6>, 2 pages.
Canavan et al. (2016) "Optimizing Non-Antibiotic Treatments for Patients with Acne: A Review" *Dermatol Ther*, 6:555-578.
Carapeti et al., "Topical diltiazem and bethanechol decrease anal sphincter pressure and heal anal fissures without side effects," Dis Colon Rectum, 2000, 43(10):1359-1362.
Carbowax 1000MSDS, Material Safety Data Sheet for Polyethylene glycol 1000 MSDS, last updated Nov. 6, 2008, retrieved on Dec. 13, 2008, http://www.sciencelab.com/xMSDS-Polyethylene.sub.-glycol.sub.-1000-9926-622, 6 pages.
Carelli et al., "Effect of Vehicles on Yohimbine Permeation Across Excised Hairless Mouse Skin", Pharm Acta Hely, Aug. 1978, 73(3):127-134 (Abstract Only).
Causes of Psoriasis, retrieved on Sep. 9, 2010, http://www.quickcare.org/skin/causes-of0psoriasis.html, 3 pages.

(56) References Cited

OTHER PUBLICATIONS

Cetearyl Alcohol, Natural Wellbeing, Copyright 2001-2012, retrieved on Apr. 10, 2014, http://www.naturalwellbeing.com/learning-center/Cetearyl_Alcohol, 3 pages.
Chebil et al., "Solubility of Flavonoids in Organic Solvents," J. Chem. Eng. Data, 2007, 52(5):1552-1556 (Abstract Only).
Chemical Characteristics, The Olive Oil Source, ©1998-2015, retrieved on Jun. 12, 2015, http://www.oliveoilsource.com/page/chemical-characteristics, 10 pages.
Cheshire and Freeman, "Disorders of Sweating," Semin Neurol, 2003, 23(4):399-406.
Chevrant-Breton et al., "Etude du Traitement Capillaire <<Bioscalin>> dans les Alopecies Diffuses de la Femme", Gazette Medicale, 1986, 93(17):75-79 (English Abstract).
Chiang et al., "Bioavailability Assessment of Topical Delivery Systems: In Vitro Delivery of Minoxidil from Prototypical Semi-Solid Formulations", Int. J. Pharm, 1989, 49(2):109-114 (Abstract Only).
Chinnian et al., "Photostability Profiles of Minoxidil Solutions", PDA J. Pharm Sci Technol., Mar.-Apr. 1996, 50(2):94-98 (English Abstract).
Chollet et al., "Development of a Topically Active Imiquimod Formulation", Pharmaceutical Development and Technology, 1999, 4(1):35-43.
Chollet et al., "The Effect of Temperatures on the Solubility of Imiquimod in Isostearic Acid", Abstract 3031, Pharmaceutical Research, Nov. 1997, 14(11 Supplemental):S475.
Chrysos et al., "Effect of nifedipine on rectoanal motility," Dis Colon Rectum, Feb. 1996, 39(2):212-216.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.
Cloez-Tayarani et al., "Differential effect of serotonin on cytokine production in lipopolysaccharide-stimulated human peripheral blood mononuclear cells: involvement of 5-hydroxytryptamine2A receptors," Int. Immunol., 2003, 15:233-240.
Coal Tars and Coal-Tar Pitches, *Report on Carcinogens, Twelfth Edition*, 2011, 3 pages.
Coatzee et al., "Acceptability and feasibility of Micralax® applicators and of methyl cellulose gel placebo for large-scale clinical trials of vaginal microbicides," AIDS, 2001, 15:1837-1842.
Coconut Oil, Wikipedia, the free encyclopedia, retrieved on Jul. 3, 2015, https://en.wikipedia.org/wiki/Coconut_oil, 8 pages.
Codex Standard for Olive Oils and Olive Pomace Oils Codex Stan 33/1981, Adopted in 1981, recently amended 2013, 8 pages.
Cole and Gazewood, "Diagnosis and Treatment of Impetigo," American Family Physical Website, 2007, http://www.aafp.org/afp, 6 pages.
Colloidal Silica, W.R. Grace & Co. Enriching Lives, Everywhere™, 2011, retrieved on Jun. 4, 2011, http://www.grace.com/engineeredmaterials/materialsciences/colloidalsilica/default.aspx, 4 pages.
Communication of a Notice of Opposition in European Application No. 03772600.7, dated Jan. 13, 2015, 36 pages.
Cook and Mortenson, "Nifedipine for treatment of anal fissures," Dis Colon Rectum, 2000, 43(3):430-431.
Craig, D.Q.M. et al. (Jul. 1994) "An investigation into the structure and properties of Carbopol 934 gels using dielectric spectroscopy and oscillatory rheometry" *J Controlled Rel*, 30(3):213-223 (Abstract).
Cremophor A Grades, BASF The Chemical Company, Jan. 2008, 6 pages.
Croda Crop Care, Arlacel 165, 2011, retrieved on Aug. 3, 2015, http://www.crodapersonalcare.com/home.aspx?view=dtl&d=content&s=157&r=401&p=2578&productName=&inciname=&application=&subapplication=&productfunction=&consumerbenefit=&prodID=1926, 2 pages.
Croda Product Care Europe, Cetomacrogol 1000, 2011, retrieved on Aug. 3, 2015, http://www.crodapersonalcare.com/home.aspx?view=dtl&d=content&s=157&r=273&p=1859&productName=&inciname=&chemicaltype=&application=&subapplication=&productfunction=&consumerbenefit=&prodID=27, 1 page.
Crohn's Disease, Merck Manual Home Edition, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
Cunha, "Minocycline versus Doxycycline in the treatment of Lyme Neuroborreliosis," Clin. Infect. Diseases, 2000, 30: 237-238.
Dacarbazine, Chemical Book, 2010, retrieved on Oct. 18, 2013, <URL: http://www.chemicalbook.com/ChemicalProductProperty_EN_CB7710656.htm>, 2 pages.
Dalby et al., "Determination of Drug Solubility in Aerosol Propellants," Pharmaceutical Research, 1991, 8(9):1206-1209.
Dawber and Rundegren, "Hypertrichosis in Females Applying Minoxidil Topical Solution and in Normal Controls", JEADV, 2003, 17:271-275.
Denatonium Benzoate, retrieved Dec. 9, 2008, http://www.newdruginfo.com/pharmaceopeia/usp28/v28230/usp28nf23s0_m-22790.htm, 2 pages.
Dentinger, et al., "Stability of Nifedipine in an Extemporaneously Compounded Oral Solution", American Journal of Health-System Pharmacy, 2003, 60(10):1019-1022 (English Abstract).
Derivative, Merriam Webster Online Dictionary, retrieved on Jul. 5, 2008, http://www.merriam-webster.com/cgi-bin/dictionary?book=dictionary&va=derivative, 1 page.
Devos and Miller, "Antisense Oligonucleotides: Treating neurodegeneration at the Level of RNA," Neurotherapeutics, 2013, 10:486-497.
Diethyltoluamide, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.
Disorder, American Heritage Dictionary of the English Language, 2007, retrieved on Oct. 9, 2010, http://www.credoreference.com/entry/hmdictenglang/disorder, 1 page.
Draelos, "Antiperspirants and the Hyperhidrosis Patients," Dermatologic Therapy, 2001, 14:220-224.
Drug Index—Dacarbazine, BC Cancer Agency, Jun. 2004, retrieved on Oct. 18, 2013, <URL:http://www.bccancer.bc.ca/HPI/DrugDatabase/DrugIndexPro/Dacarbazine.htm>, 6 pages.
Drugfuture, Chemical Index Database, "Sorbitan Esters" Monograph [online]. Retrieved from: http://www.drugfuture.com/chemdata/sorbitan-esters.html, on Jul. 1, 2016, 2 pages.
Durian et al., "Scaling behavior in shaving cream," The American Physical Society, Dec. 1991, 44(12):R7902-7905.
Durmortier et al., "A review of poloxamer 407 pharmaceutical and pharmacological characteristics," Pharmaceutical Res., Dec. 2006, 23(12):2709-2728.
E7023 Ethanol 200 Proof (Absolute), Sigma-Aldrich Co., © 2008, retrieved on Dec. 9, 2008, http://www.sigmaaldrich.com/catalog/ProductDetail.do?N4=E7023SIAL&N5=SEAR-CH.sub.--CONCAT.sub.--PNOBRAND.sub.--KEY&F=SPEC, 2 pages.
Ebadi et al., "Healing effect of topical nifedipine on skin wounds of diabetic rats," DARU, 2003, 11(1):19-22.
Edens et al., "Storage Stability and Safety of Active Vitamin C in a New Dual-Chamber Dispenser", Journal of Applied Cosmetology, 1999, 17(4):136-143 (English Abstract).
Edirisinghe et al., "Effect of fatty acids on endothelium-dependent relaxation in the rabbit aorta", Clin Sci, Aug. 2006, 111(2): 145-51.
Edwards, "Imiquimod in Clinical Practice," J. Am Acad Dermatol., Jul. 2000 43(1, Pt 2):S12-S17 (English Abstract).
Effendy and Maibach "Surfactants and Experimental Irritant Contact Dermatitis." Contact Dermatol., 1995, 33:217-225.
Elias and Ghadially, "The aged epidermal permeability barrier," Clinical Geriatric Medicine, Feb. 2002, 103-120.
Ellis et al., "The Treatment of Psoriasis with Liquor Carbonis Detergens," J. Invest Dermatology, 1948, 10:455-459.
Emulsifiers With HLB Values, The Herbarie, retrieved on Aug. 5, 2009, http://www.theherbarie.com/files/resources-center/formulating/Emulsifiers-.sub.--HLB.sub.--Values.pdf, 3 pages.
Esposito et al., "Nanosystems for Skin Hydration: A Comparative Study," International Journal of Cosmetic Science, 2007, 29: 39-47.
Established ("Approved") Excipients, Encyclopedia Of Pharmaceutical Technology, Second Edition, © 2002, vol. 3, 2146-2147.

(56) References Cited

OTHER PUBLICATIONS

Ethylene Oxide Derivatives: An Essence of Every Industry, retrieved on Jul. 12, 2011, http://www.emulsifiers.in/ethylene_oxide_derivatives2.htm, 3 pages.
European Patent Application No. 03772600.7 (Patent No. 1556009): Communication of a Notice of Opposition, dated Sep. 23, 2015, 42 pages.
European Patent Application No. 03772600.7 (Patent No. 1556009): Communication of a Notice of Opposition. dated Sep. 24, 2015, 30 pages.
European Patent Application No. 03772600.7 (Patent No. 1556009): Reply of the Patent Proprietor to the Notices of Opposition, dated May 9, 2016, 134 pages.
European Patent Application No. 03772600.7 (Patent No. 1556009): Summons to Attend Oral Proceedings, dated Jun. 30, 2016, 19 pages.
European Patent Application No. 03772600.7 (Patent No. 1556009): Interlocutory Decision in Opposition Proceedings, dated Feb. 3, 2017, 54 pages.
European Patent Application No. 03772600.7 (Patent No. 1556009): Minutes of Oral Proceedings, dated Feb. 3, 2017, 6 pages.
Excessive Sweating, Merck Manual Home Edition, Oct. 2007, retrieved on Apr. 14, 2011, www.merckmanuals.com/home/print/sec18/ch206/ch206c.html, 2 pages.
Fantin et al., "Critical influence of resistance to streptogramin B-type antibiotics on activity of RP 59500 (Quinupristin-dalfopristin) in experimental endocarditis due to *Staphylococcus aureus*," Antimicrob Agents and Chemothery, Feb. 1995, 39:400-405.
Farahmand et al., "Formulation and Evaluation of a Vitamin C Multiple Emulsion", Pharmaceutical Development and Technology, May 2006, 11(2):255-261 (English Abstract).
Flick, Cosmetic and Toiletry Formulations, 2nd Edition, Copyright 1996, vol. 5, 251-309.
Floyd, "Silicone Surfactants: Applicants in the Personal Care Industry," Silicone Surfactants, 1999, Chapter 7, 181-207.
Fluhr et al., "Glycerol accelerates recovery of barrier function in vivo," Acta Derm. Venereol, 1999, 79:418-421.
Foamix Pharmaceuticals Ltd. (May 1, 2017) "Foamix Pharmaceuticals Announces Plans for Additional Phase 3 Trial for FMX101 in Moderate to Severe Acne," Press Release [online]. Retrieved from: http://www.foamix.co.il/news.asp?nodeID=564&itemID=204, on Jun. 12, 2017, 5 pages.
Foamix Pharmaceuticals, Statement: Use of Luviquat FC 370, Approved by Yohan Hazot, May 3, 2016, 3 pages.
Fontana, "Water Activity: Why It is Important for Food Safety," International Conference on Food Safety, Nov. 16-18, 1998, 177-185.
Fontana (Apr. 1999) "Pharmaceutical Applications for Water Activity" *Pharmaceutical Online* [online]. Retrieved from https://www.pharmaceuticalonline.com/doc/pharmaceutical-applications-for-water-activit- . . . , on Jan. 17, 2018 (4 pages).
Frankel, A.J. et al. (2010) "Coal Tar 2% Foam in Combination with a Superpotent Corticosteroid Foam for Plaque Psoriasis. Case Report and Clinical Implications" *J Clin Aesthet Dermatol*, 3(10):42-45.
Fully-Refined Paraffin Wax (FRP Wax), Industrial Raw Materials LLC, Feb. 21, 2008, retrieved on Aug. 22, 2013, <http://irmwax.com/Wax/Paraffinffully_refined.asp> 1 page.
Gallarate et al., "On the Stability of Ascorbic Acid in Emulsified Systems for Topical and Cosmetic Use", International Journal of Pharmaceutics, 1999, 188:233-241.
Galligan et al., "Adhesive Polyurethane Liners for Anterior Restorations," J. Dent. Res., Jul.-Aug. 1968, 629-632.
Garti et al. "Sucrose Esters microemulsions," J. Molec. Liquids, 1999, 80:253-296.
Gas Gangrene, Merck Manual Home Edition, 2008, retrieved on Jan. 16, 2013, <http://www.merckmanuals.com/home/infections/bacterial_infections/gas_gangrene.html?qt=gas gangrene&alt=sh>1 page.
Gelbard et al. "Primary Pediatric Hyperhidrosis: A Review of Current Treatment Options," Pediatric Dermatology, 2008, 25(6):591-598.
Gels, UNC: The Pharmaceutics and Compounding Laboratory, retrieved on Aug. 25, 2014, http://pharmlabs.unc.edu/labs/gels/agents/htm, 4 pages.
Ghica, M.V. et al. (2011) "Design and optimization of some collagen-minocycline based hydrogels potentially applicable for the treatment of cutaneous wound infections" *Pharmazie*, 66:853-861.
Gill et al., "Adverse Drug Reactions in a Paediatric Intensive Care Unit," Acta Paediatric, 1995, 84:438-441.
Gladkikh, "Ascorbic Acid and Methods of Increasing its Stability in Drugs", Translated from Khimiko-Farmatsevticheskii Zhurnal, 1970, 4(12):37-42.
Glaser and Ballard, "Hyperhidrosis: A Comprehensive and Practical Approach to Patient Management," Expert Rev. Dermatol., Oct. 2006, 1(6):773-775.
Google Search Strategy for Minocycline Solubility, retrieved on Aug. 15, 2013, <http://www.googl.com/search?rls=com.microsoft%3Aen-us%3AIE-SearchBox&q-melocycline+solubility>, 1 page.
Graves et al., "Structure of Concentrated Nanoemulsions," The Journal of Chemical Physics, Apr. 1, 2005, 122:134703, 6 pages.
Griffin, "Calculation of HLB Values of Non-Ionic Surfactants," Journal of the Society of Cosmetic Chemists, May 14, 1954, 249-256.
Groveman et al., "Lack of Efficacy of Polysorbate 60 in the Treatment of Male Pattern Baldness", Arch Intern Med, 1985, 145:1454-1458.
Gschnait et al., "Topical Indomethacin Protects from UVB and UVA Irradiation," Arch. Dermatol. Res., 1984, 276:131-132.
Hakan et al., "The protective effect of fish oil enema in acetic acid and ethanol induced colitis," The Turkish Journal of Gastroenterology, 2000, 11(2):155-161.
Hall, "Diaper Area Hemangiomas: A Unique Set of Concerns," retrieved on Dec. 1, 2008, http://members.tripod.com/.about.Michelle.sub.--G/diaper.html, 8 pages.
HALLSTAR® GMS SE/AS, retrieved on Jun. 4, 2011, http://www.hallstar.com/pis.php?product=1H022, 1 page.
Hammer et al., "Anti-Microbial Activity of Essential Oils and other Plant extracts," J. Applied Microbiology, 1999, 86:985-990.
Hargreaves, "Chemical Formulation, An Overview of Surfactant-Based Preparations Used in Everyday Life", The Royal Society of Chemistry, 2003, 114-115.
Harrison et al., "Effects of cytokines and R-837, a cytokine inducer, on UV-irradiation augmented recurrent genital herpes in guinea pigs", Antiviral Res., 1991, 15(4):315-322.
Harrison et al., "Modification of Immunological Responses and Clinical Disease During Topical R-837 Treatment of Genital HSV-2 Infection," Antiviral Research, 1988, 10:209-224.
Harrison et al., "Pharmacokinetics and Safety of Imiquimod 5% Cream in the Treatment of Actinic Keratoses of the Face, Scalp, or Hands and Arms", Arch. Dermatol. Res., Jun. 2004, 296(1):6-11 (English Abstract).
Harrison et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, Sep. 1994, 38(9):2059-2064.
Harry, "Skin Penetration," The British Journal of Dermatology and Syphilis, 1941, 53:65-82.
Hashim et al., "Tinea versicolor and visceral leishmaniasis," Int J Dermatol., Apr. 1994; 33(4):258-259 (Abstract).
Haute.De, "Substance (INCI-Designation): Triethanolamine" [online]. Retrieved on Sep. 14, 2015, http://www.haut.de/service/inci/anzeige&id=I6384&query=Triethanolamine&funktio . . . ; German with English translation, 3 pages.
Haw, "The HLB System: A Time Saving Guide to Surfactant Selection," Presentation to the Midwest Chapter of the Society of Cosmetic Chemists, Mar. 9, 2004, 39 pages.
Healy, "Gelled Emollient Systems for Controlled Fragrance Release and Enhanced Product Performance," Cosmetics and toiletries, 2002, 117(2): 47-54.
Heart Failure, The Merck Manual, 2008, retrieved Oct. 9, 2010, http://www.merck.com/mmhe/sec03/ch025/ch025a.html, 12 pages.

(56) References Cited

OTHER PUBLICATIONS

Helmenstine, "Surfactant Definition—Chemistry Glossary Definition of Surfactant," About.com Chemistry, retrieved on Mar. 5, 2012, http://chemistry.about.com/od/chemistryglossary/g/surfactant.htm, 1 page.
Hepburn, "Cutaneous leishmaniasis," Clin Exp Dermatol, Jul. 2000, 25(5):363-370 (Abstract).
HLB Systems, Pharmcal.tripod.com, retrieved on Sep. 17, 2010, http://pharmcal.tripod.com/ch17.htm, 3 pages.
HLB-Numbers, Sigma Aldrich, 2009, retrieved on Feb. 2, 2009, http://www.sigmaaldrich.com/materials-science/micro-and-nanoelectronics/l-ithography-nanopatterning/hlb-numbers.html, 3 pages.
How to Have a Healthy Libido in Mid-Life and Beyond, GreenWillowTree.com, Jan. 2001, retrieved on Jul. 28, 2012, http://www.greenwillowtree.com/Page.bok?file=libido.html, 5 pages.
Hubbe, Colloidal Silica, Mini-Encyclopedia of Papermaking Wet-End Chemistry: Additives and Ingredients, their Composition, Functions, Strategies for Use, Feb. 1, 2001, retrieved on Jun. 4, 2011, http://www4.ncsu.edu/~hubbe/CSIL.htm, 2 pages.
Human Immunodeficiency Virus Infection, Merck Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh >, 11 pages.
Hwang et al., "Isolation and identification of mosquito repellents in *Artemisia vulgaris*," J. Chem. Ecol., 1985, 11: 1297-1306.
ICI Americas Inc., "Meaning of HLB Advantages and Limitations" Chapter 1 in *The HLB System. A Time-Saving Guide To Emulsifier Selection.* Wilmington, Delaware: 1980; pp. 1-4.
Ikuta et al., "Scanning Electron Microscopic Observation of Oil/Wax/Water/Surfactant System", Journal of SCCJ, 2004, 34(4):280-291 (English Abstract).
Indomethacin, Aug. 15, 2009, retrived on Jun. 3, 2011, http://it03.net/com/oxymatrine/down/1249534834.pdf, 3 pages.
Innocenzi et al., "An Open-Label Tolerability and Effacy Study of an Aluminum Sesquichlorhydrate Topical Foam in Axillary and Palmar Primary Hyperhidrosis," Dermatologic Therapy, 2008, 21:S27-S30.
Izquierdo et al. "Formation and Stability of Nano-Emulsions Prepared Using the Phase Inversion Temperature Method," Langmuir, 2002, 18(1):26-30 (Abstract).
Jan, "Troubled Times: Detergent Foam," retrieved on Feb. 9, 2012, http://zetatalk.com/health/theal17c.htm, 2 pages.
Joseph, "Understanding foams & foaming," University of Minnesota, May 1997, http://www.aem.umn.edu/people/faculty/joseph/archive/docs/understandingfoams.pdf, 8 pages.
Kalkan et al., "The Measurement of Sweat Intensity Using a New Technique," Tr. J. of Medical Sciences, 1998, 28:515-517.
Kanamoto et al., "Pharmacokinetics of two rectal dosage forms of ketoprofen in patients after anal surgery," J Pharmacobiodyn., Mar. 1988, 11(3):141-145.
Kang et al., "Enhancement of the Stability and Skin Penetration of Vitamin C by Polyphenol", Immune Netw., Dec. 2004, 4(4):250-254 (English Abstract).
Kanicky, J.R. and D.O. Shah (2002) "Effect of Degree, Type, and Position of Unsaturation on the $pK_a$ of Long-Chain Fatty Acids" *J Colloid and Interface Science*, 256:201-207.
Karasu et al., "Practice Guideline for the Treatment of Patients with Major Depressive Disorder," Second Edition, Apr. 2000, 78 pages.
KATHON™ CG, Rohm and Haas Personal Care, Jun. 2006, 9 pages.
Kaur et al., "Formulation Development of Self Nanoemulsifying Drug Delivery System (SNEDDS) of Celecoxib for Improvement of Oral Bioavailability," Pharmacophore, 2013, 4(4):120-133.
Kim, "Stability of Minoxidil in Aqueous Solution", Yakhak Hoechi, 1986, 30(5):228-231 (English Abstract).
Kinnunen and Hannuksela, "Skin reactions to hexylene glycol," Contact Dermatitis, Sep. 1989, 21(3):154-158.
Kircik, L.H. and S. Kumar (2010 Aug) "Scalp Psoriasis" *J Drugs Dermatol*, 9(8 Suppl):s101-s137.

Kleber et al., "Practice Guideline for the Treatment of Patients with Substance Use Disorders," Aug. 2006, 276 pages.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Knight et al., "Topical diltiazem ointment in the treatment of chronic anal fissure," Br. J. Surg., 2001, 88(4):553-556.
Koerber, "Humectants and Water Activity," Water Activity News, 2000, 8 pages.
Kreuter, "Nanoparticles and microparticles for drug and vaccine delivery," J. Anat., 1996, 189:503-505.
Kucharekova et al., "Effect of a lipid-rich emollient containing ceramide 3 in experimentally induced skin barrier dysfunction," Contact Dermatitis, Jun. 2002, 46:331-338.
Kumar et al., "Application of Broad Spectrum Antiseptic Povidone Iodine as Powerful Action: A Review," Journal of Pharmaceutical Science and Technology, 2009, 1(2):48-58.
Kwak et al. "Study of Complete Transparent Nano-Emulsions which Contain Oils." IFSCC Conference, Seoul Korea, Sep. 2003, 3 pages.
Laboratory 6—Characteristics of Surfactants and Emulsions, retrieved on Jan. 29, 2010, http://web.archive.org/web/20000106225413/http://pharmacy.wilkes.edu/kibbeweb/lab7.html, 5 pages.
Lautenschlager, "A Closer Look on Natural Agents: Facts and Future Aspects," Kosmetic Konzept Kosmetische Praxis, 2006, 5:8-10.
Le Vine et al., "Components of the Goeckerman Regimen," Journal of Investigative Dermatology, 1979, 73:170-173.
Lebwohl and Ali, "Treatment of psoriasis. Part 1. Topical therapy and phototherapy," J. Am Acad Dermatol, Oct. 2001, 487-498.
Lebwohl et al., "A randomized, double-blind, placebo-controlled study of clobestasol propionate 0.05% foam in the treatment of nonscalp psoriasis," International Journal of Dermatology, 2002, 41(5): 269-274.
Lee et al., "Historical review of melanoma treatment and outcomes," Clinics in Dermatology, 2013, 31: 141-147.
Lee et al., "The Stabilization of L-Ascorbic Acid in Aqueous Solution and Water-in-Oil-in-Water Double Emulsion by Controlling pH and Electrolyte Concentration," J. Cosmet. Sci., Jan./Feb. 2004, 55:1-12.
Leive et al., "Tetracyclines of various hydrophobicities as a probe for permeability of *Escherichia coli* outer membrane," Antimicrobial Agents and Chemotherapy, 1984, 25:539-544.
Leunapon-F, Leuna-Tenside, Screenshot, retrieved on Sep. 18, 2015, http://www.leuna-tenside.de/2006_7_14_3143/2006_8_7 5750/2006_8_7 241/cas-68439-49-6, 1 page.
Leung and Robinson, "Bioadhesive Drug Delivery," American Chemical Society, 1991, Chapter 23, 350-366.
Li et al., "Solubility Behavior of Imiquimod in Alkanoic Acids", Pharmaceutical Research, Abstract 3029, Nov. 1997,14(11):5475, 2 pages.
Licking Vaginal Dryness Without a Prescription, retrieved on Dec. 14, 2008, http://www.estronaut.com/a/vag.sub.--dryness.htm, 3 pages.
Lin et al., "Ferulic acid stabilizes a solution of vitamins c and e and doubles its photoprotection of skin," J Invest Dermatol, 2005, 125:826-832.
Lippacher et al., "Liquid and Semisolid SLN Dispersions for Topical Application: Rheological Characterization," European Journal of Pharmaceutics and Biopharmaceutics, 2004, 58:561-567.
Livingstone and Hubel, "Segregation of form, color, movement, and depth: Anatomy, physiology, and perception," Science, May 1988, 240:740-749.
Lupke and Kemper, "The HET-CAM Test: An Alternative to the Draize Eye Test," FD Chem. Toxic., 1986, 24:495-196.
Lupo, "Antioxidants and Vitamins in Cosmetics", Clinics in Dermatology, 2001, 19:467-473.
Luviquat Polymer Grades, BASF The Chemical Company, May 2012, 32 pages.
Mailer, "Chemistry and quality of olive oil," NSW Dept. of Primary Industries, Aug. 2006, Primefact 227, 1-4.
Martindale: The Complete Drug Reference, 33rd Edition, Jun. 2002, Pharmaceutical Press, pp. 1073 and 1473.

(56) References Cited

OTHER PUBLICATIONS

Martindale: The Complete Drug Reference, Thirty-third edition, Bath Press, London, 2002, 1073 and 1473.
Martindale: The Extra Pharmacopoeia, Twenty-eighth edition, The Pharmaceutical Press, London, 1982, 862-864.
Material Safety Data Sheet, Luvitol EHO, Caelo, Nov. 28, 2013, 4 pages.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Safety Data Sheet, Dimethyl Ether, Airgas, May 14, 2015, 12 pages.
Material Safety Data Sheet, Hydroxyethyl Cellulose, Sigma-Aldrich, Jan. 14, 2004, http://terpconnect.umd.edu/~choi/MSDS/Sigma-Aldrich/HYDROXYETHYL%20CELLULOSE, 5 pages.
Material Safety Data Sheet, Hydroxyethyl Cellulose, Sigma-Aldrich, Jan. 2004, 5 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Material Safety Data Sheet, N-Butane, Airgas, May 7, 2015, 13 pages.
Material Safety Data Sheet, Nitrous Oxide, Airgas, Feb. 11, 2016, 11 pages.
Material Safety Data Sheet, Propane, Airgas, Oct. 20, 2015, 12 pages.
Material Safety Data Sheet, Science Lab.com, Polyethylene Glycol 200, MSDS, Nov. 6, 2008, 6 pages.
Material Safety Data Sheet, USP, Progesterone, Apr. 26, 2006, 5 pages.
Mead, "Electrostatic Mechanisms Underlie Neomycin Block of the Cardiac Ryanodine Receptor Channel (RyR2)," Biophysical Journal, 2004, (87): 3814-3825.
Messenger et al., "Minoxidil: Mechanisms of Action on Hair Growth", British Journal of Dermatology, 2004, 150:186-194.
Metronidazole (Veterinary—Systemic), The United States Pharmacopeial Convention, 2007, retrieved on Sep. 10, 2009, www.usp.org/pdf/EN/veterinary/metronidazole.pdf, 4 pages.
Metz et al., "A Phase I Study of Topical Tempol for the Prevention of Alopecia Induced by Whole Brain Radiotherapy," Clinical Cancer Research, Oct. 2004, 10:6411-6417.
Meucci et al., "Ascorbic Acid Stability in Aqueous Solutions", Acta Vitaminol Enzymol, 1985, 7(3-4):147-153 (English Abstact).
Milton, D.T. et al. (2006) "A Phase I/II Study of Weekly High-Dose Erlotinib in Previously Treated Patients With Nonsmall Cell Lung Cancer" Cancer, 107:1034-1041.
Mineral Oil USP, U.S. Department of Health & Human Services, Chemical Abstracts Service Registry No. 8012-95-1, 2011, 7 pages.
Minocycline (DB01017), Drug Bank, Feb 8, 2013, retrieved on Aug. 15, 2013, <http://www.drugbank.ca/drugs/DB01017>, 10 pages.
Minocycline, Wikipedia, the free encyclopedia, retrieved on Oct. 21, 2011, http://en.wikipedia.org/wiki/Minocycline, 7 pages.
MMP Inc., International Development and Manufacturing, "Formulating specialties," retrieved on Feb. 2, 2010, http://mmpinc.com, 3 pages.
Molan, "World Wide Wounds: Honey as a topical antibacterial agent for treatment of infected wounds," Dec. 2001, retrieved May 7, 2008, http://www.worldwidewounds.com/2001/november/Molan/honey-as-topical-agent.html, 13 pages.
Molins PLC v. Textron Inc., 48 F.3d 1172, 33 USPQ2d 1823 (Fed. Cir. 1995), 19 pages.
Morgan et al., "Enhanced Skin Permeation of Sex Hormones with Novel Topical Spray Vehicles," Journal of Pharmaceutical Sciences, Oct. 1998, 87(10):1213-1218.
Mousse, Merriam-Webster Online Dictionary, retrieved on Dec. 8, 2008, http://www.merriam-webster.com/dictionary/mousse, 2 pages.
Musial, W. and A. Kubis (2004) "Carbopols as factors buffering triethanolamine interacting with artificial skin sebum" Polim Med, 34(4):17-30 (Abstract).
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neutrogena Clinical SPF 30 Facial Lifting Wrinkle Treatment, Apr. 28, 2010, retrieved on Sep. 11, 2010, http://www.cosmetoscope.com/2010/04/neutrogea-clinical-with-johnson-johnsons-cytomimic-techology/, 5 pages.
Neves et al., "Rheological Properties of Vaginal Hydrophilic Polymer Gels," Current Drug Delivery, 2009, 6:83-92.
New Nanomaterials to Deliver Anticancer Drugs to Cells Developed, Science Daily, Jun. 2007, retrieved on Oct. 14, 2013, <URL: http://www.sciencedaily.com/releases/2007/06/070607112931.htm>, 3 pages.
Nietz, "Molecular orientation at surfaces of solids," J. Phys. Chem., 1928, 32(2): 255-269.
Niram Chemicals, Chemical products—Cetostearyl Alcohol, Cetyl Alcohol, Stearyl Alcohol and Polyethylene Glycol Importer & Supplier, retrieved on Jul. 17, 2012, http://www.indiamart.com/niramchemicals/chemicals.html, 7 pages.
Novartis "LAMISIL®" Product Information, T2001-29 [online]. Retrieved from: http://www.fda.gov/downloads/Drugs/DrugSafety/PostmarketDrugSafetyInformationforPatientsandProviders/ucm052213.pdf; Published: Apr. 2001, 8 pages.
Oh et al., "Antimicrobial activity of ethanol, glycerol monolaurate or lactic acid against Listeria moncylogenes," Int. J. Food Microbiology, 1993, 20:239-246.
Olsen et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, Nov. 2007, 57:767-774.
OM-Cinnamate, MakingCosmetics.com, retrieved on Sep. 26, 2009, http://www.makingcosmetics.com/sunscreens/OM-Cinnamate-pl 02.html, 1 page.
Omega-9 Fatty Acids (Oleic Acid), Orthomolecular.org, Dec. 2004, retrieved on Aug. 15, 2014, http://orthomolecular.org/nutrients/omega9.html, 1 page.
Optimization of Nano-Emulsions Production by Microfluidization, European Food Research and Technology. Sep. 2007, 22:5-6 (English Abstract).
Oranje et al., "Topical retapamulin ointment, 1%, versus sodium fusidate ointment, 2%, for impetigo: a randomized, observer-blinded, noninferiority study," Dermatology, 2007, 215(4):331-340.
Osborne and Henke, "Skin Penetration Enhancers Cited in the Technical Literature," Pharm. Technology, Nov. 1997, 21(11):58-86.
Padhi et al., "Phospho-olivines as positive-electrode materials for rechargeable lithium batteries," J. Electrochemical Soc., Apr. 1997, 144(4): 1188-1194.
Padi and Kulkarni, "Minocycline prevents the development of neuropathic pain, but not acute pain: possible anti-inflammatory and antioxidant mechanisms," Eur J. Pharmacol, 2008, 601:79-87.
Pakpayat et al., "Formulation of Ascorbic Acid Microemulsions with Alkyl Polyglycosides", European Journal of Pharmaceutics and Biopharmaceutics, 2009, 72:444-452.
Palamaras and Kyriakis, "Calcium antagonists in dermatology: a review of the evidence and research-based studies," Derm. Online Journal, 2005, 11(2):8.
Passi et al., "Lipophilic antioxidants in human sebum and aging," Free Radical Research, 2002,36(4):471-477.
Pharmaceutical Benefits Advisory Committee (PBAC) of Australia. PBAC Public Summary Document—Nov. 2014 Meeting (5 pages).
Pendergrass et al., "The shape and dimension of the human vagina as seen in three-dimensional vinyl polysiloxane casts," Gynecol Obstet. Invest., 1996, 42(3):178-82 (Abstract).
Penreco, "Intelligent Gel Technology Product Specifications," Rev. Jun. 2016 (2 pages).
Permethrin (Insecticide), Wildpro, retrieved on Jun. 4, 2015, http://wildpro.twycrosszoo.org/S/00Chem/ChComplex/perm.htm, 5 pages.

(56) References Cited

OTHER PUBLICATIONS

Perotti et al., "Topical Nifedipine With Lidocaine Ointment vs. Active Control for Treatment of Chronic Anal Fissure," Dis Colon Rectum, 2002, 45(11):1468-1475.
Polystyrene, Wikipedia the free encyclopedia, retrieved Apr. 21, 2014, http://web.archive.org/web/20060312210423/http://en.wikipedia.org/wiki/Polystyrene, 4 pages.
PPG-40-PEG-60 Lanolin Oil, Environmental Working Group, 2010, retrieved on May 19, 2010, http://www.cosmeticsdatabase.com/ingredient/722972/PPG-40-PEG-60_Lanolin_Oil/?ingred06.722972., 3 pages.
Prevent, The American Heritage Dictionary of the English Language, 2007, retrieved on Oct. 9, 2010, http://www.credoreference.com/entry/hmdictenglang/prevent, 1 page.
Product Data Sheet for Meclocycline, bioaustralis fine chemicals** Jun. 28, 2013, 1 page.
PROMIUS™ Pharma LLC (2012) Scytera™ (coal tar) Foam, 2%. Product Information Sheet, 1 page.
Prud'Homme et al., Foams: theory, measurements and applications, Marcel Dekker, Inc., 1996, 327-328.
Purcell, "Natural Jojoba Oil Versus Dryness and Free Radicals," Cosmetics and Toiletries Manufacture Worldwide, 1988, 4 pages.
Purdy et al., "Transfusion-transmitted malaria: unpreventable by current donor exclusion guidelines?" Transfusion, Mar. 2004, 44:464.
Raschke et al., "Topical Activity of Ascorbic Acid: From In Vitro Optimization to In Vivo Efficacy", Skin Pharmacology and Physiology, Jul./Aug. 2004, 17(4):200-206 (Abstract).
Ravet et al., "Electroactivity of natural and sythetic triphylite," J. Power Sources, 2001, 97-98: 503-507.
Raymond, "Iodine as an Aerial Disinfectant," J. Hygiene, May 1946, 44(5):359-361.
Reaction Rate, Wikipedia, the free encyclopedia, retrieved on Dec. 18, 2011, en.wikipedia.org/wiki/Reaction_rate, 6 pages.
Receptacle, Merriam Webster, retrieved on Jul. 12, 2011, http://www.merriam-webster.com/dictionary/receptacle, 1 page.
Refina, "Viscosity Guide for Paints, Petroleum & Food Products," accessed Mar. 4, 2015, http://www.refina.co.uk/webpdfs/info_docs/Viscosity_guide_chart.pdf, 2 pages.
Regulation (EC) No. 2003/2003 of the European Parliament and of the Council, Official Journal of the European Union, Oct. 13, 2003, 2 pages.
Repa et al. "All-trans-retinol is a ligand for the retinoic acid receptors," Proc. Natl. Acad Sci, USA, Aug. 1993, 90: 7293-7297.
Reregistration Eligibility Decision for Pyrethrins, EPA, Jun. 7, 2006, 108 pages.
Richwald, "Imiquimod", Drugs Today, 1999, 35(7):497 (Abstract).
Rieger and Rhien, "Emulsifier Selection/HLB," Surfactants in Cosmetics, 129, 1997.
Rohstoffinformationen, Hoffmann Mineral, 2008, 8 pages (with English translation).
Rosacea, Clinuvel Pharmaceuticals, 2010, retrieved on Sep. 9, 2010, http://clinuvel.com/skin-conditions/common-skin-conditions/rosacea#h0-6-prevention, 5 pages.
Rowe et al., "Glyceryl Monooleate," Handbook of Pharmaceutical Excipients, 2011, 10 pages, retrieved on Dec. 19, 2011, http://www.medicinescomplete.com/mc/excipients/current/1001938996.htm?q=glyceryl%20monooleate&t=search&ss=text&p=l# hit.
Rowe et al., "Octyldodecanol," Handbook of Pharmaceutical Excipients, 2011, 9 pages, retrieved on Dec. 19, 2011, URL:http://www.medicinescomplete.com/mc/excipients/current/1001942450.htm?q=octyldodecanol&t=search&ss=text&p=l# hit.
Rowe et al., "Sucrose Palmitate," Handbook of Pharmaceutical Excipients, 2011, 11 pages, retrieved on Dec. 19, 2011, URL:http://www.medicinescomplete.com/mc/excipients/current/EXP-TD-c46-mn0001.htm?q=sucrose%20stearate&t=search&ss=text&p=l# hit.
Rowe et al., "Sucrose Stearate," Handbook of Pharmaceutical Excipients, 2011, 11 pages, retrieved on Dec. 19, 2011, URL:http://www.edicinescomplete.com/mc/excipients/current/EXP-TD-cll-mnOOOI-mnOOOI.htm?q=sucrose%20stearate&t=search&ss=text&p=3# hit.
RSES (Oil in Refrigerator Systems, Service Application Manual, 2009).
Rutledge, "Some corrections to the record on insect repellents and attractants," J. Am. Mosquito Control Assoc, Dec. 1988, 4(4): 414-425.
Sakai et al., "Characterization of the physical properties of the stratum corneum by a new tactile sensor," Skin Research and Technology, Aug. 2000, 6:128-134.
Sanders et al., "Stabilization of Aerosol Emulsions and Foams," J. Soc. Cosmet. Chem., 1970, 21:377-391.
Sarpotdar, P.P. et al. (Jan. 1986) "Effect of Polyethylene Glycol 400 on the Penetration of Drugs Through Human Cadaver Skin in Vitro" J Pharma Sci, 75(1):26-28.
Savin et al., "Tinea versicolor treated with terbinafine 1% solution," Int J. Dermatol, Nov. 1999; 38(11): 863-865.
Schaefer, "Silicone Surfactants," Tenside Surf. Det., 1990, 27(3): 154-158.
Schmidt, "Malassezia furfur: a fungus belonging to the physiological skin flora and its relevance in skin disorders," Cutis, Jan. 1997, 59(1):21-24 (Abstract).
Schmolka, "A review of block polymer surfactants," Journal of the American Oil Chemists Society, Mar. 1977, 54: 110-116.
Schott, "Rheology," Remington's Pharmaceutical Sciences, 17th Edition, 1985, 330-345.
Schutze, "Iodine and Sodium Hypochlorite as Wound Disinfectants," The British Medical Journal, 1915, 921-922.
Sciarra, "Aerosol Technology," *Kirk-Othmer Encyclopedia of Chemical Technology*, Jul. 2012, 20 pages.
Scientific Discussion for the Approval of Aldara, EMEA, 2005, 10 pages.
Scott, "A Practical Guide to Equipment Selection and Operating Techniques," Pharmaceutical Dosage Forms: Disperse Systems, vol. 3, Copyright 1998, 291-362.
Scully et al., "Cancers of the oral mucosa treatment and management," Medscape Drugs, Diseases and Procedures, Apr. 20, 2012, retrieved on Oct. 12, 2013, <http://emedicine.medscape.com/article/1075729-treatment>, 10 pages.
Seborrheic Dermatitis, retrieved on Sep. 9, 2010, http://www.cumc.columbia.edu/student/health/pdf/R-S/Seborrhea%20Dermatitis.pdf, 2 pages.
Security Datasheet, Luvitol EHO, Cetearyloctanoat, Nov. 27, 2013, 10 pages.
Sehgal, " Ciclopirox: a new topical pyrodonium antimycotic agent: A double-blind study in superficial dermatomycoses," *British Journal of Dermatology*, 1976, 95:83-88.
Sharp, "Oil," Dictionary of Chemistry, Copyright 1990, 286.
Shear et al., "Pharmacoeconomic analysis of topical treatments for tinea infections," Pharmacoeconomics, Mar. 1995, 7(3):251-267.
Shear, Vocabulary.com, retrieved on Aug. 23, 2013, <URL: https://www.vocabulary.com/dictionary/shear>, 3 pages.
Sheer, Vocabulary.com, retrieved on Aug. 23, 2013, https://www.vocabulary.com/dictionary/sheer, 3 pages.
Shemer, A. et al. (2016) "Topical minocycline foam for moderate to severe acne vulgaris: Phase 2 randomized double-blind, vehicle-controlled study results" J Am Acad Dermatol, 74(6):1251-1252.
Sheu et al., "Effect of Tocopheryl Polyethylene Glycol Succinate on the Percutaneous Penetration of Minoxidil from Water/Ethanol/Polyethylene Glycol 400 Solutions," Drug Dev. Ind. Pharm., Jun. 2006, 32(5):595-607 (Abstract).
Shim et al., "Transdermal Delivery of Mixnoxidil with Block Copolymer Nanoparticles," J. Control Release, Jul. 2004, 97(3):477-484 (Abstract).
Shrestha et al., "Forming properties of monoglycerol fatty acid esters in nonpolar oil systems," Langmuir, 2006, 22: 8337-8345.
Sigma-Aldrich. http://www.sigmaaldrich.com/catalog/product/sial/p1754?lang=en® ion=. Published:Mar. 5, 2014.
Sigma Aldrich, "Surfactants Classified by HLB Numbers" 2017 [online]. Retrieved from the Internet: www.sigmaaldrich.com/materials-science/material-science-products.html?TablePage=22686648, on Jul. 8, 2017 (3 pages).
Silicone, Oxford Dictionaries Online, retrieved on Apr. 19, 2011, http://www.oxforddictionaries.com/definition/silicone?view=uk, 1 page.

(56) References Cited

OTHER PUBLICATIONS

Simoni et al., "Retinoic acid and analogs as potent inducers of differentiation and apoptosis. New promising chemopreventive and chemotherapeutic agents in oncology," Pure Appl Chem., 2001, 73(9):1437-1444.
Simovic et al., "The influence of Processing Variables on Performance of O/W Emulsion Gels Based on Polymeric Emulsifier (Pemulen ®TR-2NF)," International Journal of Cosmetic Science, Dec. 2001, 21(2)119-125 (Abstract).
Smith, "Hydroxy acids and skin again," Soap Cosmetics Chemical Specialties, Sep. 1993, 69(9):54-59.
Smith, "Sore Nipples," Breastfeeding Mom's Sore Nipples / Breastfeeding Basics, retrieved on Feb. 8, 2012, http://breastfeedingbasics.com/articles/sore-nipples, 9 pages.
Softemul-165: Product Data Sheet, Mohini Organics PVT LTD, retrieved Apr. 10, 2014, http://www.mohiniorganics.com/Softemul165.html#, 1 page.
Solans et al., "Overview of basic aspects of microemulsions," Industrial Applications of Microemulsions, New York, 1997, 1-17.
SOLODYN® (Minocycline HCI, USP) Prescribing Information; revised Jun. 2016, 2 pages.
Sonneville-Aubrun et al., "Nanoemulsions: A New Vehicle for Skincare Products," Advances in Colloid and Interface Science, 2004, 108-109:145-149.
Spa Collections, AG & Co. Essential oil workshop, retrieved on Jan. 31, 2010, http://www.agworkshop.com/p3.asp, 1 page.
Squillante et al., "Codiffusion of propylene glycol and dimethyl isosorbide in hairless mouse skin," European J. Pharm. Biopharm., 1998, 46:265-271.
Squire and Goode, "A randomized, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat., Jun. 2002, 13(2):51-60 (Abstract).
Sreenivasa et al., "Preparation and Evaluation of Minoxidil Gels for Topical Application in Alopecia," Indian Journal of Pharmaceutical Sciences, 2006, 68(4):432-436.
Sreenivasan, B. et al. (1956)"Studies on Castor Oil. I. Fatty Acid Composition of Castor Oil" *J Am Oil Chem Soc*, 33:61-66.
Stehle et al., "Uptake of minoxidil from a new foam formulation devoid of propylene glycol to hamster ear hair follicles," J. Invest. Dermatol., 2005, 124(4): A101 (Abstract).
Sugisaka et al., "The Physicochemical Properties of Imiquimod, The First Imidazoquinoline Immune Response Modifier", Pharmaceutical Research, Nov. 1997, 14(11):5475, Abstract 3030.
*Sun Pharmaceutical Industries Ltd.* v. *Eli Lilly and Co.*, 611 F.3d 1381, 95 USPQ2d 1797 (Fed. Cir. 2010),7 pages.
Sung, J.H. et al. (2010) "Gel characterisation and in vivo evaluation of minocycline-loaded wound dressing with enhanced wound healing using polyvinyl alcohol and chitosan" *Intl J Pharmaceut*, 392:232-240.
Surfactant, Wikipedia, the free encyclopedia, retrieved on Oct. 24, 2010, http://en.wikipedia.org/wiki/Surfactant, 7 pages.
Tadros, "Surfactants in Nano-Emulsions." Applied Surfactants: Principles and Applications, 2005, 285-308.
Tamarkin, D. (2013) "Foam: A Unique Delivery Vehicle for Topically Applied Formulations" in: *Formulating Topical Applications—a Practical Guide*. Dayan N, Ed., Carol Stream, IL: CT Books, Chapter 9, pp. 233-260.
Tan et al., "Effect of Carbopol and PolyvinYlpyrrolidone on the Mechanical, Rheological, and Release Properties of Bioadhesive Polyethylene Glycol Gels," AAPS PharmSciTech, 2000; 1(3) Article 24, 10 pages.
Tanhehco, "Potassium Channel Modulators as Anti-Inflammatory Agents", Expert Opinion on Therapeutic Patents, Jul. 2001, 11(7):1137-1145 (Abstract).
Tarumoto et al., "Studies on toxicity of hydrocortisone 17-butyrate 21-propionate-1. Acute toxicity of hydrocortisone 17-butyrate 21-propionate and its analogues in mice, rats and dogs (author's transl)," J Toxicol Sci., Jul. 1981, 6:1-16 (Abstract).
Tata et al., "Penetration of Minoxidil from Ethanol Propylene Glycol Solutions: Effect of Application Volume on Occlusion," Journal of Pharmaceutical Sciences, Jun. 1995, 84(6):688-691.
Tata et al., "Relative Influence of Ethanol and Propylene Glycol Cosolvents on Deposition of Minoxidil into the Skin," Journal of Pharmaceutical Sciences, Jul. 1994, 83(10):1508-1510.
Tavss et al., "Anionic detergent-induced skin irritation and anionic detergent-induced pH rise of bovine serum albumin," *J. Soc. Cosmet. Chem.*, Jul./Aug. 1988, 39:267-272.
TCI America, Safety Data Sheet; Product Name: Squalane. Product Code: H0096 [online]. Retrieved from: https://www.spectrumchemical.com/MSDS/TCI-H0096.pdf. Revised: Oct. 6, 2014, 5 pages.
Tea Tree Oil, LookChem, Chemical Abstract No. 68647-73-4, 2012, 2 pages.
The HLB System—A Time-Saving Guide to Emulsifier Selection, ICI Americas Inc., Mar. 1980, 1-22.
The United States Pharmacopeia: The National Formulary, USP23/NF18, US Pharmacopoeia, Jan. 1995, p. 10-14.
Third Party Submission in Published Patent Application, U.S. Appl. No. 12/014,088, dated Feb. 4, 2009, 4 pages.
Thorgeirsdottir et al., "Antimicrobial activity of monocaprin: a monoglyceride with potential use as a denture disinfectant," Acta Odontologica Scandinavica, Feb. 2006, 64:21-26 (Abstract only).
Tirumala et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
Tjulandin, S. et al. (2013) "Phase I, dose-finding study of AZD8931, an inhibitor of EGFR (erbB1), HER2 (erbB2) and HER3 (erbB3) signaling, in patients with advanced solid tumors" *Invest New Drugs*, 32(1):145-153.
Todd et al., "Volatile Silicone Fluids for Cosmetic Formulations," Cosmetics and Toiletries, Jan. 1976, 91:27-32.
Torma et al., "Biologic activities of retinoic acid and 3, 4-Didehydroretinoic acid in human keratinocytes are similar and correlate with receptor affinities and transactivation properties," J. Invest. Dermatology, 1994, 102: 49-54.
Torres-Rodriguez, "New topical antifungal drugs," Arch Med Res., Winter 1993, 24(4): 371-375 (Abstract).
Toxicology and Carcinogenesis Studies of T-Butyl Alcohol (CAS No. 75-65-0) IN F344/N Rats and B6C3F1 Mice (Drinking Water Studies), May 1995, retrieved on Dec. 9, 2008, http://ntp.niehs.nih.gob/?objectid-0709F73D-A849-80CA-5FB784E86613576D1, 4 pages.
Trofatter, "Imiqimod in clinical practice", European Journal of Dermatology, Oct./Nov. 1998, 8(7 Supp.):17-19 (Abstract).
Tsai et al., "Drug and Vehicle Deposition from Topical Applications: Use of In Vitro Mass Balance Technique with Minoxidil Solutions", J. Pharm. Sci., Aug. 1992, 81(8):736-743 (Abstract).
Tsai et al., "Effect of Minoxidil Concentration on the Deposition of Drug and Vehicle into the Skin," International Journal of Pharmaceutics, 1993, 96(1-3):111-117 (Abstract).
Tsai et al., "Influence of Application Time and Formulation Reapplication on the Delivery of Minoxidil through Hairless Mouse Skin as Measured in Franz Diffusion Cells," Skin Pharmacol., 1994, 7:270-277.
Tyring, "Immune-Response Modifiers: A New Paradigm in the Treatment of Human Papillomavirus," Current Therapeutic Research, Sep. 2000, 61(9):584-596 (Abstract).
Tzen et al. "Surface Structure and Properties of Plant Seed Oil Bodies," Department of Botany and Plant Sciences, University of California, Riverside, California 92521, Apr. 15, 1992, 9 pages.
Tzen et al., "Lipids, proteins and structure of seed oil bodies from diverse species," Plant Physiol., 1993, 101:267-276.
U.S. Final Office Action for U.S. Appl. No. 11/430,437, Tamarkin et al., dated Dec. 16, 2008, 24 pages.
U.S. Office Action for U.S. Appl. No. 11/430,437, Tamarkin et al., dated May 9, 2008, 27 pages.
U.S. Office Action from U.S. Appl. No. 11/430,599, dated Jul. 28, 2008, 59 pages.

(56) References Cited

OTHER PUBLICATIONS

Uner et al., "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel," Pharmazie, 2005, 60:751-755.
United States Standards for Grades of Olive Oil and Olive-Pomace Oil, United States Dept. of Agriculture, Oct. 25, 2010, 21 pages.
Valenta, "Effects of Penetration Enhancers on the In-vitro Percutaneous Absorption of Progesterone," J. Pharm. Pharmacol., 1997, 49: 955-959.
Van Cutsem et al., "The anti-inflammatory effects of ketoconazole," J. Am. Acad. Dermatol., Aug. 1991, 25(2):257-261.
Van Slyke, "On the measurement of buffer values and on the relationship of buffer value to the dissociation constant of the buffer and the concentration and reaction of the buffer solution," J. Biol. Chem., 1922, 52:525-570.
Vera et al., "Scattering optics of Foam," Applied Optics, Aug. 20, 2001, 40(24):4210-4214.
Veron et al., "Stability of Minoxidil Topical Formulations", Ciencia Pharmaceutica, 1992, 2(6):411-414 (Abstract).
View of NCT01171326 on Dec. 7, 2010, ClinicalTrials.gov archive, Dec. 7, 2010, retrieved on Sep. 9, 2013, http://clinicaltrials.gov/archive/NCT01171326/2010_12_07, 4 pages.
View of NCT01362010 on Jun. 9, 2011, ClinicalTrials.gov archive, Jun. 9, 2011, retrieved on Sep. 9, 2013, < http://clinicaltrials.gov/archive/NCT01362010/2011_06_09>, 3 pages.
Wang and Chen, "Preparation and surface active properties of biodegradable dextrin derivative surfactants," Colloids and Surfaces A: Physicochemical and Engineering Aspects, 2006, 281(1-3):190-193.
Water Jel Technologies, "Material Safety Data Sheet for Neomycin Antibiotic Ointment," Dec. 1, 2004, 7 pages.
WebMD (2014) "Psoriasis Health Center" [online]. Retrieved Apr. 13, 2015; retrieved from the Internet: http://www.webmd.com/skin-problems-and-treatments/psoriasis/psoriasis-symptoms, 3 pages.
WebMD (2014) "Understanding Rosacea—the Basics" [online]. Retrieved Apr. 13, 2015; retrieved from the Internet: http://www.webmd.com/skin-problems-and-treatments/understanding-rosacea-basics (5 pages).
WebMD (2017) "User Reviews & Ratings—Scytera topical" [online]. Retrieved Mar. 1, 2017; retrieved from the Internet: http://www.webmd.com/drugs/drugreview-151502-Scytera+topical.aspx?drugid=151502&drugname=Scytera+topical&sortby=3 (2 pages).
Weindl et al., "Hyaluronic acid in the treatment and prevention of skin diseases: molecular biological, pharmaceutical and clinical aspects," Skin Pharmacology and Physiology, 2004, 17: 207-213.
Wenninger et al., "International Cosmetic Ingredient Dictionary and Handbook," The Cosmetic, Toiletry, and Fragrance Association, Washington, DC., 1997, vol. 1, 4 pages.
Wermuth, "Similarity in drugs: reflections on analogue design," Drug Discovery Today, Apr. 2006, 11(7/8):348-354.
What Is CP Serum, Skin Biology, retrieved on Dec. 1, 2008, http://web.archive.org/web/20030810230608/http://www.skinbio.com/cpserum.-html, 21 pages.
What Is TSC?, Tuberous Sclerosis Alliance, Jan. 1, 2005, retrieved on Feb. 6, 2014, http://www.tsalliance.org.pages.aspx?content=2, 3 pages.
Williams et al., "Acne vulgaris," Lancet, 2012, 379:361-372.
Williams et al., "Scale up of an olive/water cream containing 40% diethylene glycol monoethyl ether," Dev. Ind. Pharm., 2000, 26(1):71-77.
Williams et al., "Urea analogues in propylene glycol as penetration enhancers in human skin," International Journal of Pharmaceutics, 1989, 36, 43-50.
Wormser et al., "Protective effect of povidone-iodine ointment against skin lesions induced by sulphur and nitrogen mustards and by non-mustard vesicants," Arch. Toxicol., 1997, 71, 165-170.
Wormser, "Early topical treatment with providone-iodine ointment reduces, and sometimes prevents, skin damage following heat stimulus," Letter to the Editor, Burns, 1998, 24:383.
Wrightson, W.R. et al. (1998) "Analysis of minocycline by high-performance liquid chromatography in tissue and serum" *J Chromatography B*, 706:358-361.
Wu et al., "Interaction of Fatty Acid Monolayers with Cobalt Nanoparticles," Nano Letters, 2004, 4(2): 383-386.
Yamada et al., "Candesartan, an angiotensin II receptor antagonist, suppresses pancreatic inflammation and fibrosis in rats," J. Pharmacol. Exp. Ther., 2003, 307(1)17-23.
Zeichner, J.A. (2010) "Use of Topical Coal Tar Foam for the Treatment of Psoriasis in Difficult-to-treat Areas" *J Clin Aesthet Dermatol*, 3(9):37-40.
Zinc Oxide, Knovel, 2006, retrieved on Apr. 18, 2012, http://www.knovel.com/web/portal/knovel_content?p_p_id=EXT_KNOVEL_CONTENT . . . , 2 pages.
Ziolkowsky, "Moderne Aerosolschaume in der Kosmetik (Modern Aerosol Foams in Chemical and Marketing Aspects)" Seifen-Ole-Fette-Wachse, Aug. 1986, 112(13): 427-429 (with English translation).

Patient 120
Baseline

Patient 120
Day 3

Patient 120
EOT

METHOD FOR HEALING OF AN INFECTED ACNE LESION WITHOUT SCARRING

CROSS REFERENCE TO RELATED APPLICATIONS

This application is a continuation of U.S. patent application Ser. No. 13/831,396, filed Mar. 14, 2013, which claims the benefit of priority under 35 U.S.C. § 119(e) to U.S. Provisional Application No. 61/611,232, filed Mar. 15, 2012, U.S. Provisional Application No. 61/748,603, filed Jan. 3, 2013, U.S. Provisional Application No. 61/780,074, filed Mar. 13, 2013, and U.S. Provisional Application No. 61/779,953 filed Mar. 13, 2013; and is a continuation in part application of:

1) U.S. patent application Ser. No. 13/499,501, filed Sep. 10, 2012, which is a 371 of International Patent Application No. PCT/IB2010/02612 filed Oct. 1, 2010, which claims the benefit of priority under 35 U.S.C. § 119(e) to U.S. Provisional Application No. 61/248,144, filed Oct. 2, 2009, U.S. Provisional Application No. 61/322,148, filed Apr. 8, 2010, U.S. Provisional Application No. 61/349,911, filed May 31, 2010, U.S. Provisional Application No. 61/385,385, filed Sep. 22, 2010, U.S. Provisional Application No. 61/331,126, filed May 4, 2010, and U.S. Provisional Application No. 61/380,568 filed Sep. 7, 2010;

2) U.S. patent application Ser. No. 13/499,727, filed Sep. 10, 2012, which is a 371 of International Patent Application No. PCT/IB2011/01374, filed May 4, 2011, International Patent Application No. PCT/IB2010/002617, filed Oct. 1, 2010, International Patent Application No. PCT/IB2010/002612, filed Oct. 1, 2010, and International Patent Application No. PCT/IB/2010/002613 filed Oct. 1, 2010, which claims the benefit of priority under 35 U.S.C. § 119(e) to U.S. Provisional Application No. 61/388,884, filed Oct. 1, 2010, U.S. Provisional Application No. 61/385,385, filed Sep. 22, 2010, U.S. Provisional Application No. 61/380,568, filed Sep. 7, 2010, U.S. Provisional Application No. 61/349,911, filed May 31, 2010, and U.S. Provisional Application No. 61/331,126, filed May 4, 2010;

3) U.S. patent application Ser. No. 13/100,724, filed May 4, 2011, which is a continuation in part application of: A) International Application No. PCT/IB2010/002612, filed Oct. 1, 2010, which claims the benefit of priority to U.S. Provisional Application No. 61/248,144, filed Oct. 2, 2009, U.S. Provisional Application No. 61/322,148, filed Apr. 8, 2010, U.S. Provisional Application No. 61/349,911, filed May 31, 2010, U.S. Provisional Application No. 61/385,385, filed Sep. 22, 2010, U.S. Provisional Application No. 61/331,126, filed May 4, 2010, U.S. Provisional Application No. 61/388,884, filed Oct. 1, 2010, and U.S. Provisional Application No. 61/380,568, filed Sep. 7, 2010; B) U.S. patent application Ser. No. 13/100,724, filed May 4, 2011, which is a continuation in part application of International Application No. PCT/IB2010/002617, filed Oct. 1, 2010, which claims the benefit of priority to United States Provisional Application No. 61/248,144, filed Oct. 2, 2009, U.S. Provisional Application No. 61/322,148, filed Apr. 8, 2010, U.S. Provisional Application No. 61/349,911, filed May 31, 2010, U.S. Provisional Application No. 61/385,385, filed Sep. 22, 2010, U.S. Provisional Application No. 61/331,126, filed May 4, 2010, U.S. Provisional Application No. 61/388,884, filed Oct. 1, 2010 and U.S. Provisional Application No. 61/380,568 filed Sep. 7, 2010; and C) U.S. patent application Ser. No. 13/100,724, filed May 4, 2011, which is a continuation in part application of International Application No. PCT/IB2010/002613, filed Oct. 1, 2010, which claims the benefit of priority to U.S. Provisional Application No. 61/248,144 filed, Oct. 2, 2009, U.S. Provisional Application No. 61/322,148, filed Apr. 8, 2010, U.S. Provisional Application No. 61/349,911, filed May 31, 2010, U.S. Provisional Application No. 61/385,385, filed Sep. 22, 2010, U.S. Provisional Application No. 61/331,126, filed May 4, 2010, U.S. Provisional Application No. 61/388,884, filed Oct. 1, 2010, and U.S. Provisional Application No. 61/380,568, filed Sep. 7, 2010;

4) U.S. patent application Ser. No. 13/499,475, filed Sep. 14, 2012, which is a 371 of International Patent Application No. PCT/IB2010/002617, filed Oct. 1, 2010, which claims the benefit of priority under 35 U.S.C. § 119(e) to U.S. Provisional Application No. 61/248,144, filed Oct. 2, 2009, U.S. Provisional Application No. 61/322,148, filed Apr. 8, 2010, U.S. Provisional Application No. 61/349,911, filed May 31, 2010, U.S. Provisional Application No. 61/385,385, filed Sep. 22, 2010, U.S. Provisional Application No. 61/331,126, filed May 4, 2010, U.S. Provisional Application No. 61/380,568, filed Sep. 7, 2010, and U.S. Provisional Application No. 61/388,884, filed Oct. 1, 2010; and 5) U.S. patent application Ser. No. 13/499,709 filed Sep. 10, 2012, which is a 371 of International Patent Application No. PCT/IB2010/002613, filed Oct. 1, 2010, and claims the benefit of priority under 35 U.S.C. § 119(e) to U.S. Provisional Application No. 61/248,144, filed Oct. 2, 2009, U.S. Provisional Application No. 61/322,148, filed Apr. 8, 2010, U.S. Provisional Application No. 61/349,911, filed May 31, 2010, U.S. Provisional Application No. 61/385,385, filed Sep. 22, 2010, U.S. Provisional Application No. 61/331,126, filed May 4, 2010, U.S. Provisional Application No. 61/380,568, filed Sep. 7, 2010, and U.S. Provisional Application No. 61/388,884, filed Oct. 1, 2010; all of which are herein incorporated in their entirety by reference.

BACKGROUND

Impetigo, a highly contagious bacterial infection of the superficial layers of the epidermis, is a common childhood disorder but can also be found amongst adults. It is a very common bacterial skin infection and one of the most common skin diseases among children, accounting for about 10% of skin diseases treated in US pediatric clinics. The bacteria held responsible are *Staphylococcus aureus* and *Streptococcus pyogenes*, or often a combination of the two. Impetigo is usually transmitted by direct contact but fomites also play an important role. Methicillin-resistant *S. aureus* (MRSA) is being found with increasing frequency.

Impetigo has three clinical varieties: impetigo contagiosa (common impetigo), bullous impetigo, and ecthyma. Features of all three types of impetigo, however, may coexist in any individual patient.

A number of topical compositions containing pharmaceutically active ingredients are known in the art for the treatment of impetigo. Topical mupirocin 2% (Bactroban ointment and cream) is a treatment option, as are older treatments, such as topical gentian violet and vioform. For many patients, mupirocin is a viable treatment option for MRSA, however, resistance of bacteria to mupirocin has been widely reported. More recent data have shown that topical fusidic acid 2% (Fucidin cream) is useful for impetigo, and is thought to be equally as effective as mupirocin.

Retapamulin 1% (Altabax ointment), recently approved by the FDA, is a drug in the new class of pleuromutilin antibiotics for the topical treatment of impetigo due to *Staphylococcus aureus* (methicillin-susceptible only) or *Streptococcus pyogenes*.

In clinical trials, retapamulin and mupirocin were administered for a whole week, three times a day thus making it burdensome for caregivers of the impetigo patients, who are frequently infants and young children, so a product that requires less applications would be advantageous and could improve patient compliance.

The vehicles for both retapamulin and mupirocin are ointments. Ointments are thick pastes, which are relatively difficult to apply and spread on skin, result in a greasy and sticky appearance, and are usually not appealing for use, especially in facial treatments. Compliance with ointments is usually relatively poor, because when applied they require rubbing onto the infected wound leading to pain and transfer of infectious organisms to other sites. Furthermore, when ointments containing petroleum are applied onto a wound, metabolic products and excreta from the wound cannot be easily removed because of the difficulty of passing through the hydrophobic petroleum barrier. In addition, an active drug ingredient, which is dissolved or dispersed in the petroleum carrier, is likely not efficiently absorbed into the wound tissue, thus, the efficacy of the drug is affected. Another example is ophthalmologic ointments, which are applied into the eye, and make the eye area sticky and uncomfortable. Moreover, in a physiological aspect, petroleum restricts respiration of the wound tissue and disturbs to the normal respiration of the skin.

Therapeutic topical compositions must stay on the skin for a sufficient period of time to allow the active agent to be absorbed onto the skin; to perform its activity; to also remain there in a preventative role; they must not irritate the skin; and they must be perceived by the patient as pharmaceutically convenient in order to achieve sufficient patient compliance. By "pharmaceutically convenient", it is meant that the skin look and feel to the patient is good, i.e., it must not be too watery or too greasy and it must easily be applied.

Tetracycline antibiotics, such as tetracycline, oxytetracycline, demeclocycline, doxycycline, lymecycline, meclocycline, methacycline, minocycline, rolitetracycline, chlorotetracycline and tigecycline, are extremely unstable compounds and are sensitive to many formulation excipients (for example, water, short chain alcohols, certain polymers, certain hydrophilic solvents and surfactants). Thus, most tetracyclines, e.g., minocycline and doxycycline, currently exist only in solid oral dosage forms or are given by injection or infusion.

Oral antibiotics (e.g., antistaphylococcal penicillins, amoxicillin/clavulanate [Augmentin], cephalosporins, macrolides) are effective for the treatment of impetigo; erythromycin is less effective. (C Cole and J Gazewood, Diagnosis and Treatment of Impetigo *Am Fam Physician.* 2007 Mar. 15; 75(6):859-864.)

Regardless, a seven-day course of oral antibiotics is usually recommended for symptoms to clear up but they can be associated with a variety of side effects which inter alia may include stomach ache, nausea, vomiting, diarrhea, and the appearance of yeast infections, such as thrush (Candidiasis), a fungal infection of the mucous membranes.

Furthermore, oral tetracycline antibiotics are generally not used in the treatment of impetigo, primarily because they are prohibited for use in young children due to the ability to cause tooth discoloration. Common side effects of oral minocycline include diarrhea, dizziness, drowsiness, indigestion, lightheadedness, loss of appetite, nausea, sore mouth, throat or tongue, and vomiting. Minocycline may also cause severe side effects, including severe allergic reactions, bloody stools, blurred vision, change in the amount of urine produced, fever, chills, sore throat, hearing problems, joint pain, muscle pain or weakness, rectal or genital irritation, red, swollen, blistered, or peeling skin, ringing in the ears, seizures, severe or persistent headache, severe skin reaction to the sun, watery diarrhea, stomach cramps or pain, swollen glands, symptoms of pancreatitis, trouble swallowing, unusual bruising or bleeding, unusual tiredness or weakness, vaginal irritation or discharge, white patches in the mouth and yellowing of the skin or eyes. Due to these side effects, the FDA added oral minocycline in 2009 to its Adverse Event Reporting System (AERS), a list of medications under investigation by the FDA for potential safety issues.

Minocycline has a spectrum of activity and a mode of action similar to that of tetracycline but it is more active against many species including *Staphylococcus aureus*, streptococci, *Neisseria meningitidis*, various enterobacteria, *Acinetobacter, Bacteroides, Haemophilus, Nocardia*, and some mycobacteria, including *M. leprae.* Partial cross-resistance exists between minocycline and other tetracyclines but some strains resistant to other drugs of the group remain sensitive to minocycline, perhaps because of better cell-wall penetration. Minocycline is a tetracycline derivative with uses similar to those of tetracycline. Minocycline is given orally or by injection or infusion. It is also a component of multidrug regimens for the treatment of leprosy and has been used in the prophylaxis of meningococcal infection to eliminate the carrier state, but the high incidence of vestibular disturbances, presumeably resulting from it being given systemically, means that it is not the drug of choice for the latter. It has neuroprotective properties, it is being investigated for motor neurone disease, and for the management of Huntington's chorea. It is used in the treatment of rheumatoid arthritis and in the prevention or treatment of various skin disorders, including acne.

Due to the broad spectrum of antibacterial activity of tetracycline antibiotics, especially minocycline and doxycycline, topical treatment comprising tetracycline compositions, which can reduce adverse systemic exposure of such antibiotics is warranted.

Novel, stable, patient-friendly topical hydrophobic therapeutic breakable gel and foamable compositions comprising tetracycline, without surfactants, have been described, for example in U.S. application Ser. Nos. 13/499,501, 13/499,727, 13/499,475, and 13/499,709, U.S. Publication No. 2011/0281827, WO11/039637, WO11/039638, WO 11/138678 and WO 2011/064631 all of which are herein incorporated in their entirety by reference.

The instability of minocycline was observed and confirmed in a compatibility study with pharmaceutical excipients described, for example, in WO11/039637. The study identified and demonstrated different hydrophilic solvents that were incompatible with minocycline and different hydrophobic solvents, emollients and waxes that revealed compatibility with minocycline. Fatty alcohols, as well as some fatty acids (such as stearic acid, oleic acid and palmitic acid) were found to be compatible with minocycline. Additionally, a few certain surfactants (e.g., sucrose fatty esters) and some additives (aerosil and menthol) were disclosed to be compatible with minocycline, whereas other surface active agents including polysorbates, sorbitan esters of fatty acids, polyoxyethylene alkyl ethers and polyoxyethylene esters of fatty acids were found not to be compatible.

It was further discovered, for example, in WO11/039637 that addition of water caused rapid degradation of minocycline and addition of antioxidants (alpha-tocopherol, BHA/BHT and propyl gallate) did not prevent such degradation. Furthermore, compatible excipients became incompatible in the presence of water and addition of antioxidants did not remedy this result. It was also shown, for example, in WO11/039637 that minocycline has activity that decreases apoptosis and increases cell viability.

It was further found, for example, in WO11/039637, in in-vitro skin delivery studies that enhanced penetration was achieved without the need of adding a hydrophilic solvent and thus degradation of minocycline could be further reduced or prevented. Minocycline was found to have been delivered intradermally at sufficient levels to treat skin infections but did not pass through the skin transdermally and therefore topical application should be essentially free from adverse systemic effects.

Wound is an injury to the body (as from violence, accident, or surgery) that typically involves laceration or breaking of a membrane (as the skin) and usually damage to underlying tissues (Merriam Webster Dictionary). Burns are injuries to tissues caused by heat, friction, electricity, radiation, or chemicals. Wounds and burns are often colonized by microbiologic pathogens, including Gram-positive bacteria, such as *Staphylococcus aureus* and/or *Streptococcus pyogenes*; and Gram-negative bacteria, e.g., *Pseudomonas aeruginosa*.

Despite the very common occurrence of skin infections, only a limited number of topical antibiotics are approved for the treatment of wounds and particularly infected wounds. Mupirocin (Bactroban, GSK) is an antibiotic, developed by GSK. Emerging resistance to mupirocin is becoming a concern. In coagulase-negative staphylococci isolates, mupirocin resistance rates are higher, ranging from 12.7% in Europe to 38.8% in the United States. Retapamulin (Altabax, GSK) is another topical antibiotic used for wound treatment. Fucidin (LEO Pharma) is effective in primary and secondary skin infections caused by sensitive strains of *S. aureus, Streptococcus* species and *C. minutissimum*, but is virtually inactive against Gram-negative bacteria.

These three products require 6-10 days of treatment to attain clinical improvement. For example, Altabax attained 85.6% clinical success after 7 days, vs. 52.1% effect of the respective placebo.

Additionally, the above products are available as ointments, which when applied require rubbing onto the lesion, which is frequently an infected wound, leading to pain and transfer of infectious organisms to other sites. An additional drawback of Bactroban and Fucidin is that they require treatment three times daily, which imposes inconvenience to the caregivers of the impetigo patients, who are mostly infants and young children, so a product that requires less applications is advantageous and likely to improve compliance.

Acne, including acne vulgaris and acne-rosacea (also termed "rosacea") are skin diseases which involve infected lesions, including non-inflammatory and inflammatory lesions. Non-inflammatory acne lesions include blackheads (open comedones) and whiteheads (closed comedones). Open and closed comedones along with papules and pustules are referred to as papulopustular acne, a form of inflammatory acne. The more severe the disease is, it involves more infected, inflammatory lesions. Nodular acne is the most severe form of inflammatory acne. If improperly treated, inflammatory acne lesions can produce deep scarring.

SUMMARY

In one or more embodiments there is provided a method of treating or alleviating a disorder comprising administering topically at least once daily for at least three days to a target area on a subject having the disorder a hydrophobic gel or foam composition comprising a tetracycline antibiotic wherein the target area comprises an area of skin, mucosa, or eye.

In one or more embodiments the disorder is selected from the group consisting of a wound, a chronic wound, a burn, impetigo, acne, rosacea, an inflammation, an ulcer, and a skin disease caused by a bacteria. In an embodiment the disorder is a wound. In an embodiment the disorder is a chronic wound. In an embodiment the disorder is a burn. In an embodiment the disorder is impetigo. In an embodiment the disorder is acne. In an embodiment the disorder is rosacea. In an embodiment the disorder is an inflammation. In an embodiment the disorder is an ulcer. In an embodiment the disorder is a skin disease caused by a bacteria. In an embodiment the disorder is a skin disease caused by a fungus. In an embodiment the disorder is a skin disease caused by a virus.

In one or more embodiments there is provided a method of treating or alleviating a disorder selected from the group consisting of impetigo, acne, rosacea, and a skin disease caused by a bacteria, comprising administering topically at least once daily for at least three days to a target area on a subject having the disorder a hydrophobic gel or foam composition comprising a tetracycline antibiotic wherein the target area comprises an area of skin, mucosa, or eye.

In one or more embodiments there is provided a method of restoring or accelerating the restoration of the integrity of an area of broken skin or mucosa comprising administering topically at least once daily for at least three days to a target area on a subject comprising an area of broken skin or mucosa, a hydrophobic gel or foam composition comprising a tetracycline antibiotic.

In one or more embodiments there is provided a method of restoring skin integrity or accelerating the restoration of the integrity of an area of broken skin or mucosa comprising administering topically a hydrophobic gel or foam composition comprising a tetracycline antibiotic at least once daily for at least three days to a target area on a subject comprising an area of broken skin or mucosa or an area of skin containing a skin lesion.

In one or more embodiments there is provided a hydrophobic gel or foam composition comprising a tetracycline antibiotic, for use in the restoration of skin integrity or acceleration of the restoration of the integrity of an area of a skin or mucosal lesion comprising a broken skin or a damaged mucosa, by topical application of the gel or foam composition to said skin or mucosal lesion, wherein the gel or foam composition consists of a carrier comprising about 60% to about 99% by weight of at least one hydrophobic oil.

In one or more embodiments there is provided hydrophobic gel or foam composition comprising a tetracycline antibiotic, for use in the restoration of skin integrity or acceleration of the restoration of the integrity of an area of broken skin or mucosa by topical application of the gel or foam composition to a target area on a subject comprising an area of broken skin or mucosa or an area of skin containing a skin lesion, wherein the gel or foam composition consists of a carrier comprising about 60% to about 99% by weight of at least one hydrophobic oil.

It has now surprisingly been found, that the topical administration of a gel or a foamable composition comprising a minocycline provided effective drug delivery to an infected lesion site, leading to rapid clinical improvement of impetigo within three days of treatment.

It has also surprisingly been found, that the topical administration of a gel or a foamable composition comprising a minocycline provided restoration of skin integrity and acceleration of restoration of skin integrity, leading to rapid clinical improvement within three days of treatment and return to skin integrity within seven days.

In addition, side effects were not observed. Topical treatment appears to avoid known side effects common to the oral minocycline treatment route. Thus, topical administration may act to prevent or minimize side effects. It has also been surprisingly found that the topical administration of a gel or foamable composition comprising minocycline was effective in curing MRSA patients in comparison to current topical medications for impetigo. Moreover, it did so expeditiously. The compositions provided herein comprising minocycline were effective with only a twice daily application, thereby leading to better patient compliance compared to available treatment options. The compositions were also able to treat lesions that produced exudate and to reduce or eliminate exudate. In the course of treatment the compositions were able to reduce symptoms and severity of impetigo. Moreover, the topical administration of gel or foamable compositions comprising minocycline demonstrated a residual effect non-existent in current topical medications for impetigo. Thus, it has been shown that topical foamable compositions containing minocycline offer a safe, user friendly, and effective alternative to current oral minocycline treatments.

It has surprisingly been established that gel and foamable compositions comprising tetracycline antibiotics can effectively treat impetigo successfully using only a twice or once daily topical application regime to an area infected while avoiding unwanted systemic side effects commonly to oral treatment with antibiotics like minocycline.

It has surprisingly been established that a short course of treatment using topical minocycline is sufficient to achieve surprising clinical results in the treatment of infected wounds:

1. Quick onset of clinical effect: 80% of the patients improved after 3 days of treatment.
2. Clinical success is achieved in 100% of the patients.
3. All MRSA infections were cured following 7 days of treatment.
4. Skin healing/skin structure correction: In many of the patients the wounds disappeared and the skin structure returned to normal within 3-7 days
5. No scar formation was noted, despite the accelerated healing of the wounds.

It is further surprising that such results were not associated with any drug related side effects.

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

In one or more embodiments, there is provided a method of treating or alleviating a disorder selected from the group consisting of impetigo, acne, rosacea, and a skin disease caused by a bacteria, comprising administering topically at least once daily for at least three days to a target area on a subject having the disorder a hydrophobic gel or foam composition comprising a tetracycline antibiotic wherein the target area comprises an area of skin, mucosa, or eye, and wherein said administration of hydrophobic gel or foam composition restores or accelerates the restoration of the integrity of the target area.

In one or more embodiments, there is provided a method of treating a wound or a burn, comprising the steps of:

(a) providing a therapeutically effective amount of a therapeutic hydrophobic breakable composition consisting of a carrier comprising about 60% to about 99% by weight of at least one hydrophobic oil; and a tetracycline antibiotic, suspended in the carrier; and (b) applying the therapeutic substance at least once to outer surface of a wound or a burn;

wherein the duration of treatment is such that an improvement of the wound or the burn is attained within 7 days of application.

BRIEF DESCRIPTION OF THE DRAWINGS

The invention is described with reference to the drawings, which are presented for the purpose of illustration only and is not intended to be limiting of the invention. In one or more embodiments.

DETAILED DESCRIPTION

Figure 1:
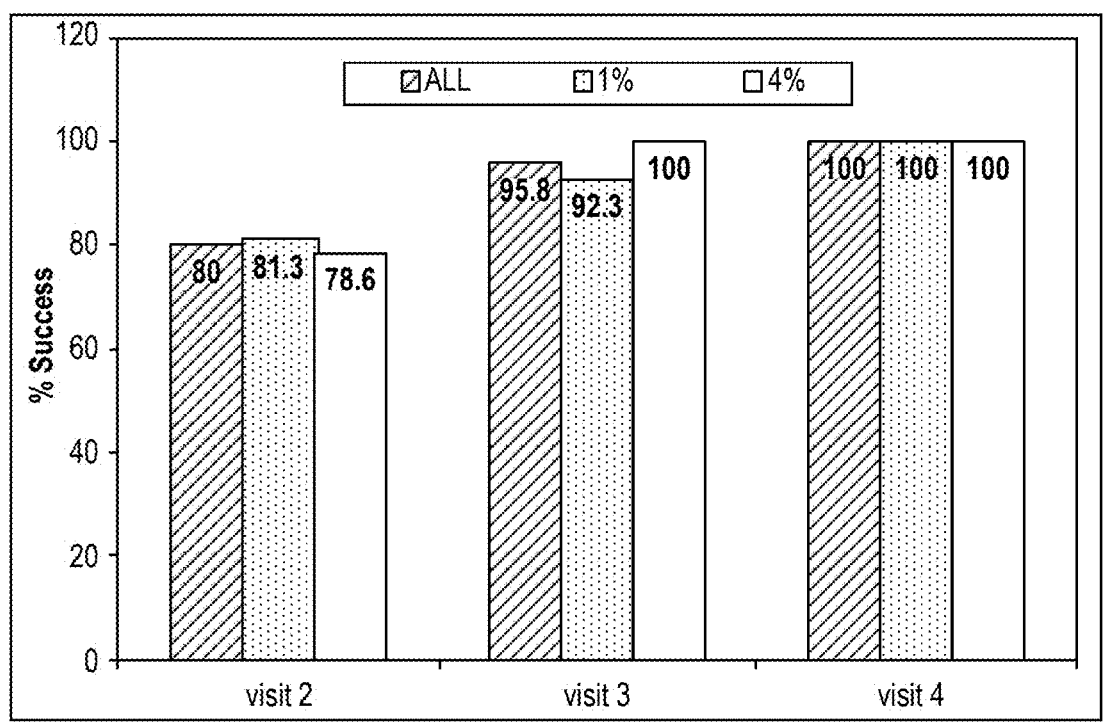
FIG. 1 provides a chart summarizing the clinical response rates in the PPC population by visit.

In one or more embodiments there is provided herein, a method for treating a disorder of the skin or a mucosal surface, especially when the disorder is rosacea, acne and/or impetigo. The method includes administering topically to a surface having the disorder a therapeutic hydrophobic composition, consisting of a carrier comprising about 60% to about 99% by weight of at least one hydrophobic solvent; at least one viscosity-modifying agent selected from the group consisting of a fatty alcohol, a fatty acid, and a wax; and a tetracycline antibiotic.

According to one or more embodiments provided herein the tetracycline is a minocycline, which is a semi-synthetic tetracycline antibiotic. The drug is usually bacteriostatic in action. It can exert its antimicrobial activity by inhibiting protein synthesis. It can also have an antiviral effect. According to one or more embodiments the minocycline is minocycline hydrochloride (minocycline HCl). Minocycline hydrochloride is a yellow crystalline powder that is sparingly soluble in water, slightly soluble in alcohol and practically insoluble in chloroform and in ether. Preparations of minocycline hydrochloride have an acid pH and incompatibility may reasonably be expected with alkaline preparations or with drugs unstable at low pH.

Minocycline is known to be highly sensitive to air and light and undergoes rapid degradation. Therefore storage of foamable formulations in airtight sealed containers under pressure with propellant may contribute to preserving stability subject to selection of compatible canisters and accessories. Likewise, production and or filing under vacuum in an oxygen free environment can help.

The ingredients of the carrier were selected for their compatibility with tetracycline antibiotics as described. It was not sufficient to identify single ingredients that were compatible but formulations had to be found in which the ingredients in combination were also compatible.

In one or more embodiments, a hydrophobic foamable composition or gel provided herein comprises:
a) about 60% to about 99% by weight of at least one hydrophobic solvent;
b) about 1% to about 22% by weight of at least one viscosity modifying agent; and
c) about 0.1% to about 18% of a tetracycline antibiotic (e.g., minocycline HCl).

In one or more embodiments, a hydrophobic foamable composition or gel provided herein comprises:
a) about 70% to about 90% by weight of at least one hydrophobic solvent;
b) about 10 to about 22% by weight of at least one viscosity modifying agent; and
c) about 0.5% to about 8% of a tetracycline antibiotic (e.g., minocycline HCl).

In one or more embodiments, a hydrophobic foamable composition or gel provided herein comprises:
a) about 75% to about 90% by weight of at least one hydrophobic solvent;
b) about 10 to about 22% by weight of at least one viscosity modifying agent; and
c) about 0.5% to about 2% of a tetracycline antibiotic (e.g., minocycline HCl).

In one or more embodiments, a hydrophobic foamable composition or gel provided herein comprises:
a) about 72% to about 88% by weight of at least one hydrophobic solvent;
b) about 10 to about 22% by weight of at least one viscosity modifying agent; and
c) about 2% to about 6% of a tetracycline antibiotic (e.g., minocycline HCl).

According to one or more embodiments there are provided substantially surfactant-free oleaginous formulations comprising a tetracycline, such as a minocycline for use in treatment of rosacea and impetigo. In one or more embodiments the tetracycline acts to reduce oxidative stress and or inflammation in skin pathologies. In one or more embodiments the tetracycline is effective where the condition is accompanied by apoptotic cell death.

Definitions

All % values are provided on a weight (w/w) basis.

By the term "about" herein it is meant that a figure or range of figures can vary plus or minus up to 10%. So in this embodiment if a figure of "about 1" is provided then the amount can be up to 1.1 or from 0.9. As will be appreciated by one of the art there is some reasonable flexibility in formulating compositions such that where one or more ingredients are varied successful formulations may still be made even if an amount falls slightly outside the range. Therefore, to allow for this possibility amounts are qualified by about. In one or more other embodiments the figures may be read without the prefix about.

The term "thixotropic," as used herein, means that the formulation shows a decrease in viscosity upon application of shear force. The structure of the formulation breaks down, leading to a reduction in viscosity. When the formulation is standing without shear force, this decrease in viscosity is recovered over time.

It should be noted that the term "gel" means a jelly-like material that can have properties ranging from soft and fluid to hard and tough. Gels may be in liquid, semi-liquid, semi-solid or solid state. Solid gels are defined as a substantially diluted crosslinked system, which exhibits no flow when in the steady-state. By weight, gels are mostly liquid, yet they behave like semi-solids due to a three-dimensional crosslinked network of a solidifying, gelling or thickening agent within the liquid. It is the crosslinks within the fluid that give a gel its structure (hardness) and contribute to stickiness (tack). Depending on the amounts of gelling agent in a formulation the gel may be semi-solid with some limited flowability, such that when the semi-solid gel is placed in a tube and is inclined horizontally from a vertical position it will slowly flow from the vertical towards the horizontal or it may be a liquid gel where the amount of gelling agent or gelling effect is lower such that the gel structure or connections are weaker or loose so that when placed in a tube and tilted from a vertical position to the horizontal the gel readily flows and adapts to the horizontal position. The rheological properties of gels at different surface temperatures can influence the release and bioabsorption of drugs therefrom.

In some embodiments, formulations comprising a hydrophobic oil and viscosity-modifying agents demonstrated increased viscosity of such oil, and to which when even small amounts of a suspended tetracycline antibiotic were added, a substantial or synergistic increase in the viscosity of the composition was observed.

In one or more embodiments, the gel is stable and it retains its viscosity upon dispensing from a container, such as a tube, yet, it liquefies and spreads easily upon application of shear force, which can be mild, such as a simple rub. Further, while the gel is oily, it absorbs into the site of application, such as the skin or mucosa membrane, and after minutes the surface does not appear and or feel significantly oily or greasy.

The term "liquid gel" refers inter alia to the formulation after propellant is added (which prior to adding the propellant is a gel) or where the gel is loose or fluid or such that when subjected to gravity will pour or become liquid.

The term "waterless" or "water free" as used herein, means that the composition contains no, or essentially no, free or unassociated or absorbed water. Similarly, "substantially water free" or "substantially waterless" carriers contain at most incidental or trace amounts of water. In one or more embodiments, "substantially waterless" or substantially water free" means the composition contains about or less than 1%, about or less than 0.8%; about or less than 0.6%; about or less than 0.4%; about or less than 0.2%; about or less than 0.1%, about or less than 0.5%, about or less than 0.1%.

By the term "single phase" herein it is meant that after addition of propellant to the composition or carrier, the liquid components of the foamable composition or carrier are fully miscible, and the solid components, if any, are either dissolved or homogeneously suspended in the composition so that only one phase is visible.

By the term "substantially a single phase" is meant that the composition or carrier after addition of propellant is primarily or essentially a single phase as explained above, but may also have present a small amount of material which is capable of forming or may form a separate phase amounting to less than about 5% of the composition or carrier after the addition of propellant, preferably less than about 3%, and more preferably less than about 1%.

The term "unstable active agent" as used herein, means an active agent which is oxidized and/or degraded within less than a day, and in some cases, in less than an hour upon exposure to air, light, skin or water or a pharmaceutical excipient under ambient conditions.

It should be noted that the term "surfactant" or "emulsifier" in the context herein refers to stand alone surfactants used to reduce surface tension between two substances or phases, which are also capable of stabilizing an emulsion of water and oil. Reduction of surface tension can be significant in foam technology in relation to the ability to create small stable bubbles. This is as opposed to the term surfactant which has often been loosely used in the art to include substances which do not function effectively as standalone surfactants to reduce surface tension between two substances or phases and which are also capable of stabilizing an emulsion of water and oil. For example, a surfactant as provided herein, does not include fatty acids, does not include fatty alcohols and does not include propoxylated lanolin oil derivatives. In the context of the present invention fatty acids and fatty alcohols are defined as foam adjuvants. Similarly, propoxylated lanolin oil derivatives in the context herein are defined as emollients.

"Standard surfactant" or "customary surfactant" or "stand alone surfactant" refers to customary non-ionic, anionic, cationic, zwitterionic, amphoteric and amphiphilic surfactants. Many standard surfactants are derivatives of fatty alcohols or fatty acids, such as ethers or esters formed from such fatty alcohols or fatty acids with hydrophilic moieties, such as polyethylene glycol (PEG). However, a native (non derivatized) fatty alcohol or fatty acid, as well as waxes are not regarded as a standard surfactant.

The term "co-surfactant" as used herein, means a molecule which on its own is not able to form and stabilize satisfactorily an oil in water emulsion but when used in combination with a surfactant the co-surfactant has properties which can allow it to help surfactants to create an emulsion and can boost the stabilizing power or effect of the surfactant. Examples include a fatty alcohol, such as cetyl alcohol or a fatty acid such as stearic acid. Cetyl alcohol is a waxy hydrophobic substance that can be emulsified with water using a surfactant. Some substances may have more than one function and for example, fatty alcohols can in some formulations act as a co-solvent. In certain circumstances, a co-surfactant can itself be converted into a surfactant or soap by, for example, adding a base, such as, triethanolamine to a fatty acid like stearic acid.

The term "viscosity modifying agent" in the context of the present invention is an agent which, when added to a hydrophobic oil, facilitates the creation of a hydrophobic breakable vehicle in the form of a breakable gel or breakable foam. In one or more embodiments the viscosity modifying agent is a "foamer complex" comprising a fatty alcohol, a fatty acid and/or a wax.

The term "breakable" refers to a unique property of the gel or the foam wherein the gel or foam is stable upon dispensing from a container, yet breaks and spreads easily upon application of shear or mechanical force, which can be mild such as a simple rub.

It should be noted that the term a "polyol", as used herein, is an organic substance that contains at least two hydroxy groups in its molecular structure.

The term "water activity" as used herein, represents the hygroscopic nature of a substance, or the tendency of a substance to absorb water from its surroundings. Microorganisms require water to grow and reproduce, and such water requirements are best defined in terms of water activity of the substrate. The water activity of a solution is expressed as $Aw=P/Po$, where P is the water vapor pressure of the solution and Po is the vapor pressure of pure water at the same temperature. Every microorganism has a limiting Aw, below which it will not grow; e.g., for Streptococci, *Klebsiella* spp, *Escherichia coli, Clostridium perfringens*, and *Pseudomonas* spp, the Aw value is 0.95. *Staphylococcus aureus* is most resistant and can proliferate with an Aw as low as 0.86, and fungi can survive at Aw of at least 0.7. In one or more embodiments, the concentration of the hydrophobic solvent, and/or second rheology modulator in the composition is selected to provide an Aw value selected from the ranges between or of (1) about 0.8 and about 0.9; (2) about 0.7 and about 0.8; and (3) less than about 0.7. Delivering the formulation in a pressurized package does not allow for humidity to be absorbed by the preparation, and therefore, the water free character of the composition is not altered.

In an embodiment, no preservative is needed because the formulation is a waterless hydrophobic solvent or oil-based formulation having an Aw (water activity) value of less than 0.9, or less than about 0.8, or less than about 0.7, or less than about 0.6, and preferably less than about 0.5 which is below the level of microbial proliferation.

The identification of a "solvent," as used herein, is not intended to characterize the solubilization capabilities of the solvent for any specific active agent or any other component of the foamable composition. Rather, such information is provided to aid in the identification of materials suitable for use as a part in the foamable composition described herein.

It should be noted that the term "a method of treating a disease or a disorder" as provided throughout the specification is interchangeable with the term "use of the composition as a medicament for treatment of a disease". It should be noted the term a disease is used interchangeably with the term disorder.

It should be noted that the term "substantially free of" an ingredient as provided throughout the specification is intended to mean that the composition comprises less than about 0.5% by weight (e.g., less than about 0.2% by weight, less than about 0.1% by weight, less than about 0.05% by weight, less than about 0.01% by weight, less than about 0.001% by weight, or 0% by weight) of an ingredient.

The term "surfactant free" or emulsifier free" or "non-surfactant" composition means compositions which comprise no or negligible levels of surface active agents. Where a formulation includes insignificant or de minimis amounts of surface active agents it is considered to be essentially surfactant free.

The term "substantially surfactant-free" relates to a composition wherein the ratio between the viscosity-modifying agent and the surfactant is between 10:1 or 5:1; or between 20:1 and 10:1 or between 100:1 and 20:1. In additional embodiments, the term relates to a composition that contains a total of less than about 0.4% of a surfactant selected from the group consisting of customary non-ionic, anionic, cationic, zwitterionic, amphoteric and ampholytic surfactants.

Preferably, the composition comprises less than about 0.2% by weight of a standard surfactant or less than about 0.1%; or less than 0.05%.

By de minimis is meant so minor as to merit disregard.

The term "hydrophobic gel composition" or "hydrophobic foam composition" or "hydrophobic composition" is intended to mean that the composition has a low solubility in water. In an embodiment, 100 to 1000 parts of water are needed to dissolve or render misscible 1 part of composition. In an embodiment, 1000 to 10,000 parts of water are needed to dissolve or render miscible 1 part of composition. In an embodiment, more than 10,000 parts of water are needed to dissolve or render miscible 1 part of composition.

By "regular basis" is meant a repeated or repeatable interval of time which can be by way of illustration, a part of a day, daily, alternate daily, twice weekly, weekly, fortnightly, monthly or some other repeated or repeatable interval for an appropriate period of time wherein a dose is to be applied. In this connection the repeat applications will be according to the needs of the subject and the disease or disorder. In some circumstances as little as three repeat doses may be required in other cases, between 3 and 14, in other cases between 14 and 28, in other cases between 28 and 50, in other cases between 50 and 75, in other cases between 75 and 100 and in other cases such as where prolonged treatment or a long period of maintenance dosing is needed as many as one two or three hundred repeat doses may be needed.

The term safe in the context herein means having no or essentially no systemic or dermal adverse events.

The term tolerable or enhanced tolerability in the context herein means having no or essentially no skin irritation symptoms such as pigmentation, erythema, dryness, peeling and itching.

By "essentially no" in the context of tolerability includes insignificant or de minimis occurrences of skin irritation events manifested in symptoms such as pigmentation, erythema, dryness, peeling and itching or events not connected with the application of topical tetracyclines.

By "essentially no" in the context of safety includes insignificant or de minimis occurrences of systemic or dermal adverse events or events not connected with the application of topical tetracyclines.

The following primary efficacy parameters were used to assess the results of the clinical trial in the present invention were clinical success, bacteriological success and clinical failure as set out and defined in the Altabax study.

Clinical success was defined as a total absence of treated lesions, or if the treated lesions had become dry without crusts, with or without erythema, compared with appearance at baseline, or if the lesions showed improvement (defined as a decrease in the size of the affected area, number of lesions or both).

Clinical success at follow-up was defined as continued absence of the treated lesions, or the treated lesions had become dry without crusts, with or without erythema, compared with baseline, or improvement (defined as EOT above).

Bacteriological success, was determined when the causative pathogen isolated from the target lesion at baseline (*Staphylococcus aureus* and/or *Streptococcus pyogenes* and/or MRSA) was eliminated on culture at EOT or follow-up, or clinical response was such that no exudate material was available for culture, as evidence of pathogen eradication so that no further antimicrobial therapy was necessary. In contrast, bacteriological failure was determined by the non-eradication of the organism from the target lesion that was isolated at baseline.

Clinical failure was defined as insufficient improvement or deterioration (i.e. lesions remained crusted and/or had exudate leaving a yellow or honey-colored crust, or the lesion area had increased from baseline, with or without an increase in the number of lesions) so that additional antibiotic therapy was required.

It should be noted that hydrophobic compositions disclosed herein can be applied to the target site as a gel or a semi-solid gel or a foam. In certain other embodiments, it can be, applied as a liquid gel or as a collapsed foam. In one or more embodiments, the composition is thixotropic. In one or more embodiments, the gel formulation subjected to constant shear rate shows a reduction in viscosity with time. In one or more further embodiments, after the material is allowed to rest for a period of time, the viscosity increases again. In one or more embodiments, there is provided prior to adding propellant a solid or semi-solid composition or gel. In one or more embodiments, the composition or gel is a liquid. In one or more embodiments the propellant is miscible with and dilutes the composition.

Upon packaging of the foamable composition in an aerosol container and adding a propellant, a shakable and homogenous foamable composition, which releases a breakable foam with good to excellent quality is produced. The resulting foam is pharmaceutically equivalent to the respective gel (prior to adding the propellant), since immediately upon dispensing of the foam the propellant evaporates and the composition upon collapsing is similar to or that of the gel. This is an important pragmatic advantage, because many drug development activities, including expensive and lengthy toxicology studies with numerous animals and clinical trials with thousands of patients can be saved by conducting such studies once for either the gel or foam presentation instead of twice (for each presentation).

Application can be, hourly, twelve hourly, daily, alternate-day or intermittent, according to the condition of the patient. For reasons of compliance less frequent applications, where possible are preferable such as daily single applications. In certain cases, where prolonged or long term treatment is required an initial dose is provided followed by a gradual reduction to a lower maintenance dose, which can be increased if further outbreaks occur.

In one or more embodiments, the initial dose of tetracycline is about 18%, or 17.5%, or 16.5%, or 15.5%, or 14.5%, or 13.5% or 12.5%, or 11.5%, or 10.5% or 9.5% or 8.5% or 7.5% or 6.5% or 5.5% or 4.5% or 3.5% or 2.5% or 1.5%, or 17%, or 16%, or 15%, or 14%, or 13% or 12%, or 11%, or 10% or 9% or 8% or 7% or 6% or 5% or 4% or 3% or 2% or 1% or 0.75% or 0.5% or 0.25% or 0.2% by weight of the composition. In one or more embodiments the maintenance dose of tetracycline is about 7.5% or 6.5% or 5.5% or 4.5% or 3.5% or 2.5% or 1.5%, 7% or 6% or 5% or 4% or 3% or 2% or 1% or 0.5%, or 1.9%, or 1.8%, or 1.7%, or 1.6%, or 1.55 or 1.4% or 1.3% or 1.2% or 1.1%, or 0.9% or 0.8%, or 0.7%, or 0.6% or 0.4% or 0.35 or 0.25% or 0.2% or 0.15% or 0.1% by weight of the composition.

In one or more embodiments, such a composition is presented as a breakable gel, which breaks down with mild mechanical force.

In one or more embodiments, the hydrophobic composition when packaged in an aerosol container to which is added a liquefied or compressed gas propellant the composition provides upon release from the container a breakable foam of at least good quality that breaks easily upon application of mechanical force.

In one or more embodiments, the composition is a foamable composition that is thermally stable at skin temperature.

In one or more embodiments, when the above composition is filled into an aerosol can and pressurized with a propellant a foamable composition is produced.

In one or more embodiments, the at least one hydrophobic solvent comprises or is selected from the group consisting of a mineral oil, a hydrocarbon oil, an ester oil, an ester of a dicarboxylic acid, a triglyceride oil, an oil of plant origin, an oil from animal origin, an unsaturated or polyunsaturated oil, a diglyceride, a PPG alkyl ether, an essential oil, a silicone oil, liquid paraffin, an isoparaffin, a polyalphaolefin, a polyolefin, polyisobutylene, a synthetic isoalkane, isohexadecane, isododecane, alkyl benzoate, alkyl octanoate, $C_{12}$-$C_{15}$ alkyl benzoate, $C_{12}$-$C_{15}$ alkyl octanoate, arachidyl behenate, arachidyl propionate, benzyl laurate, benzyl myristate, benzyl palmitate, bis(octyldodecyl stearoyl) dimer dilinoleate, butyl myristate, butyl stearate, cetearyl ethylhexanoate, cetearyl isononanoate, cetyl acetate, cetyl ethylhexanoate, cetyl lactate, cetyl myristate, cetyl octanoate, cetyl palmitate, cetyl ricinoleate, decyl oleate, diethyleneglycol diethylhexanoate, diethyleneglycol dioctanoate, diethyleneglycol diisononanoate, diethyleneglycol diisononanoate, diethylhexanoate, diethylhexyl adipate, diethylhexyl malate, diethylhexyl succinate, diisopropyl adipate, diisopropyl dimerate, diisopropyl sebacate, diisosteary dimer dilinoleate, diisostearyl fumarate, dioctyl malate, dioctyl sebacate, dodecyl oleate, ethylhexyl palmitate, ester derivatives of lanolic acid, ethylhexyl cocoate, ethylhexyl ethylhexanoate, ethylhexyl hydroxystarate, ethylhexyl isononanoate, ethylhexyl palmytate, ethylhexyl pelargonate, ethylhexyl stearate, hexadecyl stearate, hexyl laurate, isoamyl laurate, isocetyl behenate, isocetyl lanolate, isocetyl palmitate, isocetyl stearate, isocetyl salicylate, isocetyl stearate, isocetyl stearoyl stearate, isocetearyl octanoate, isodecyl ethylhexanoate, isodecyl isononanoate, isodecyl oleate, isononyl isononanoate, isodecyl oleate, isohexyl decanoate, isononyl octanoate, isopropyl isostearate, isopropyl lanolate, isopropyl laurate, isopropyl myristate, isopropyl palmitate, isopropyl stearate, isostearyl behenate, isosteary citrate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isosteary salicylate, isosteary tartarate, isotridecyl isononanoate, isotridecyl isononanoate, lauryl lactate, myristyl lactate, myristyl myristate, myristyl neopentanoate, myristyl propionate, octyldodecyl myristate, neopentylglycol dicaprate, octyl dodecanol, octyl stearate, octyl palmitate, octyldodecyl behenate, octyldodecyl hydroxystearate, octyldodecyl myristate, octyldodecyl stearoyl stearate, oleyl erucate, oleyl lactate, oleyl oleate, propyl myristate, propylene glycol myristyl ether acetate, propylene glycol dicaprate, propylene glycol dicaprylate, propylene glycol dicaprylate, maleated soybean oil, stearyl caprate, stearyl heptanoate, stearyl propionate, tocopheryl acetate, tocopheryl linoleate, glyceryl oleate, tridecyl ethylhexanoate, tridecyl isononanoate, triisocetyl citrate, alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides, wheat germ oil, PPG-2 butyl ether, PPG-4 butyl ether, PPG-5 butyl ether, PPG-9 butyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-20 butyl ether, PPG-22 butyl ether, PPG-24 butyl ether, PPG-26 butyl ether, PPG-30 butyl ether, PPG-33 butyl ether, PPG-40 butyl ether, PPG-52 butyl ether, PPG-53 butyl ether, PPG-10 cetyl ether, PPG-28 cetyl ether, PPG-30 cetyl ether, PPG-50 cetyl ether, PPG-30 isocetyl ether, PPG-4 lauryl ether, PPG-7 lauryl ether, PPG-2 methyl ether, PPG-3 methyl ether, PPG-3 myristyl ether, PPG-4 myristyl ether, PPG-10 oleyl ether, PPG-20 oleyl ether, PPG-23 oleyl ether, PPG-30 oleyl ether, PPG-37 oleyl ether, PPG-40 butyl ether, PPG-50 oleyl ether, PPG-11 stearyl ether, herring oil, cod-liver oil, salmon oil, cyclomethicone, a dimethyl polysiloxane, dimethicone, an epoxy-modified silicone oil, a fatty acid-modified silicone oil, a fluoro group-modified silicone oil, a methylphenylpolysiloxane, phenyl trimethicone and a polyether group-modified silicone oil. In some embodiments, the hydrophobic solvent comprises or is selected from the group consisting of soybean oil, a coconut oil, a cyclomethicone, a light mineral oil, and mixtures thereof. In one or more embodiments the solvent is tested individually for compatibility with a tetracycline antibiotic and is only used if it passes a compatibility test.

In one or more embodiments, the hydrophobic solvent is at a concentration of about 75% to about 90% by weight. In one or more embodiments, the hydrophobic solvent is at a concentration of at least about 40% by weight, at least about 50% by weight, at least about 60% by weight, at least about 70% by weight, at least about 90% by weight. In some embodiments, the hydrophobic solvent is at a concentration of less than about 90% by weight, less than about 80% by weight, less than about 70% by weight, less than about 60% by weight, less than about 50% by weight.

In one or more embodiments, the viscosity-modifying agent is at a concentration of about 0.1% to about 22%, about 0.4 to about 18%, about 0.5% to 16%, about 0.6% to 14%, about 0.7% to 13%, about 0.8 to about 12%, about 0.9% to about 11%, about 1% to about 10%, about 10% to about 22% by weight. In one or more embodiments, the viscosity-modifying agent is a fatty alcohol having at least 12 carbon atoms in its carbon backbone. In one or more embodiments, the viscosity-modifying agent is a fatty acid having at least 12 carbon atoms in its carbon backbone.

In one or more embodiments, the viscosity-modifying agent is at a concentration of about 9.5% or about 8.5% or about 7.5% or about 6.5% or about 5.5% or about 4.5% or about 3.5% or about 2.5% or about 1.5%, about 7% or about 6% or about 5% or about 4% or about 3% or about 2% or about 1% or about 0.5%, or about 1.9%, or about 1.8%, or about 1.7%, or about 1.6%, or about 1.55 or about 1.4% or about 1.3% or about 1.2% or about 1.1%, or about 0.9% or about 0.8%, or about 0.7%, or about 0.6% or about 0.5% by weight of the composition or less than any of the aforesaid amounts.

In one or more embodiments, the fatty alcohol and/or fatty acid have a melting point of at least about 40° C.

In one or more embodiments, the fatty alcohol comprises or is selected from the group consisting of lauryl alcohol, myristyl alcohol, cetyl alcohol, stearyl alcohol, arachidyl alcohol, behenyl alcohol, tetracosanol, hexacosanol, octacosanol, triacontanol, and tetratriacontanol. In one or more embodiments, the fatty acid comprises or is selected from the group consisting of dodecanoic acid, tetradecanoic acid, hexadecanoic acid, heptadecanoic acid, octadecanoic acid, eicosanoic acid, docosanoic acid, tetracosanoic acid, hexacosanoic acid, heptacosanoic acid, octacosanoic acid, triacontanoic acid, dotriacontanoic acid, tritriacontanoic acid, tetratriacontanoic acid, and pentatriacontanoic acid.

In one or more embodiments, the carbon chain of the fatty alcohol or the fatty acid is substituted with a hydroxyl group.

In one or more embodiments, the fatty acid is 12-hydroxy stearic acid.

In one or more embodiments, the viscosity-modifying agent is a wax comprising or selected from the group consisting of a plant wax, carnauba wax, candelilla wax, ouricury wax, sugarcane wax, retamo wax, jojoba oil, an animal waxes, beeswax, a petroleum derived wax, a paraffin wax, polyethylene, and derivatives thereof.

In one or more embodiments, the viscosity-modifying agent is a combination comprising (i) at least one fatty alcohol and at least one fatty acid; or (ii) at least one fatty alcohol and at least one wax; or (iii) at least one fatty acid and at least one wax; or (iv) at least one fatty alcohol, at least one fatty acid, and at least one wax.

In one or more embodiments the at least one viscosity-modifying agent comprises or is selected from the group consisting of a fatty alcohol, a fatty acid and a wax, wherein the fatty alcohols and/or fatty acids have at least 12 carbon atoms in their carbon backbone. In certain embodiments the viscosity modifying agent is a combination of a fatty alcohol and a fatty acid and or a wax.

Preferably, the fatty alcohol and/or fatty acid and/or wax are solid at ambient temperature. In certain embodiments, the fatty alcohol and/or the fatty acid and/or the wax or the mixture of them have a melting point of more than about 40° C.

Incompatible Excipients and Undesirable Excipients

In certain embodiments, the composition is free of one or more of a petrolatum, surface active agents, protic solvents, certain polar aprotic solvents, isopropyl myristate, polyethylene gelling agents, polyethylene homopolymers, polyethylene copolymers, selenium derivatives and silicone thickening agents; and in certain embodiments, the foamable composition is substantially free of such excipients. In the context herein, the term "substantially-free" relates to a composition that contains a total of less than about 0.4% of a petrolatum, surface active agents, protic solvents, certain polar aprotic solvents isopropyl myristate, polyethylene gelling agents, polyethylene homopolymers, polyethylene copolymers, selenium derivatives and silicone thickening agents cumulatively. Preferably, the composition comprises less than about 0.2% of two or more or all thereof by weight of petrolatum, surface active agents, protic solvents, certain polar aprotic solvents isopropyl myristate, polyethylene gelling agents, polyethylene homopolymers, polyethylene copolymers, selenium derivatives and silicone thickening agents cumulatively or, and more preferably less than about 0.1% individually or of two or more or all thereof cumulatively.

Surface Active Agents

For clarification, in the context herein whilst the term "standard surfactant" or "customary surfactant" refers herein to customary non-ionic, anionic, cationic, zwitterionic, amphoteric and amphiphilic surfactants A fatty alcohol or a fatty acid and certain waxes are not regarded as a standard surfactant. However, in contrast, ethers or esters formed from such fatty alcohols or fatty acids can be regarded as a customary surfactant.

Surfactants of all kinds are undesirable in accordance with the present invention, as (i) they were found to cause degradation of the tetracycline antibiotic; and (ii) they are generally known to possess irritation potential.

Non-limiting examples of classes of non-ionic surfactants that are undesirable according to the present invention include: (i) polyoxyethylene sorbitan esters (polysorbates), such as polysorbate 20, polysorbate 40, polysorbate 60 and polysorbate 80; (ii) sorbitan esters, such as sorbitan monolaurate and sorbitan monooleate; (iii) polyoxyethylene fatty acid esters, such as, PEG-8 stearate, PEG-20 stearate, PEG-40 stearate, PEG-100 stearate, PEG-150 distearate, PEG-8 laurate, PEG-10 laurate, PEG-12 laurate, PEG-20 laurate, PEG-8 oleate, PEG-9 oleate, PEG-10 oleate, PEG-12 oleate, PEG-15 oleate and PEG-20 oleate; (iv) PEG-fatty acid diesters; (v) polyethylene glycol (PEG) ethers of fatty alcohols; (vi) glycerol esters, such as glyceryl monostearate, glyceryl monolaurate, glyceryl monopalmitate and glyceryl monooleate; (vii) PEG-fatty acid mono- and di-ester mixtures; (viii) polyethylene glycol glycerol fatty acid esters; (ix) propylene glycol fatty acid esters; (x) mono- and diglycerides; (xi) sugar esters (mono-, di- and tri-esters of sucrose with fatty acids) and (xii) PEG alkyl phenols.

As mentioned above, in the context of the present invention, while fatty alcohols, fatty acids and certain waxes are somewhat amphiphilic, these substances are not effective as standalone surfactants that can stabilize an emulsion, let alone foamable emulsion compositions, because of their very weak emulsifying capacity and further due to their weak foaming capacity on their own.

They are occasionally used in a supporting role as co-emulsifiers, i.e., in combination with a standard surfactant but are commonly used as thickeners and have successfully been used as foam adjuvants to assist customary surfactants to boost foam quality and stability. For the purposes of forming an emulsion they are usually regarded as an oil and thus have a "required" HLB value for the purpose of determining what standard surfactant might be appropriate to use with the oil phase.

Generally, surfactants are known to possess irritation potential. One way to try and reduce or minimize potential irritation and drying of the skin or mucosa due to surfactants and their repeated use, especially when formulations are to be left on the skin or mucosa rather than being washed off, is to use essentially or primarily nonionic surfactants at significant concentrations although preferably below 5%. The current breakthrough of identifying formulations which produce gels and quality breakable foam yet omitting customary surfactants from a composition may contribute to improved tolerability of such a composition and can be an important advantage. This is especially so when a formulation is to be applied to a very sensitive target site, and particularly so on a repeated basis.

In certain embodiments, the composition is free of customary surfactants, or "surfactant-free" and in certain embodiments the foamable composition is substantially free of customary surfactants, or "substantially surfactant-free".

In certain embodiments, the composition is free or substantially free of an ionic surfactant. In certain embodiments, the composition is free or substantially free of a zwitterionic surfactant. In certain embodiments, the composition is free or substantially free of a non-ionic surfactant.

Protic Solvents

Protic solvents, such as short chain alcohols, glycols and glycerin are incompatible with tetracyclines and therefore are undesirable.

Aprotic Polar Solvents

It was discovered in WO11/039637 that certain polar aprotic solvents are incompatible with tetracycline antibiotics. Thus, aprotic polar solvents, such as dimethyl sulfoxide (DMSO), dimethylformamide (DMF), acetonitrile, acetone, methyl ethyl ketone, 1,4-Dioxane and tetrahydrofuran (THF), N-methylpyrrolidone, pyridine, piperidine, dimethylformanide, Nmethyl-2-pyrrolidone and 1-methyl-2-pyrrolidinone) and azone (1-dodecylazacycloheptan-2-one) are undesirable.

Silicone Thickening Agents

Silicone thickening agents comprise one or more polysiloxane-derived components. Such polysiloxanes are typically cross-linked and they have rubber-like characteristics, which require their solubilization in an oil, usually a silicone oil. An example of such a silicone thickening agent is ST-Elastomer 10 (Dow Corning), which is a mixture of high molecular weight dimethicone crosspolymer (12%), in cyclopentasiloxane (cyclomethicone, silicone solvent). With reference to bioavailability of an active agent in the skin following topical application, it is conceivable that cross co-polymers will create a non-permeable film which should block skin penetration and therefore, it is undesirable. Further, in the context of a breakable foam, cyclomethicone is known as a defoamer and therefore its presence in high concentrations in the breakable hydrophobic composition is undesirable.

In one or more other specific embodiments, the drug carrier is formulated substantially free of elastomers. In one or more other specific embodiments, the drug carrier is formulated essentially free of elastomers. In one or more other specific embodiments, the drug carrier is formulated substantially free of silicones. In one or more other specific embodiments, the drug carrier is formulated essentially free of silicones. In one or more other specific embodiments, the drug carrier is formulated with less than about 30% silicones, or less than about 25% silicones, or less than about 20% silicones, or less than about 15% silicones, or less than about 10% silicones, or less than about 7.5% silicones, or less than about 5% silicones or less than about 2% silicones; or less than about 1% silicones; or less than about 0.5% silicones; or about 1% to about 5% silicones. In one or more other specific embodiments, the drug carrier does not comprise a silicone other than cyclomethicone.

Petrolatum

Petrolatum, also termed "Vaseline", can be disadvantageous, due to its greasy nature. It is known to leave greasy and sticky feeling after application and occasionally stain clothes. Thus, white petrolatum and other semi-solid oils are not a preferred hydrophobic oil according to the present invention. Additionally, compositions containing a substantial amount of semi-solid hydrophobic oils, e.g., white petrolatum, as the main ingredients of the oil phase of the emulsion, will likely exhibit high viscosity and poor flowability and can be inappropriate candidates for a foamable composition. Thus in one or more embodiments, semi-solid hydrophobic oils are a subsidiary component in the composition, for example being present at less than about 45%, at less than about 40%, at less than about 35%, at less than about 30%, at less than about 25%, less than about 20%, less than about 15%, less than about 10%, or less than about 5% by weight of the hydrophobic breakable composition. In an embodiment the claimed formulations are petrolatum free. In another embodiment the formulations have low amounts of petrolatum. By low is meant less than 10%, or less than 8%, or less than 6%, or less than 5%, or less than 4%, or less than 3%, or less than 2%, or less than 1% petrolatum.

Polyol

The identification of a "polyol", as used herein, is an organic substance that contains at least two hydroxy groups in its molecular structure. In one or more embodiments, the polyol is a diol (a compound that contains two hydroxy groups in its molecular structure). Examples of diols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol (e.g., 1,3-butanediol and 1,4-butenediol), butynediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2,56-diol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the polyol is a triol (a compound that contains three hydroxy groups in its molecular structure), such as glycerin, butane-1,2,3-triol, butane-1,2,4-triol and hexane-1,2,6-triol.

In one or more embodiments, the polyol is a saccharide. Exemplary saccharides include, but are not limited to, monosaccharide, disaccharides, oligosaccharides and sugar alcohols.

A monosaccharide is a simple sugar that cannot be hydrolyzed to smaller units.

Empirical formula is $(CH_2O)_n$, and range in size from trioses (=3) to heptoses (n=7). Exemplary monosaccharide compounds are ribose, glucose, fructose and galactose.

Disaccharides are made up of two monosaccharides joined together, such as sucrose, maltose and lactose.

In one or more embodiments, the polyol is a sugar alcohol (also known as a polyol, polyhydric alcohol, or polyalcohol) or a hydrogenated form of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present invention are mannitol, sorbitol, xylitol, maltitol, lactitol. (Maltitol and lactitol are not completely hydrogenated compounds—they are a monosaccharide combined with a polyhydric alcohol.) Mixtures of polyols, including (1) at least one polyol comprises or selected from a diol and a triol; and (2) a saccharide are contemplated within the scope of the present disclosure.

According to some embodiments, the composition is polyol free, i.e. free of polyols.

In other embodiments, the composition is substantially free and comprises less than about 5% final concentration of polyols, preferably less than 2%, more preferably less than 1%. In some embodiments the composition comprises de minimis amounts of polyols. Where a formulation includes insignificant or de minimis amounts of polyols such as less than 0.05% it is considered to be essentially free of them.

In an embodiment, the polyol is linked to a hydrophobic moiety. In the context of the present disclosure, a polyol linked to a hydrophobic moiety is still defined as a "polyol" as long as it still contains two or more free hydroxyl groups.

In an embodiment, the polyol is linked to a hydrophilic moiety. In the context of the present disclosure, a polyol linked to a hydrophilic moiety is still defined "polyol" as long as it still contains two or more free hydroxyl groups.

In one or more embodiments, the hydrophobic composition further contains an anti-infective agent, comprises or selected from the group of an antibiotic agent, an antibacterial agent, an antifungal agent, an agent that controls yeast, an antiviral agent and an antiparasitic agent. In a preferred embodiment, the anti infective agent comprises a tricyclic antibiotic. Not only can combining the anti-infective effect of a hydrophobic composition, with an anti-infective agent can result in a synergistic effect and consequently higher success rate of the treatment but the combination with the viscosity modifying agent achieves a formulation in which the active pharmaceutical ingredient is chemically stable and the formulation is physically stable as demonstrated herein in the Examples. Moreover, the use of hydrophobic based water-free formulation can maximize the antimicrobial and antiviral potentials of the formulations. Delivery topically can be improved by using a hydrophobic carrier with a hydrophobic API. Storage in sealed, light and airtight canisters can assist in preserving the formulations.

In one or more embodiments, the hydrophobic composition is substantially free of at least one or more selected from a group consisting of surface active agents, protic solvents, polar aprotic solvents, and silicone thickening agents.

In one or more embodiments, the hydrophobic composition is substantially free of at least one or more selected from a group consisting of surface active agents, polymeric gelling agents, polyols, short chain alcohols, and silicone thickening agents.

In one or more embodiments, the hydrophobic composition contains less than about 0.4% by weight of the composition; or less than about 0.2% by weight of the composition; or less than about 0.1% by weight of the composition of one of or a combination of two, three or all of surface active agents, protic solvents, polar aprotic solvents, and silicone thickening agents.

The Composition Essential Ingredients as Therapeutic Agents

In certain embodiments, a hydrophobic solvent can possess therapeutic properties. For example, some essential oils can kill microorganisms and can be effective in the treatment or prevention of conditions that involve microbial infection, such as bacterial, fungal and viral conditions. Additionally, hydrophobic solvents can useful for the treatment of conditions which involve damaged skin, such as psoriasis or atopic dermatitis. The combination of a hydrophobic solvent and a therapeutically effective fatty alcohol or fatty acid may afford a beneficial effect in conditions characterized, for example, by infection and/or inflammation.

Fatty alcohols can also possess therapeutic properties. Long chain saturated and mono unsaturated fatty alcohols, e.g., stearyl alcohol, erucyl alcohol, arachidyl alcohol and behenyl alcohol (docosanol) have been reported to possess antiviral, antiinfective, antiproliferative and anti-inflammatory properties (see, U.S. Pat. No. 4,874,794). Longer chain fatty alcohols, e.g., tetracosanol, hexacosanol, heptacosanol, octacosanol, triacontanol, etc., are also known for their metabolism modifying properties and tissue energizing properties.

In one or more embodiments, the active agent may be a placebo or a cosmetic agent. The foamable composition is suitable for use in the manufacture of a medicament including a placebo or active agent.

Combination of Active Agents

Several disorders involve a combination of more than one etiological factor; and therefore, the use of more than one active agents is advantageous. For example, psoriasis involves excessive cell proliferation and inadequate cell differentiation as well as inflammation. Atopic dermatitis involves keratinocyte growth abnormality, skin dryness and inflammation. Bacterial, fungal and viral infections involve pathogen colonization at the affected site and inflammation. Hence, in many cases, the inclusion of a combination of active agents in the pharmaceutical composition can be desirable. Thus, in one or more embodiments, the composition includes at least two active agents, in a therapeutically effective concentration.

In one or more embodiments, a combination of any two or more of an antibacterial, an antiinflamitory, an antifungal and an antiviral agent is contemplated.

In one or more embodiments, a tetracycline antibiotic is the sole active ingredient present in the composition. In one or more embodiments, minocycline hydrochloride is the sole active ingredient present in the composition. In one or more embodiments, doxycycline is the sole active ingredient present in the composition.

In one or more embodiments, the tetracycline antibiotic comprises or is selected from the group consisting of tetracycline, oxytetracycline, demeclocycline, doxycycline, lymecycline, meclocycline, methacycline, minocycline, rolitetracycline, chlorotetracycline and tigecycline.

In one or more embodiments, the tetracycline antibiotic is hydrophobic.

In one or more embodiments, the Log of the distribution constant of the tetracycline antibiotic at pH 7.0 (buffer/chloroform) is equal to or less than about 0.2.

In one or more embodiments, the tetracycline antibiotic is present in a free base form, a hydrate form, a salt form, a chelate complex form or a coordination complex form.

In one or more embodiments, the tetracycline antibiotic does not comprise a hydroxy group at carbons 5, 6, and 7.

In one or more embodiments, the tetracycline antibiotic comprises or is selected from the group consisting of minocycline and doxycycline. In some embodiments, the tetracycline antibiotic is minocycline. In some embodiments, the concentration of minocycline is in a range between about 0.1% to about 10% by weight (e.g., about 0.1% to about 8% by weight, about 0.1% to about 5% by weight, about 0.1% to about 3% by weight, about 0.1% to about 2% by weight, about 0.1% to about 1% by weight, about 0.1% to about 0.75% by weight, about 0.1% to about 0.5% by weight, about 0.1% to about 0.25% by weight, about 0.25% to about 10% by weight, about 0.5% to about 10% by weight, about 1% to about 10% by weight, about 2% to about 10% by weight, about 4% to about 10% by weight, about 6% to about 10% by weight, about 7% to about 10% by weight, about 8% to about 10% by weight, about 0.5% to about 2.0% by weight, about 0.75% to about 1.5% by weight, about 1% to about 3% by weight, about 1% to about 4% by weight, and about 2% to about 6% by weight). In some embodiments, the concentration of minocycline is at least about 0.05% by weight, is at least about 0.1% by weight, at least about 0.5% by weight, at least about 1% by weight, at least about 2% by weight, at least about 4% by weight, at least about 6% by weight, at least about 8% by weight or at least about 10% by weight.

Photosensitivity, for example, manifested as an exaggerated sunburn reaction on areas of the body exposed to direct sunlight or ultraviolet light, has occurred with tetracyclines and minocycline use has also been associated with pigmentation of the skin and other tissues. Suprisingly, it has been previously demonstrated by Applicants in U.S. Ser. No. 13/499,475 that minimal to no skin pigmentation following rubbing of 4% minocycline foam onto the skin was noticed, when observed after about 30 seconds. In fact it was unexpectedly found that the composition had protective properties in the case of UVB-induced sun damage or any other condition associated with sunlight or other light (e.g., laser) exposure. Applicants formulations and methods of treatment may therefore be able to reduce skin photodamage and photoaging, and more generally to reduce oxidative stress and inflammation in skin pathologies which are known to be accompanied by apoptotic cell death.

In one or more embodiments the method is useful for treating impetigo, including administering topically to a surface having the disorder a hydrophobic composition as described above, wherein:

(a) the at least one hydrophobic solvent comprises or is selected from a group consisting of a soybean oil, a coconut oil, a cyclomethicone, a light mineral oil, and mixtures thereof;

(b) the at least one viscosity modifying agent comprises or is selected from a group consisting of a fatty acid, a fatty alcohol, a wax, a hydrogenated castor oil, and mixtures thereof; and (c) the tetracycline antibiotic is minocycline HCl.

In one or more embodiments, the composition further comprises fumed or modified silica ($SiO_2$) such as Aerosil R972.

In one or more embodiments, the minocycline is micronized.

In one or more embodiments, the minocycline has a 90% potency.

In one or more embodiments, the composition is a foamable composition, and further comprises a propellant. Any compatible propellant may be used. In one or more embodiments, the propellant is a gas at room temperature under normal pressure and which may be liquefied at increased pressure at room temperature. Examples of propellants include, without limitation, hydrocarbon propellants such as butane, propane, isobutane, dimethyl ether, fluorocarbons such as 1,1,1,2 tetrafluorethane (Dymel 134), and 1,1,1,2,3, 3,3 heptafluoropropane (Dymel 227), and mixtures thereof. In one or more embodiments, a hydrocarbon mixture AP-70 (a mixture of about 30% w/w butane, 20% w/w isobutane and 50% w/w propane) is used.

In one or more embodiments of the invention, it is disclosed a method for treating impetigo, including administering topically to a surface having the disorder a hydrophobic composition substantially free of surfactants, and/or substantially free of surfactants and polymeric agents as described above, wherein (a) the at least one hydrophobic solvent comprises or is selected from a group consisting of a soybean oil, a coconut oil, a cyclomethicone, a light mineral oil, and mixtures thereof;

(b) the fatty alcohol comprises or is selected from a group consisting of cetostearyl alcohol, myristyl alcohol, stearyl alcohol, behenyl alcohol, and mixtures thereof;

(c) the fatty acid comprises or is selected from the group consisting of stearic acid, beeswax, a hydrogenated castor oil, and mixtures thereof;

(d) the wax comprises or is selected from the group consisting of bees wax, a hydrogenated castor oil, and mixtures thereof; and (e) the tetracycline antibiotic is selected from a minocycline and a doxycycline.

In one or more embodiments, the tetracycline antibiotic is minocycline HCl.

In one or more embodiments, the tetracycline antibiotic is doxycycline hyclate.

Also provided herein is a method for treating human skin diseases especially for the treatment of rosacea, acne, and/or impetigo, including administering topically to a surface having the disorder a hydrophobic composition containing:

(a) a mixture of soybean oil in an amount of about 50 weight percent, coconut oil in an amount of about 24 weight percent, cyclomethicone in an amount of about 5 weight percent, and light mineral oil in an amount of about 4 weight percent;

(b) a mixture of about 3.5 weight percent cetostearyl alcohol, about 2.5 weight percent myristyl alcohol, about 1.5 weight percent stearyl alcohol, about 1 weight percent behenyl alcohol, about 3 weight percent stearic acid, about 2 weight percent beeswax, and about 2 weight percent hydrogenated castor oil;

(c) fumed (modified) silica in an amount of about 0.25 weight percent; and (d) minocycline HCl in an amount of about 1.0 weight percent.

In one or more embodiments of the invention is disclosed a method for treating human skin diseases, especially for the treatment of rosacea, acne, and/or impetigo, including administering topically to a surface having the disorder a hydrophobic composition substantially free of surfactants, and or substantially free of surfactants and polymeric agents as described above, containing:

(a) a mixture of soybean oil in an amount of about 50 weight percent, coconut oil in an amount of about 23.6 weight percent, cyclomethicone in an amount of about 5 weight percent, and light mineral oil in an amount of about 1 weight percent;

(b) a mixture of about 3.5 weight percent cetostearyl alcohol, about 2.5 weight percent myristyl alcohol, about 1.5 weight percent stearyl alcohol, about 1 weight percent behenyl alcohol, about 3 weight percent stearic acid, about 2 weight percent beeswax, and about 2 weight percent hydrogenated castor oil;

(c) modified (fumed) silica (Aerosil R 972) in an amount of about 0.25 weight percent; and (d) minocycline HCl (micronized) in an amount of about 4.44% weight percent.

In one or more embodiments, any composition of the present invention can also contain a fragrance. In one or more embodiments, the fragrance is at a concentration of about 0.1% by weight to about 1% by weight.

In one or more embodiments, the composition comprises about 48% w/w to about 51% w/w of soybean oil. In one or more embodiments, the composition comprises about 23% w/w to about 24% w/w of coconut oil. In one or more embodiments, the composition comprises about 4% w/w to about 6% w/w of cyclomethicone. In one or more embodiments, the composition comprises about 1% w/w to about 5% w/w of light mineral oil.

In one or more embodiments, the composition comprises about 3% w/w to about 4% w/w of cetostearyl alcohol. In one or more embodiments, the composition comprises about 2% w/w to about 4% w/w of stearic acid. In one or more embodiments, the composition comprises about 2% w/w to about 3% w/w of myristyl alcohol. In one or more embodiments, the composition comprises about 1% w/w to about 2% w/w of stearyl alcohol. In one or more embodiments, the composition comprises about 0.5% w/w to about 1.5% w/w of behenyl alcohol. In one or more embodiments, the composition comprises about 1% w/w to about 3% w/w of hydrogenated castor oil. In one or more embodiments, the composition comprises about 1% w/w to about 3% w/w of beeswax.

In one or more embodiments, the composition comprises about 0.1% w/w to about 0.3% w/w of fumed (modified) silica. In one or more embodiments, the composition comprises about 1% w/w to about 4% w/w of minocycline hydrochloride. In one or more embodiments, the composition comprises about 3% w/w to about 15% w/w of propellant based on the weight of the total composition.

In one or more embodiments, there is provided a method for treating impetigo, including administering topically to a surface having the disorder a composition which is highly effective against bacteria, including some multi-drug resistant strains (e.g., MRSA).

In one or more embodiments, there is provided a method for treating impetigo, including administering topically to a surface having the disorder a composition which is highly effective against MRSA bacteria.

In one or more embodiments, there is provided a method for treating impetigo, including administering topically, once a day, to a surface having the disorder a composition comprising a tetracycline antibiotic.

In one or more embodiments, there is provided a method for treating impetigo, including administering topically, twice a day, to a surface having the disorder a composition comprising a tetracycline antibiotic.

In one or more embodiments, there is provided a method for treating impetigo, including administering topically, alternate-day or intermittently, to a surface having the disorder a composition comprising a tetracycline antibiotic.

In one or more embodiments, there is provided a method for treating impetigo, including administering topically, gradual reduction to a lower maintenance dose, which can be increased if further outbreaks occur, to a surface having the disorder a composition comprising a tetracycline antibiotic. In one or more embodiments, a maintenance dose can be applied topically, daily, alternate daily, twice weekly or weekly for a month, two months, quarterly, six months or indefinitely. A maintenance dose can include about 0.9%, or about 0.8%, or about 0.7%, or about 0.6%, or about 0.5%, or about 0.4%, or about 0.3%, or about 0.2%, or about 0.1%, or about 0.09%, or about 0.08%, or about 0.07%, or about 0.06%, or about 0.05% by weight of a tetracycline antibiotic.

In one or more embodiments, there is provided a method for treating impetigo, including administering topically, for at least three days, to a surface having the disorder a composition comprising a tetracycline antibiotic.

In one or more embodiments, there is provided a method for treating impetigo, including administering topically, for less than seven days, to a surface having the disorder a composition comprising a tetracycline antibiotic.

In one or more embodiments, there is provided a method for treating impetigo, including administering topically to a surface having the disorder a composition comprising a tetracycline antibiotic, wherein after 7 days of treatment, at least about 45% of the treated impetigo lesions disappear or show improvement so that no further antimicrobial therapy is necessary. In some embodiments, at least about 50%, at least about 60%, at least about 70% or at least about 80% of the treated impetigo lesions disappear or show improvement. In one or more embodiments, at least about 90% of the treated impetigo lesions disappear or show improvement. In one or more embodiments, a further improvement is observed one week after termination of the treatment.

In one or more embodiments, there is provided a method for treating impetigo, including administering topically to a surface having the disorder a composition comprising a tetracycline antibiotic, wherein after 7 days of treatment, the impetigo lesions are cured. In one or more embodiments, at least about 10% of the lesions are cured after 7 days of treatment. In one or more embodiments, at least about 20% of the lesions are cured after 7 days of treatment. In some embodiment, at least about 30% or at least about 40% of the lesions are cured after 7 days of treatment. In one or more embodiments, at least about 20% of the lesions are cured one week after termination of the treatment. In some embodiment, at least about 30%, at least about 40% or at least about 50% of the lesions are cured one week after termination of the treatment.

The compositions provided herein are manufactured according to the methods described in the art and as described in Example 1. Gels are usually packaged in a tube but can also be packaged in any other convenient delivery form including for example, bottles with a pump mechanism or canisters such as bag in can devices where propellant is separate from the gel. Foam formulations are usually packed in a container with an outlet valve. Possible containers and valves are likewise described in the literature as known by those skilled in the art.

In one or more embodiments, the composition is substantially alcohol-free, i.e., free of short chain alcohols having up to 5 carbon atoms in their carbon chain skeleton. In other embodiments, the composition comprises less than about 5% by weight final concentration of short chain alcohols, for example, less than 2% by weight, or less than 1% by weight. In certain embodiments, the composition is free or substantially free of ethanol, propanol, butanol and pentanol.

One known disadvantage of state of the art compositions is that they must be administered three times a day for a whole week, thus making it especially burdensome for use with small children. It is therefore an advantage of the compositions provided herein is that they can be effective when administered only twice a day. In certain embodiments, the composition may further be effective even if administered once a day or alternate-day according to the condition of the patient. In other embodiments, the composition may be used even if administered more than twice a day and or for more than a week according to the condition of the patient and the concentration of the minocycline.

Another disadvantage of state of the art compositions is that they have an ointment base, comprising petrolatum which is greasy and generally considered unusable in the case of facial treatment of impetigo. Another disadvantage of state of the art compositions is that they contain surfactants. In some cases, irritation at the application site has been reported with the use of such ointments.

It is therefore an advantage of the compositions provided herein that they are breakable gels or foams; and therefore are easy to apply to the skin and also avoid stinging and drying, properties that have been associated with compositions containing surfactants.

Foam is extremely advantageous in the topical treatment of skin diseases, especially in children, who are often sensitive to treatment with a cream or ointment. When dispensed, even in small quantities, drug delivery in the form of a foam can also cover a larger surface area of application while also facilitating better product application in areas where conventional topical products cannot be as effective. A foam also facilitates the use of a lower dosage which can minimize adverse reactions. It absorbs rapidly—without the need of repeated rubbing—which is helpful and important for treatment of damaged or irritated skin, sores, and lesions. The formulation packaged into an aerosol container is devoid of any contact with air, light, or any other form of contamination as it is a completely sealed system throughout the life of the product. Thus, light and oxidation sensitive topical actives can be preserved effectively in the aerosol system.

In one or more embodiments there is provided a method of administering a tetracycline foam composition to a target area such as skin or a mucosa or an eye of a patient comprising releasing a foam, applying it to the area, and collapsing the foam. In one or embodiments, the foam is applied by spreading. In the course of spreading mechanical shear can cause the foam to collapse. In one or more embodiments, the collapsed foam is not washed off. In one or more embodiments it is absorbed onto the area of skin, mucosa or eye.

Breakable gels, which comprise liquid oils and a thickening agent, are also very convenient for use, as they liquefy on application of mild shear force such as gentle rubbing, and in turn, they readily absorb onto the skin.

In one or more embodiments, there is provided a method of applying a tetracycline gel composition to an area of skin or a mucosa or an eye of a patient comprising releasing a gel, applying it to the area, and collapsing or liquefying the gel. In one or more embodiments, the collapsed or liquefied gel is not washed off.

In one or more embodiments, a gel or a liquid gel or a collapsed foam is absorbed within 240 seconds, or within 200 seconds, or within 180 seconds, or within 150 seconds, within 120 seconds, or within 100 seconds, or within 80 seconds, or within 60 seconds, or within 50 seconds, or within 40 seconds, or within 30 seconds, or within 20 seconds, or within 10 seconds, or within 5 seconds, or within 2 seconds or less. By absorbed is meant that the composition enters onto and into an area of skin, mucosa or eye, often forming a thin coating on the surface.

In Phase II clinical tests it has surprisingly been shown that hydrophobic compositions according to the description provided herein have beneficial properties in the treatment of impetigo (see Example 3). The foamable compositions have shown to be highly effective against bacteria, including some multi-drug resistant strains (such as MRSA). The effective eradication of MRSA is encouraging and enables curing the patients, as well as protecting the surrounding infants and children from contracting resistant bacterial infections.

In one or more embodiments, there is provided a method for eradicating MRSA thereby curing patients, and preventing the surrounding infants and children from contracting resistant bacterial infections by applying topically an effective amount of a tetracycline gel, liquid gel or foam to an infected area of a patient in need. In one or more embodiments, the method involves applying a gel, liquid, gel or foam formulation topically to a target surface in need of treatment and breaking the gel or foam over the target site. In one or more embodiments, the method uses a dosage regime of twice daily for three days followed by a daily maintenance dose for one, two, three or more weeks according to the condition and response of the patient. In one or more embodiments, the method uses a dosage regime of twice daily for four days followed by a daily maintenance dose for one, two, three or more weeks according to the condition and response of the patient. In one or more embodiments, the method uses a dosage regime of twice daily for one week followed by a daily maintenance dose for one, two, three or more weeks according to the condition and response of the patient. In one or more embodiments, the method uses a dosage regime of twice daily for two weeks followed by a daily maintenance dose for one, two, three or more weeks according to the condition and response of the patient.

In one or more embodiments, the method uses an additional step of pre cleaning and drying the lesions and surrounding area before applying the gel, liquid gel or foam.

In one or more other embodiments, the method uses an additional step of applying a hyaluronic acid to the lesions and surrounding area after the gel, liquid gel or foam has been absorbed. In certain embodiments the hyaluronic acid is applied once daily at least 1, or, 2 or 3 or 4 or 5 or 6 or 7 or 8 or 9 or 10 or 11 or 12 hours after the tetracycline antibiotic formulation has been absorbed. In one or more embodiments, the hyaluronic acid is applied after the third day. In one or more embodiments, the hyaluronic acid is applied during the maintenance stage. In an alternative embodiment the hyaluronic acid is replaced with or supplemented by a steroid.

In an alternative embodiment the hyaluronic acid or steroid is replaced with or supplemented by an antibiotic. In an embodiment the antibiotic, which is in addition to one or more tetracycline antibiotics, is selected from the group consisting of mupirocin, fusidic acid, a penicillin or penicillin derivative, augmentin, an antistaphylococcal penicillin, amoxicillin/clavulanate, a cephalosporin, cephalexin, a macrolide, erythromycin, clindamycin, trimethoprim-sulfamethoxazole penicillin, retapamulin, and mixtures of any two or more thereof. In an embodiment the antibiotic is applied topically. In another embodiment it is applied orally or by injection or by infusion. In another embodiment more than one antibiotic is applied. For example one is applied topically and another is given orally. The latter may be appropriate for example where there is a systemic as well as a topical bacterial infection.

A randomized double blind Phase II clinical study, conducted in pediatric patients with impetigo, was designed to assess the efficacy, safety, and tolerability of foamable composition comprising minocycline at one of two different concentrations (strengths): a lower concentration of minocycline of 1% by weight and higher concentration of minocycline 4% by weight of the formulation.

Both the minocycline and the foamable compositions were manufactured under current Good Manufacturing Principles (cGMP) conditions. The foamable composition was provided in aluminum aerosol canisters mounted with valve and actuator. Each canister was filled with 25 g of product and 3 g of propellant. Upon actuation of the canister an aliquot of quality foam was released.

The stability of foamable composition containing minocycline was monitored at 5° C., 25° C. and 40° C. during and after the clinical trials and satisfactory stability results were obtained (Example 3).

A total of thirty-two patients were enrolled and randomized in a double-blind, 1% and 4% dose-ranging study; sixteen in each treatment group ages ranging from 2 to 15 years old. Caregivers were instructed to shake the can before use, dispense a small amount of foam and apply a thin layer of medication on the affected area twice a day for 7 days.

The study included four scheduled study visits in which the patients were evaluated: Day 1 (Visit 1) Baseline which included, screening and treatment initiation, Day 3 (Visit 2) which included efficacy and safety assessments, Day 7 (Visit 3)—End of Treatment (EOT) and Day 14 (Visit 4) "follow up" (F/U). Clinical and bacteriological assessments and efficacy evaluations were done at baseline, EOT and F/U. Notably, median number of lesions per patient were 4 and 3.5 in the 1% and 4% minocycline groups respectively. Thus, the severity of the patients in this study was higher than the severity of patients in the studies conducted with Retapamulin ("the majority of patients in both treatment groups presented with only one impetigo lesion"; median=1). (Oranje A P, Chosidow O, Sacchidanand S, Todd G, Singh K, Scangarella N, Shawar R, Twynholm M; Topical retapamulin ointment, 1%, versus sodium fusidate ointment, 2%, for impetigo: a randomized, observer-blinded, noninferiority study. (*Dermatology.* 2007; 215(4): 331-40).

A significant efficacy was demonstrated in both 1% and 4% by weight doses. Clinical response success rates at the end of the treatment were 92.3% and 100% for the 1% or 4% minocycline, respectively (see Example 2 Table 4). Notably, 80% of the total patients were cured or improved significantly after only 3 days of treatment and 100% were found to have been cured or improved at follow up whether the 1% or 4% dose was applied (see Example 2 Table 4). The change from baseline was statistically significant in both dose groups at Day 3 (visit 2) and subsequently at EOT (visit 3) and F/U (visit 4). No significant differences in overall efficacy were found between the 1% and 4% doses.

Microbiological tests were performed on the swabs taken from the patients lesions at Visit 1 and Visit 3. Surprisingly, in patients showing the presence of MRSA at baseline, the bacterial infection was eradicated on day 7 as well as 7 days after the end of treatment in all patients in both dose groups (see Table 5) based on criteria used in Altabax (GSK) study recently approved by FDA.

No drug related side effects were recorded in any of the patients throughout the study, which indicates an enhanced safety of topical foamable minocycline compositions.

These results surprisingly indicated successful treatment of patients with topical foamable compositions containing minocycline with no side effects as opposed to oral minocycline compositions. Thus, Applicants' treatment methods with minocycline in a topical formulation can avoid or minimize unwanted effects seen when given in methods that result in systemic delivery rather than targeted delivery to the skin or mucosal surface in need of treatment. Topical delivery also means that lower doses can be uses again contributing to the elimination or reduction of unwanted side effects. The results confirmed the efficacy and safety of the compositions in the treatment of skin infections such as impetigo. Accordingly, these foamable compositions are expected to be beneficial for the treatment of a range of skin conditions, including acne, rosacea, antibiotic responsive diseases or dermatoses, a skin disease caused by a bacteria and other skin infections. Likewise, these foamable compositions are expected to be beneficial in mucosal infections and in eye infections.

Following one week of treatment, in which the foamable compositions containing either 1% or 4% minocycline were applied twice a day (double blind test), a decrease in the total lesion area per patient of respectively 55% and 47% was observed. One week after the end of the treatment, a further improvement was observed, with a decrease in the total lesion area of respectively 86% and 59% (Table 9).

In one or more embodiments there is provided a method for treating impetigo, including administering topically, to a surface having the disorder, a composition comprising a tetracycline antibiotic, wherein a decrease in the total lesion area of at least about 30%, at least about 40%, or at least about 50% is observed after one week of treatment.

In one or more embodiments, there is provided a method for treating impetigo, including administering topically, to a surface having the disorder, a composition comprising a tetracycline antibiotic, wherein a decrease in the total lesion area of at least about 50%, or at least about 60%, or at least about 70%, or at least about 80% is observed after one week after the end of the treatment.

After one week of treatment in which the foamable compositions containing either 1% or 4% minocycline were applied twice a day (double blind test) followed by a week with no treatment, a clinically and statistically significant decrease in the number of lesions per patient was observed. Most of the patients (about 94%) who received the 1% low concentration had three or more lesions at baseline (38% with 3 lesions and 56% with 4 or more lesions). At EOT this number decreased by half (46%) and at F/U this dropped further with only 8% of the patients had more than three lesions (Table 7).

In one or more embodiments, there is provided a method for treating impetigo, including administering topically, to a surface having the disorder, a composition comprising a tetracycline antibiotic, wherein a decrease in frequency of lesions per patient of at least about 30%, or at least about 40%, or at least about 50% is observed after one week of treatment.

In one or more embodiments, there is provided a method for treating impetigo, including administering topically, to a surface having the disorder, a composition comprising a tetracycline antibiotic, wherein a decrease in frequency of lesions per patient of at least about 50%, or at least about 60%, or at least about 70%, or at least about 80%, or at least about 90% is observed after one week after the end of the treatment.

Following one week of treatment, in which the foamable compositions containing either 1% or 4% minocycline were applied twice a day (double blind test), a dramatic decrease in the number of lesions was observed. As shown in Table 8 the percent of the total number of lesions that disappeared in the 1% or 4% groups was about 39% in each case. One week after the end of the treatment, a further improvement was observed, with a total % number of lesions that had disappeared in the 1% or 4% dose groups was 79% and 61% respectively. As further demonstrated, in Table 8, these changes at EOT and F/U were statistically significant compared to baseline in both 1% and 4% dose groups.

In one or more embodiments there is provided a method for treating impetigo, including administering topically, to a surface having the disorder, a composition comprising a tetracycline antibiotic, wherein a percent of total number lesions that disappeared of at least about 30%, or at least about 40%, or at least about 50% is observed after one week of treatment and wherein these changes at the end of treatment were statistically significant compared to baseline in both 1% and 4% dose groups.

In one or more embodiments there is provided a method for treating impetigo, including administering topically, to a surface having the disorder, a composition comprising a tetracycline antibiotic, wherein at least about 40%, or at least about 50%, or at least about 60%, or at least about 70%, or at least about 75% of total number lesions disappear after one week after the end of the treatment. It is notable from the results below that the changes observed at F/U were statistically significant compared to baseline in both 1% and 4% dose groups.

It is postulated, without being bound by any theory, that the use of a hydrophobic oil based foam vehicle contributes to cutaneous bioavailability, including the achievement of therapeutic levels of minocycline in the pilosebaceous unit. In-vitro skin penetration studies (see e.g. WO11/039637) show that topical administration of minocycline brings appreciable amounts of the drug to its target site of action— the skin, while avoiding the undesirable high systemic exposure and the negative consequences of the oral dosage route.

Another major disadvantage of state of the art compositions is that they are unable to alleviate the symptoms of the disease in all patients. Moreover, a deterioration in the condition of some of the patients was reported the week following the end of treatment. This can be seen for example from the Statistical Review and Evaluation that the CDER (Center For Drug Evaluation and Research) performed on Altabax® (Table 3.4.1, p. 32) showing a decrease in the success rate in the follow up evaluation performed after the end of the treatment.

Surprisingly, in the clinical trials described below, a week after the end of treatment, a further decrease in the total area of all lesions (per patient) was observed (i.e. 100% success rate). So instead of a deterioration, an improvement in all patients was attained. Thus, minocycline had prolonged therapeutic activity amongst all impetigo patients tested (Table 9).

In one or more embodiments there is provided a method for treating impetigo, including administering topically, to a surface having the disorder, a composition comprising a tetracycline antibiotic, having a prolonged therapeutic effect after treatment ceased. In one or more embodiments a further decrease in the total area of all lesions (per patient) of at least about 40%, or at least about 50%, or at least about 60%, or at least about 70%, or at least about 75% is observed after one week after the end of the treatment. In one or more embodiments these changes at F/U are statistically significant compared to baseline in both 1% and 4% dose groups.

In one or more embodiments, there is provided an effective method for treating impetigo, as set out herein to patients with more than two lesions, or more than three lesions, or more than four lesions.

It was very surprising to note that therapeutic effects were achieved also with low concentrations minocycline such as 1%. Thus, it is possible to use lower concentrations of minocycline thereby reducing toxicity and increasing safety. A number of other skin disorders and diseases can be treated with the composition according to the present invention such as acne, rosacea and antibiotic responsive dermatoses.

It was also surprising to note that rapid reduction of signs and symptoms were observed in impetigo patients treated using a twice daily application regime at both the 4% and 1% dose. The decrease in the exudation scores upon comparison of baseline to Day 3 in both the 1% and 4% minocycline groups was clinically and statistically significant. The exudation score further decreased at EOT and F/U. At EOT and F/U in the 1% minocycline group the decrease in the severity signs and symptoms such as erythema, dryness, exudation, itching and pain were statistically significant as well (see Tables 10a-10c). The improvement was apparent as was also the restoration of visible, normal cutaneous topographic features, indicating the return of skin integrity as shown in FIGS. 3-8.

It was suprising to find that in patients with impetigo wounds that substantially or deeply broke the integrity of the skin, the integrity of the skin was restored within 7 days, with an onset of healing within 3 days. By "restoration of the skin integrity", it is intended that for a given lesion of the patient, the skin has healed until a point where it is without crusts and without erythema. By "onset of healing", is intended a change for the better in cutaneous topographic features of the skin and or the beginning of closing of a breach in skin integrity. For example, when the skin lesions started to show an improvement of the erythema or dryness or exudation or peeling or a reduction of the area of the lesions or a reduction in the crust when compared to the baseline. As can be seen in the results described in the Examples section it is particularly suprising that even erythemas disappeared within 7 days of treatment in patients with impetigo wounds.

It may be that the first three days of treatment achieves a significant clinical effect such that improvement can continue for a period therafter for perhaps several days even without further treatment due to a residual effect of the first three days treatment. It follows that a longer initial period of treatment may provide a longer improvement and protection period.

Most approved topical prescription treatments currently available to treat impetigo are in the form of creams and ointments and are associated with a three time daily treatment regimen, which may impact patient compliance. In contrast, the present gel, liquid gel and foamable compositions meet a long felt need for an easier and shorter treatment regimen having an earlier onset and a longer post-treatment effect, while maintaining efficacy (both initial and sustained clearance of lesions). Phase II clinical studies demonstrated that using the twice-daily treatment regimen for impetigo up to a week safely and effectively cleared impetigo lesions with an improvement observed within 3 days of application and the efficacy being sustained a week after the end of treatment. Some initial studies also indicate that even a once a day regime can be effective in treating impetigo.

In one or more embodiments, there is provided a method for treating impetigo, including administering topically, to a surface having the disorder, a composition comprising a tetracycline antibiotic, wherein a decrease in exudation scores is clinically and statistically significant. In one or more embodiments the decrease is seen upon comparison of baseline to day 3, and or to EOT, and or to F/U (e.g. in either or both the 1% and 4% minocycline groups).

In one or more embodiments, there is provided a method for treating impetigo, including administering topically, to a surface having the disorder, a composition comprising a tetracycline antibiotic, wherein a decrease in the severity signs and symptoms such as erythema, dryness, exudation, itching and pain are clinically statistically significant. In one or more embodiments the decrease is seen upon comparison of baseline to day 3, and or to EOT, and or to F/U (e.g. in either or both the 1% and 4% minocycline groups).

In one or more embodiments, there is provided a method for treating impetigo, including administering topically, to a surface having the disorder, a composition comprising a tetracycline antibiotic, wherein an improvement is considered as restoration of visible, normal cutaneous topographic features, indicating the return of skin integrity.

Wound healing is a natural restorative response to tissue injury. Healing is the interaction of a complex cascade of cellular events that generates resurfacing, reconstitution, and restoration of the tensile strength of injured skin. Healing is a systematic process, traditionally explained in terms of 4 overlapping classic phases: hemostasis, inflammation, proliferation, and maturation or remodeling.

To the naked eye one of the markers of a wound is a breach in skin integrity. Returning of skin integrity occurs during the latter stages. It is visibly demonstrated by contraction of the wound. Contraction, is defined as the centripetal movement of wound edges that facilitates closure of a wound defect and results in a decrease in wound size. The rate of contraction depends on many factors including the position size and shape of the wound. Wound healing time means the amount of time it takes for the skin and underlying tissues to meet and fuse after a discontinuation of their surface by trauma. It can take weeks or months depending on the nature and extent of the trauma. For example a simple knife cut on the skin can take two to three weeks to heal if there are no complications. How close the edges of skin are is a relevant factor and the further apart they are the longer the process takes. The process will also take longer if the wound is or becomes infected.

Treating a breach in skin integrity attributable a disorder is not the same as treating the disorder or disease itself. Treating a cause of a disorder or disease may remove the cause but it will not be expected to remove the consequences. For example if the cause is a bacteria or fungi merely eliminating the bacteria will prevent the problem from becoming worse but it will be the bodies natural healing mechanisms, which can then act to restore a breach in skin integrity. Whilst skin integrity is breached there is a risk of further or secondary infections. So there is a need for a treatment that can accelerate the return of normal skin integrity. Accelerating wound healing can prevent or reduce scarring. To the extent an agent or formulation comprising the agent, which is effective in accelerating a return to normal skin integraty can also have a second activity for example, an anti-microbial, or an anti-bacterial or an anti-viral or an antifungal effect then the agent can act in a two or three fold way, namely accelerating the return of skin integrity, and or eliminating any microbes, and or preventing their return, it can be an advantage. However, the skin integrity repair agent can be used in compositions to restore integrity where its property e.g as an antibacterial is not significant as the cause of the breach is e.g. a fungal infection or is not due to a disease or disorder.

In an embodiment the breach in skin integrity is not caused by a disease or disorder but is due to an external physical cause, such a breach caused by an instrument or projection or a sharp object.

In one or more embodiments there is provided a method for treating a breach in skin integrity, including administering topically, to a surface having the breach in skin integrity, a composition comprising a tetracycline antibiotic.

In one or more embodiments there is provided a method for improving a breach in skin integrity, including administering topically, to a surface having the breach in skin integrity, a composition comprising a tetracycline antibiotic, wherein an improvement is considered as restoration of normal cutaneous topographic features and or closing of the breach indicating return of skin integrity.

In one or more embodiments the treatment effect or improvement is due to the presence of the tetracycline. In one or more other embodiments one or more formulation components also have a beneficial effect and add to the treatment effect or improvement. In one or more embodiments the treatment effect or improvement is due to the combination of the carrier composition and the tetracycline. In one or more embodiments the treatment effect or improvement due to the combination is synergistic.

In one or more embodiments the method involves applying a topical tetracycline composition to an area of skin having one or more breaches in skin integrity twice daily for seven days. In one or more other embodiments the application is once daily for seven days. In other embodiments the application is thrice daily for six days, or thrice daily for five days, or thrice daily for four days, or thrice daily for three days. In still other embodiments the application is twice daily for six days, or twice daily for five days, or twice daily for four days, or twice daily for three days.

In one or more embodiments, the restoration of skin integrity is achieved within seven days. By within seven days includes the seventh day. In one or more embodiments, the restoration of skin integrity is achieved within seven days on at least about 25% of the lesions. In one or more embodiments, the restoration of skin integrity is achieved within seven days on at least about 50% of the lesions. In one or more embodiments, the restoration of skin integrity is achieved within seven days on at least about 75% of the lesions. In one or more embodiments, the restoration of the skin integrity is achieved within 7 days with onset of healing being within 3 days. In one or more embodiments, the integrity of the skin is fully restored within 7 days or less. In one or more embodiments, the restoration of the skin integrity is achieved within 3 days. In one or more embodiments, there is provided a restoration of the skin at a more rapid rate than would occur simply by removal of the cause of the lesion and then allowing the skin to heal.

In one or more embodiments the onset of healing is observed within three days. By onset of healing is intended a change for the better in cutaneous topographic features of the skin and or the beginning of closing of a breach in skin integrity.

In one or more embodiments, the restoration of the skin integrity concerns impetigo wounds. In one or more embodiments, the restoration of the skin integrity concerns acne wounds. In one or more embodiments, the restoration of the skin integrity concerns skin wounds or skin breaks.

In one or more embodiments, the the treatment accelerates the restoration of skin integrity. By "acceleration" of the restoration of skin integrity it is intended that restoration of the skin is achieved at a more rapid rate than would occur by the removal of the cause of the lesion and allowing the skin to heal. By way of a non limiting example in the case of a skin breach which is caused by bacteria, it is intended that restoration of the skin is achieved at a more rapid rate than would occur by simply killing the bacteria and allowing the skin to heal. In one or more embodiments the acceleration is at least a 20% improvement in the healing time. In other embodiments it is at least a 30% improvement in the healing time. In further embodiments it is at least a 50% improvement in the healing time. In further embodiments it is at least a 60% improvement in the healing time. In further embodiments it is at least a 70% improvement in the healing time. In further embodiments it is at least a 80% improvement in the healing time. In further embodiments it is at least a 90% improvement in the healing time. In further embodiments it is at least a 100% improvement in the healing time.

In one or more embodiments there is provided a hydrophobic gel or foam composition comprising a tetracycline antibiotic, for use in the restoration of skin integrity by topical application of the foam composition to an area of skin containing a skin lesion.

In one or more embodiments there is provided a method of restoring the integrity of an area of skin containing a skin lesion, which method comprises topical application to said area of a hydrophobic gel or foam composition comprising a tetracycline antibiotic.

It should be noted that no clinical recurrences and no adverse events were observed in any of the groups. Minocycline topical foam administered twice daily was well-tolerated, with high rates of clinical and microbiological responses for treating impetigo. In one or more embodiments, there is provided a method for treating impetigo, including administering topically, to a surface having the disorder, a composition comprising a tetracycline antibiotic, having no clinical recurrences and no adverse events.

In one or more embodiments there is provided a method for treating impetigo, including administering topically, to a surface having the disorder, a composition comprising a tetracycline antibiotic administered twice daily which is well-tolerated, with high rates of clinical and microbiological responses.

As with other therapeutic regimens, patient compliance is essential in the effectiveness of prescribed antibiotics. With poor compliance, therapeutic goals are less likely to be achieved, resulting in poorer patient outcomes. Poor compliance is associated with deteriorating health, the need for additional consultations, the emergence of bacterial resistance, extra drugs, additional hospital admissions, and increases in direct and indirect costs of healthcare management.

In general, patients are more compliant with simple and less-frequent dosing regimens. Both the dosage schedule and the patient's daily routine should be considered when prescribing antibiotics. Topical agents may also be more attractive than oral therapy because they reduce the potential for systemic side effects, typically nausea and diarrhea, which are commonly associated with many systemic antibiotics. They may also help provide a reduction in cross contamination by providing a barrier with antibiotic over the infected area.

Satisfaction questionnaires, answered by the patient's parents at EOT, revealed high satisfaction with treatment, as exemplified in Table 11. A majority of caregivers in both groups rated the product as "very satisfactory" or "excellent" in both usability and general satisfaction categories.

In one or more embodiments there is provided a method for treating impetigo, including administering topically, to a surface having the disorder, a composition comprising a tetracycline antibiotic administered twice daily which has a high or improved patient compliance e.g. compared with existing treatments.

In one or more embodiments there is provided a method of maintenance therapy, to prevent impetigo recurrence or reduce the severity of the impetigo recurrence, applied to a patient in need which comprises applying to the skin on a regular basis a therapeutically effective amount of a dermatological composition comprising a therapeutically effective amount of a tetracycline antibiotic.

In one or more embodiments there is provided a regime or regimen for treating a patient having impetigo, which comprises applying to the afflicted skin region on a regular basis a therapeutically effective amount of a dermatological composition, said composition comprising a therapeutically effective amount of a tetracycline antibiotic.

In one or more embodiments there is provided the use of an tetracycline antibiotic compound for the manufacture of a medicament for treating impetigo in a human in need thereof, wherein the tetracycline antibiotic compound is to be administered topically to said human in an amount that is effective to treat impetigo.

In one or more embodiments there is provided a tetracycline antibiotic for use in treating and/or preventing impetigo, wherein the tetracycline antibiotic is used in a composition administered topically.

In one or more embodiments there is provided a composition comprising a tetracycline antibiotic for use in treating impetigo in an individual suffering therefrom comprising topically administering the composition to the individual in an amount and for a time sufficient to decrease the number of impetigo lesions present in the skin of the individual. In one or more embodiments there is provided a hydrophobic gel or foam composition comprising a tetracycline antibiotic for use in treating a disorder selected from the group consisting of impetigo, acne, rosacea, and a skin disease cased by a bacteria, wherein the hydrophobic gel or foam composition is administered topically at least once daily for at least three days to the skin, mucosa, or eye.

In one or more embodiments there is provided a hydrophobic gel or foam composition comprising a minocycline antibiotic for use in treating a disorder selected from the group consisting of impetigo, acne, rosacea, and a skin disease cased by a bacteria, wherein the hydrophobic gel or foam composition is administered topically at least twice daily for at least seven days to the skin, mucosa, or eye.

In one or more embodiments there is provided a hydrophobic gel or foam composition comprising a minocycline antibiotic for use in treating a disorder selected from the group consisting of impetigo, acne, rosacea, and a skin disease cased by a bacteria, wherein the hydrophobic gel or foam composition is administered topically at least once daily for at least three days to the skin, mucosa, or eye; wherein the hydrophobic gel or foam composition is waterless and does not comprise a silicone other than cyclomethicone.

In one or more embodiments there is provided a hydrophobic gel or foam composition comprising a minocycline antibiotic for use in treating a disorder selected from the group consisting of impetigo, acne, rosacea, and a skin disease cased by a bacteria, wherein the hydrophobic gel or foam composition is administered topically at least once daily for at least three days to the skin, mucosa, or eye; wherein the hydrophobic gel or foam composition is waterless and does not comprise a polyethylene gelling agent or polyethylene homopolymer or polyethylene copolymer.

In one or more embodiments there is provided a hydrophobic gel or foam composition comprising a minocycline antibiotic for use in treating a disorder selected from the group consisting of impetigo, acne, rosacea, and a skin disease cased by a bacteria, wherein the hydrophobic gel or foam composition is administered topically at least once daily for at least three days to the skin, mucosa, or eye; wherein the minocycline antibiotic is the sole active ingredient present in the composition.

In one or more embodiments there is provided a hydrophobic foam composition or gel comprising a tetracycline antibiotic for use in retarding, arresting, or reversing the progression of impetigo, acne, rosacea, and a skin disease cased by a bacteria, wherein the hydrophobic foam composition or gel is applied topically to the skin at least once a day for at least three days.

In one or more embodiments there is provided a hydrophobic gel or foam composition comprising a tetracycline antibiotic, for use in the restoration of skin integrity by topical application of the foam composition to an area of skin containing a skin lesion.

In one or more embodiments there is provided a method of restoring the integrity of an area of skin containing a skin lesion, which method comprises topical application to said area of a hydrophobic gel or foam composition comprising a tetracycline antibiotic. In one or more embodiments the tetracycline is a minocycline. In an embodiment it is minocycline hydrochloride.

Thus, it was unexpectedly demonstrated that topical minocycline foam offered a safe and effective alternative to fusidic acid, mupirocin and retapamulin for the topical treatment of impetigo especially in children. The ease of use, with twice daily dosing, as well as its broad spectrum of activity, the lack of adverse effects and the rapid reduction of signs and symptoms including exudation make it an attractive choice and a potentially valuable medication for the treatment of acute bacterial skin infections.

Further provided herein is a method of treating human skin disorders such as acne, rosacea, and/or impetigo by topical application of a foam or gel or liquid gel as described herein to a patient in need thereof.

In one or more embodiments there is provided a method of treating or alleviating a disorder selected from the group consisting of impetigo, acne, rosacea, and a skin disease caused by a bacteria, comprising administering topically at least once daily for at least three days to a target area on a subject having the disorder a hydrophobic gel or foam composition comprising a tetracycline antibiotic wherein the target area comprises an area of skin, mucosa, or eye.

In one or more embodiments the hydrophobic gel or foam composition comprises:
  a) about 60% to about 99% by weight of at least one hydrophobic solvent;
  b) at least one viscosity-modifying agent selected from the group consisting of a fatty alcohol, a fatty acid, and a wax; and
  c) a therapeutically effective amount of a tetracycline antibiotic.

In one or more embodiments the hydrophobic foam is formed from the hydrophobic gel composition further comprising a propellant.

In one or more embodiments the disorder is impetigo.

In one or more embodiments the tetracycline antibiotic is selected from the group consisting of tetracycline, oxytetracycline, demeclocycline, doxycycline hyclate, lymecycline, meclocycline, methacycline, minocycline hydrochloride, rolitetracycline, chlorotetracycline, and tigecycline.

In one or more embodiments the tetracycline antibiotic is minocycline hydrochloride.

In one or more embodiments the minocycline hydrochloride is present in the composition at a concentration of about 1% by weight.

In one or more embodiments the minocycline hydrochloride is present in the composition at a concentration of about 4% by weight.

In one or more embodiments the hydrophobic gel or foam composition is applied at a frequency selected from the group consisting of three times daily, twice daily, and once daily.

In one or more embodiments the hydrophobic gel or foam composition is administered for a period selected from the group consisting of four days, five days, six days, seven days, eight days, nine days, ten days, eleven days, twelve days, thirteen days, and two weeks.

In one or more embodiments a maintenance dose is applied thereafter at a frequency selected from the group consisting of every two days, three times a week, twice a week, and once a week.

In one or more embodiments the maintenance dose is discontinued after a period selected from the group consisting of a week, two weeks, three weeks, four weeks, a month, two months, and three months.

In one or more embodiments the hydrophobic foam composition or gel is effective against methicillin-resistant *S. aureus* bacteria associated disorders.

In one or more embodiments at least about 40% of the impetigo lesions are cured after one week of treatment, wherein the hydrophobic foam composition or gel is administered twice daily.

In one or more embodiments at least about 50% of the impetigo lesions are cured when observed one week after the end of the treatment.

In one or more embodiments a decrease of at least about 50% in the total area of the impetigo lesions is obtained after one week of treatment, wherein the composition is administered twice daily.

In one or more embodiments a decrease of at least 80% in the total area of the impetigo lesions is obtained when observed one week after the end of the treatment.

In one or more embodiments the hydrophobic gel or foam composition comprises:
  a) about 48% to about 51% by weight of soybean oil;
  b) about 23% to about 25% by weight of coconut oil;
  c) about 4% to about 6% by weight of cyclomethicone;
  d) about 3% to about 5% by weight of light mineral oil;
  e) about 3% to about 4% by weight of cetostearyl alcohol;
  f) about 2% to about 4% by weight of stearic acid;
  g) about 2% to about 3% by weight of myristyl alcohol;
  h) about 1% to about 3% by weight of hydrogenated castor oil;
  i) about 1% to about 3% by weight of beeswax;
  j) about 1% to about 2% by weight of stearyl alcohol;
  k) about 0.5% to about 1.5% by weight of behenyl alcohol;
  l) about 0.2% to about 0.5% by weight of modified (fumed) silica; and
  m) about 1% by weight of minocycline hydrochloride or doxycycline hyclate.

In one or more embodiments the hydrophobic gel composition further comprises about 3% to about 25% by weight of propellant based on the total weight of the hydrophobic gel composition.

In one or more embodiments the hydrophobic gel or foam composition comprises:
  a) about 48% to about 51% by weight of soybean oil;
  b) about 23% to about 25% by weight of coconut oil;
  c) about 4% to about 6% by weight of cyclomethicone;
  d) about 0.5% to about 1.5% by weight of light mineral oil;
  e) about 3% to about 4% by weight of cetostearyl alcohol;
  f) about 2% to about 4% by weight of stearic acid;
  g) about 2% to about 3% by weight of myristyl alcohol;
  h) about 1% to about 3% by weight of hydrogenated castor oil;
  i) about 1% to about 3% by weight of beeswax;
  j) about 1% to about 2% by weight of stearyl alcohol;
  k) about 0.5% to about 1.5% by weight of behenyl alcohol;
  l) about 0.2% to about 0.5% by weight of modified (fumed) silica; and
  m) about 4% by weight of minocycline hydrochloride or doxycycline hyclate.

In one or more embodiments the hydrophobic gel composition further comprises about 3% to about 25% by weight of propellant based on the total weight of the hydrophobic gel composition.

In one or more embodiments it is provided a method for retarding, arresting, or reversing the progression of a disorder in a mammalian subject in need thereof, the disorder selected from the group consisting of impetigo, acne, rosacea, and a skin disorder caused by a bacteria, the method comprising topically applying to the skin of the subject a hydrophobic foam composition or gel comprising a tetracycline antibiotic at least once a day for at least three days, thereby retarding, arresting, or reversing the progression of the disorder in the subject.

In one or more embodiments the hydrophobic gel or foam composition comprises:
d) about 60% to about 99% by weight of at least one hydrophobic solvent;
e) at least one viscosity-modifying agent selected from the group consisting of a fatty alcohol, a fatty acid, and a wax; and
f) a therapeutically effective amount of a tetracycline antibiotic.

In one or more embodiments the hydrophobic gel composition further comprises a propellant.

In one or more embodiments the tetracycline antibiotic is selected from the group consisting of tetracycline, oxytetracycline, demeclocycline, doxycycline hyclate, lymecycline, meclocycline, methacycline, minocycline, minocycline hydrochloride, rolitetracycline, chlorotetracycline, and tigecycline.

In one or more embodiments the tetracycline antibiotic is minocycline hydrochloride.

In one or more embodiments the tetracycline antibiotic is minocycline hydrochloride at a concentration of about 1% or about 4% by weight.

In one or more embodiments at least about 50% clinical success is observed after three days of treatment when the hydrophobic gel or foam composition is administered twice daily.

In one or more embodiments the hydrophobic gel or foam composition is safe and has high rates of clinical and microbiological responses when the hydrophobic gel or foam composition is administered twice daily.

In one or more embodiments the step of administering includes releasing the hydrophobic gel or foam composition and applying it onto the target area having the disorder, by collapsing and or spreading it as a thin layer on the target area using mild mechanical force thereby resulting in the hydrophobic gel or foam composition collapsing and being absorbed onto the a target area.

In one or more embodiments the hydrophobic gel or foam composition is absorbed within at least 120 seconds.

In one or more embodiments the method further comprises using a sterile applicator or prior to the steps of administering and/or collapsing and/or spreading, the hands of the person spreading are sterilized in order to avoid cross contamination.

In one or more embodiments a significant decrease in exudation score is obtained after three days of treatment, when the composition is administered twice daily.

In one or more embodiments a significant decrease in severity signs and symptoms is obtained after a week of treatment, when the composition is administered twice daily.

In one or more embodiments the decrease is at least from severe to moderate or from moderate to mild or from mild to absent.

In one or more embodiments the decrease is at least from severe to moderate or from moderate to mild or from mild to absent.

In one or more embodiments the composition has a shelf life of at least two years at ambient temperature.

In one or more embodiments the restoration of the skin integrity is achieved within seven days.

In one or more embodiments the onset of healing is achieved within three days.

In one or more embodiments there is provided a hydrophobic gel or foam composition comprising a tetracycline antibiotic, for use in the restoration of skin integrity or acceleration of the restoration of the integrity of an area of broken skin or mucosa by topical application of the gel or foam composition to target area on a subject comprising an area of broken skin or mucosa or an area of skin containing a skin lesion,
wherein the gel or foam composition consists of a carrier comprising about 60% to about 99% by weight of at least one hydrophobic oil.

In one or more embodiments the carrier further comprising at least one viscosity-modifying agent, selected from the group consisting of a fatty alcohol, a fatty acid and a wax.

In one or more embodiments the tetracycline antibiotic is:
a. a derivative of polycyclic naphthacene carboxamide; or
b. selected from tetracycline, chlortetracycline, oxytetracycline, demeclocycline, doxycycline, lymecycline, meclocycline, methacycline, minocycline, rolitetracycline, chlorotetracycline and tigecycline; or
c. is a tetracycline antibiotic having Log Kp equal to, or lower than about 0.2;
d. does not comprise any hydroxy group at Carbons 5, 6, and 7
wherein the tetracycline antibiotic is a free base, or hydrate form, or a salt form or a complex form, or a derivative of said tetracycline antibiotic.

In one or more embodiments the tetracycline antibiotic is a doxycycline or a minocycline.

In one or more embodiments the tetracycline antibiotic is present in the composition in an amount ranging from about 0.1% to about 10%.

In one or more embodiments the application is at least once daily for at least three days.

In one or more embodiments the hydrophobic foam is formed from the hydrophobic gel composition further comprising a propellant.

In one or more embodiments the broken skin is due to a skin disorder selected from the group consisting of impetigo, acne, rosacea, and a skin disease caused by a bacteria.

In one or more embodiments the tetracycline antibiotic is minocycline hydrochloride and wherein the minocycline hydrochloride is present in the composition at a concentration of about 1% by weight or about 4% by weight.

In one or more embodiments the hydrophobic gel or foam composition is applied at a frequency selected from the group consisting of three times daily, twice daily, and once daily and is administered for a period selected from the group consisting of at least four days, five days, six days, seven days, eight days, nine days, ten days, eleven days, twelve days, thirteen days, and two weeks.

In one or more embodiments the hydrophobic foam composition or gel is effective against methicillin-resistant *S. aureus* bacteria associated disorders.

In one or more embodiments the disorder is impetigo and a decrease of at least 80% in the total area of the impetigo lesions is obtained when observed one week after the end of the treatment.

In one or more embodiments the restoration of the skin integrity is achieved within seven days.

In one or more embodiments the onset of healing is achieved within three days.

In one or more embodiments the hydrophobic gel or foam composition comprises:
a) about 48% to about 51% by weight of soybean oil;
b) about 23% to about 25% by weight of coconut oil;
c) about 4% to about 6% by weight of cyclomethicone;
d) about 0.5% to about 5% by weight of light mineral oil;
e) about 3% to about 4% by weight of cetostearyl alcohol;
f) about 2% to about 4% by weight of stearic acid;
g) about 2% to about 3% by weight of myristyl alcohol;
h) about 1% to about 3% by weight of hydrogenated castor oil;
i) about 1% to about 3% by weight of beeswax;
j) about 1% to about 2% by weight of stearyl alcohol;
k) about 0.5% to about 1.5% by weight of behenyl alcohol;
l) about 0.2% to about 0.5% by weight of modified (fumed) silica; and
m) about 1% or about 4% by weight of minocycline hydrochloride or doxycycline hyclate, and wherein the tetracycline antibiotic is suspended in the carrier.

Methods

Canisters Filling and Crimping

Each aerosol canister is filled with the pre-foam formulation ("PFF", i.e., foamable carrier) and crimped with valve using vacuum crimping machine. The process of applying a vacuum will cause most of the oxygen present to be eliminated. Addition of hydrocarbon propellant may, without being bound by any theory, further help to reduce the likelihood of any remaining oxygen reacting with the active ingredient. It may do so, without being bound by any theory, by one or more of dissolving in, to the extent present, the oil or hydrophobic phase of the formulation, by competing with some oxygen from the formulation, by diluting out any oxygen, by a tendency of oxygen to occupy the dead space, and by oxygen occupying part of the space created by the vacuum being the unfilled volume of the canister or that remaining oxygen is rendered substantially ineffective in the formulation.

Pressurizing & Propellant Filling

Pressurizing is carried out using a hydrocarbon gas or gas mixture. Canisters are filled and then warmed for 30 seconds in a warm bath at 50° C. and well shaken immediately thereafter.

Tests

By way of non-limiting example the objectives are briefly set out below as would be appreciated by a person of skill in the art.

Collapse Time

Collapse Time, which is the measure of thermal stability, is examined by dispensing a given quantity of foam and photographing sequentially its appearance with time during incubation at 36° C. The collapse time result is defined as the time when the foam height reaches 50% of its initial height or if the foam has not yet reached 50% of its initial height after say 180 seconds then the collapse time is recorded as being >180. By way of illustration, one foam may remain at 100% of its initial height for three minutes, a second foam may reach 90% of its initial height after three minutes, a third foam may reach 70% of its initial height after three minutes, and a fourth foam may reach 51% of its initial height after three minutes, nevertheless in each of these four cases the collapse time is recorded as >180 seconds since for practical purposes for easy application by a patient to a target the majority of the foam remains intact for more than 180 seconds. If the foam, for example, reaches 50% of its original height after say 100 seconds it would be recorded as having a collapse time of 100 seconds. It is useful for evaluating foam products, which maintain structural stability at skin temperature for at least 1 minute. Foams which are structurally stable on the skin for at least one minute are termed "short term stable" carriers or foams.

Alternatively, a Simple Collapse Time can be assessed by placing a foam sample on the warm fingers of a volunteer and measuring the time it takes to melt on the fingers.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude. Unless otherwise stated, viscosity of the pre-foam formulation (PFF) is provided. It is not practical to try and measure the viscosity of the foamable formulation with regular propellants since they have to be stored in sealed pressurized canisters or bottles. In order to simulate the viscosity in the foamable formulations with propellant an equivalent weight of pentane (a low volatile hydrocarbon) is added to and mixed with the pre-foam formulation and left overnight. The viscosity is then measured as above.

FTC (Freeze Thaw Cycles)

Foam appearance under extreme conditions of repeated heating and cooling is evaluated by cycling through cooling, heating, (first cycle) cooling, heating (second cycle) etc., conditions, commencing with −10° C. (24 hours) followed by +40° C. (24 hours) and measuring the appearance following each cycle. The cycle is repeated up to three times.

Chemical Stability

The amount of active agent present is analyzed chromatographically in foam released from various pressurized canisters or in the gel or liquid gel. Analysis is carried out at baseline and at appropriate time intervals thereafter. The canisters are typically stored in controlled temperature incubators at one or more of 5° C., 25° C., 40° C. and 50° C. At appropriate time intervals canisters are removed and the amount of active agent in the foam sample is measured.

Microbiological Tests

Microbial load: Testing was performed according to EP 2.6.12 and 2.6.13 as described in the European Pharmacopea.

Preservative efficacy: Testing was performed according to USP <51> and EP 5.6, 2007 5.1.3. as described in the European and US Pharmacopea.

The test consists of challenging the product with specified microorganisms, storing the inoculated preparations at a prescribed temperature, removing the inoculated samples at specified intervals of time and counting the number of viable organisms in the withdrawn samples using a plate-count procedure. Formulations were challenged by introducing the following microorganisms:

*Escherichia coli* (ATCC no. 8739)
*Staphylococcus aureus* (ATCC no. 6538)
*Pseudomonas aeruginosa* (ATCC no. 9027)
*Candida albicans* (ATCC no. 10231)
*Aspergillus niger* (ATCC no. 16404)

The number of colony-forming units (cfu/g) determined at each incubation time point was compared to the number of cfu/g measured in non-inoculated control samples. In order to verify that the samples tested are free of microbial contaminants, the microbial load (base-line) in the samples was determined prior to preservative efficacy testing. Study results are expressed as the number of surviving microorganisms (cfu/g).

Water Activity (Aw): The test for water activity was performed on pre-foam formulation samples introduced into the measuring cell of a PAWKIT water activity meter from DECAGON.

In-vitro effect on microbial growth: The tested microorganism is grown on Tryptic Soy Agar Slants. After incubation, the bacteria is harvested using sterile buffer phosphate pH 7.0, to obtain a microbial count of about $10^4$ cfu/ml. 0.2 ml of the above suspension is spread on Letheen Agar plate and put aside to dry for 20 minutes at room temperature. A sterile disc of 6 mm diameter which has been soaked in 10 µl of the tested antibacterial pre-foam-formulation (PFF) is put on the microbial film, the plate is incubated at 35° C. for 1-2 days. A control experiment is also performed where no antibacterial material is put on the sterile discs. Antimicrobial activity of the tested material inhibits growth of the microorganism around the disc, leaving a transparent zone around it. The diameter of the inhibition zone is measured in mms.

Compatibility

Active agent is incubated with various excipients individually at one or more temperatures and at different ratios of active agent to a single excipient for a certain fixed period or to the point where degradation was suspected. The period can be for example 3 or 7 or 14 or 21 or 28 days or longer. Visual inspection is a criterion for indication of compatibility. Any change of color indicates oxidation or degradation. For example, the color of an intact MCH suspension is a pale yellow; and a change of color e.g., to dark orange, red, green, brown and black, indicates oxidation or degradation. Tests are also carried out with combinations of excipients.

Color/Pigmentation

Part A—Color Change

Samples of formulations are observed and then incubated during 3 months at 25° C., 30° C. and 40° C. Following this period the foam product is actuated and color is observed, and a change, if any, is noted.

Part B—Pigmentation

Samples are applied to fair healthy human skin to observe whether any skin pigmentation occurs. The skin is observed prior to and 30 seconds following application.

EXAMPLES

Example 1—General Manufacturing Procedures for a Gel or a Foam

The following procedures are used to produce gel or foam samples, in which only the steps relevant to each formulation are performed depending on the type and nature of ingredients used.

Step 1: Hydrophobic solvents such as mineral oils are mixed at room temperature. Others solvents such as silicones, if present, are added at room temperature under mixing until formulation homogeneity is obtained.

Step 2: The formulation is warmed to 70-80° C. and solid compounds such as fatty alcohols, fatty acids and waxes are added and mixed until complete dissolution.

Step 3: The formulation is cooled down to 30-40° C. and active agents such as tetracyclines are added under mixing until formulation homogeneity is obtained.

Step 4: For gel compositions, the formulation is packaged in suitable containers. For foamable compositions, the formulation is packaged in aerosol canisters which are crimped with a valve, pressurized with propellant and equipped with an actuator suitable for foam dispensing. Optionally, a metered dosage unit can is utilized, to achieved delivery of desirable and/or repeatable measured doses of foam.

Step 5: For foamable compositions, pressurizing is carried out using a hydrocarbon gas or gas mixture. Canisters are filled and then warmed for 30 seconds in a warm bath at 50° C. and well shaken immediately thereafter.

Step 6: The canisters or containers are labeled.

Example 2—Clinical Study Phase II in Impetigo Patients

1. Study Synopsis

STUDY TITLE: A randomized, parallel-group, double blind, comparative clinical trial, to assess the safety and efficacy of topically applied FXFM244 antibiotic foam in the treatment of impetigo STUDY MEDICATION: Minocycline hydrochloride foam (1% and 4% compositions, as described in section 9 below.)

DOSAGE: Patients were treated topically on skin areas affected by impetigo twice daily for 7 days.

INDICATION: Impetigo

DESIGN: A randomized, parallel-group, double (Investigator, patient) blind, comparative clinical trial, to assess the safety and efficacy of topically applied minocycline hydrochloride foam in the treatment of impetigo VARIABLES: Efficacy and safety in the treatment of impetigo PATIENTS: 32 patients (19 male and 13 female patients), 2 years of age or older, diagnosed with impetigo contagiosa or uncomplicated blistering impetigo 2. Clinical Study Design The protocol and informed consent forms were approved by each clinical site's local Ethics Committee (EC) and the Israel Ministry of Health prior to study initiation. To be eligible for the study, the subject's parent or legal guardian was required to sign a written informed consent document and have been willing and able to comply with the requirements of the protocol. Children aged 2 years and older with at least two impetigo lesions were enrolled and randomized into a parallel group study testing the two different strengths (1% and 4%) of the study medication.

Treatment was administered topically two times a day (BID) for 7 days to all subjects. Patients were instructed to shake the canister before use, dispense a small amount of foam and apply it by collapsing and spreading it as a thin layer on the affected area. A target total of thirty two subjects were enrolled and randomized with sixteen in each treatment group. The study included four scheduled study visits: Day 1 (Visit 1—Baseline) screening and treatment initiation; Day 3 (±1)—(Visit 2 Interim visit) with efficacy and safety assessment; Day 7 (+1)—(Visit 3—End of Treatment (EOT)) and Day 14 (±2) (Visit 4—Follow-up (F/U)). Clinical and bacteriological assessments and efficacy evaluations were done at Baseline, EOT and F/U.

Patient Demographics

Patients who enrolled into the study were classified as follow:

The intent-to-treat clinical (ITTC) population consisted of all randomized patients who applied at least one dose of study medication.

The clinical per protocol (PPC) population included all ITTC patients who satisfied the inclusion/exclusion criteria and subsequently adhered to the protocol.

The intent-to-treat bacteriological (ITTB) population consisted of all randomized patients who applied at least one dose of study medication and had a pathogen identified at study entry.

The bacteriological per protocol (PPB) population included all ITTB patients who satisfied the inclusion/exclusion criteria and subsequently adhered to the protocol.

3. Statistical Methodology

All measured variables and derived parameters were tabulated by descriptive statistics. Descriptive statistics summary tables included sample size, absolute and relative frequency of categorical variables and sample size, arithmetic mean, standard deviation, median, minimum and maximum for means of continuous variables per group.

The Paired T-test was applied for testing differences between baseline assessment and all the post baseline assessments for sum of total area of all lesions within groups, and for efficacy presentation parameters of all lesions within groups.

The Chi-square test was applied for testing the statistical significance of the differences in frequency of categorical variables between the study groups.

95% Confidence Interval (CI) was calculated for the calculated proportions of the main efficacy variables using a binomial proportion for one-way tables.

All tests applied were two-tailed, and p value of 5% or less was considered statistically significant. The data was analyzed using the SAS® version 9.1 for Windows (SAS Institute, Cary N.C.).

4. Clinical Microbiology Methods

The microbiology testing of the clinical samples was performed by using culture swabs (Amies) obtained from the target lesion of each study patient, at Days 1, 7 and 14. The patient samples were forwarded to a single microbiology laboratory, at the American Medical Laboratories—AML Israel for processing. All culture swabs were processed the same day that they were collected. Each specimen was aerobically plated into Orientation agar, Blood Agar (BAP), CDC and thioglycolate. Culture plates were incubated up to 48 h at 35° C., and then examined for colony morphology consistent with *S. aureus* and *S. pyogenes*. Identification of *S. aureus* and/or *S. pyogenes* colonies included the following tests: catalase, coagulase (Staphitect, Oxoid), Streptococcal grouping kit (Oxoid). Further identification and sensitivity testing was performed using the MicroScan WalkAway (Siemens) auto analyzer, including oxacillin for *S. aureus*.

5. Clinical and Bacteriological Response to Treatment

The success criteria (clinical success, clinical failure and bacteriological success) were adapted from those specified in the registration trials for the the recently approved Altabax.[1] as defined above. Regarding bacteriological response, if after baseline there were no exudates and/or if samples were not taken because the lesion were cleared, such cases were considered a clinical success, pathogen eradication was presumed and the subject was considered a bacteriological success. The primary efficacy parameter was "clinical response" (success or failure) at the EOT visit (Visit 3).

[1] Oranje A P, Chosidow O, Sacchidanand S, Todd G, Singh K, Scangarella N, Shawar R, Twynholm M; Topical retapamulin ointment, 1%, versus sodium fusidate ointment, 2%, for impetigo: a randomized, observer-blinded, non-inferiority study. Dermatology. 2007; 215(4):331-40.

In addition to clinical response and bacteriological response, the following individual efficacy parameters were also recorded:

Lesion count and area.

Additional signs and symptoms, including erythema, dryness, exudation, peeling, burning, itching and pain (exudation, burning, itching and pain are most relevant to the severity of impetigo).

6. Safety and Tolerability

Safety and tolerability were determined for all randomized patients by the investigator at each visit. All adverse experiences were classified by the investigator as either unrelated; unlikely related; suspected or probably related to the study drug. Safety was assessed using different parameters such as vital signs (blood pressure, heart rate, temperature) and physical examination of body systems.

7. Satisfaction

At study visits 3 and 4 (EOT and F/U), the patients' parents filled out a questionnaire regarding usability and treatment satisfaction. Different parameters were assessed such as greasiness, shininess, stickiness, moistness of the skin, general feeling, odor, use of pump and control of the amount, general satisfaction from foam and recommendation.

8. Study Results 8.1. Study Population

The study was conducted at three centers. A total of thirty-two patients with clinically diagnosed impetigo were randomized to two groups, with sixteen patients in each group. One group received the 1% minocycline foam and the other group received the 4% minocycline foam. The study was randomized and neither the investigators, nor the patients and their parents nor their legal guardian knew what strength of medication was dispensed.

Table 1 summarizes the primary characteristics of the study population and the attendance profile in each study group. There was no statistically significant difference between the dosage groups in the baseline demographics. There were no cases of unblinding before the end of the study.

Table 2 details the classification of these patients into ITTC, PPC, ITTB and PPB study groups.

TABLE 1

| Patient demographics | | | |
|---|---|---|---|
| | 1% | 4% | All |
| Patients randomized | 16 | 16 | 32 |
| Age, years | | | |
| Mean (SD) | 5.9 | 5.6 | 5.8 |
| Range | 2-15 | 3-14 | 2-15 |
| Sex (male/female) | 10/6 | 9/7 | 19/13 |
| Patients who attended Day 3 | 16 | 14 | 30 |
| Patients who attended EOT | 13 | 11 | 24 |
| Patients who attended F/U | 12 | 8 | 20 |
| Patients withdrawn | 4 | 8 | 12 |
| Reasons for withdrawal before F/U | | | |
| Adverse event | 0 | 2 | 2 |
| Protocol violation | 1 | 1 | 2 |
| Lost to follow-up | 2 | 4 | 6 |
| Withdrew consent | 0 | 1 | 1 |
| Other | 1 | 0 | 1 |

TABLE 2a

Classification of study patients into ITTC, PPC, ITTB and PPB analysis groups

| | 1% | | | 4% | | | All | | |
|---|---|---|---|---|---|---|---|---|---|
| | Day 3 | EOT | F/U | Day 3 | EOT | F/U | Day 3 | EOT | F/U |
| Intent-to-treat clinical (ITTC) | 16 | 14 | 13 | 14 | 12 | 10 | 30 | 26 | 23 |
| Clinical per-protocol (PPC) | 16 | 13 | 12 | 14 | 11 | 8 | 30 | 24 | 20 |
| Intent-to-treat bacteriological (ITTB) | 12 | 10 | 9 | 14 | 12 | 10 | 26 | 22 | 19 |
| Bacteriological per protocol (PPB) | 12 | 9 | 8 | 14 | 11 | 8 | 26 | 20 | 16 |

TABLE 2b

Classification of of study patients according to type of Impetigo

| | 1% | | 4% | | All | |
|---|---|---|---|---|---|---|
| Type of Impetigo | N | % | N | % | N | % |
| Blistering, Bullous | . | . | 1 | 6.3 | 1 | 3.1 |
| Pure | 2 | 12.5 | . | . | 2 | 6.3 |
| Pure, bullous | 1 | 6.3 | . | . | 1 | 3.1 |
| Pure, Non bullous | . | . | 1 | 6.3 | 1 | 3.1 |
| contagiosa | 1 | 6.3 | 1 | 6.3 | 2 | 6.3 |
| contagiosa, Bullous | 3 | 18.8 | 3 | 18.8 | 6 | 18.8 |
| contagiosa, Non bullous | 9 | 56.3 | 10 | 62.5 | 19 | 59.4 |

8.2. Efficacy

8.2.1 Baseline Severity

Table 3 provides the baseline severity parameters. The mean number of lesions at Baseline was 4.1 and 3.8 in the 1% and 4% minocycline groups respectively, and the respective median numbers of lesions were 4 and 3.5 in the 1% and 4% minocycline groups respectively.

Notably, the severity of the patients in this study was higher than the severity of patients in the studies conducted with Retapamulin ("the majority of patients in both treatment groups presented with only one impetigo lesion"; median=1).[10]

It was further noted that the face was the primary lesion site most common amongst patients. *Staphylococcus aureus* was the most frequently isolated pathogen in the study (56% of isolates in the 1% minocycline group and 75% of isolates from the 4% minocycline group). 34% of the evaluable patients presented isolates of MRSA resistant pathogen.

There was no statistically significant difference between the two groups at baseline with respect to the number and size of lesions, infecting organisms, and the score for exudates, itching, erythema, dryness and burning.

TABLE 3

Primary severity parameters at baseline

| | 1% | 4% | P value (1% vs. 4%) |
|---|---|---|---|
| N | 16 | 16 | |
| Mean No. of lesions (SD) | 4.1 (1.3) | 3.8 (1.5) | 0.619 |
| Median No. of lesions | 4.0 | 3.5 | |
| Total No. of lesions per group | 65 | 61 | |
| Mean lesions area (SD) | 2.73 (1.53) | 3.24 (2.55) | 0.497 |
| Median lesions area | 2.64 | 2.59 | |
| No. of patients with microbiologically confirmed infection | | | |
| *Staphylococcus aureus* | 9 | 12 | 0.264 |
| *Streptococcus pyogenes* | 6 | 7 | 0.719 |
| MRSA | 4 | 7 | 0.264 |
| Other | 4 | 1 | 0.144 |
| Mean exudation score (SD) | 1.78 (1.85) | 1.72 (1.78) | 0.923 |
| Mean itching score (SD) | 3.03 (4.13) | 1.91 (2.19) | 0.346 |
| Mean pain score (SD) | 1.00 (1.33) | 3.41 (3.83) | 0.028 |
| Mean erythema score (SD) | 3.06 (2.14) | 2.38 (3.25) | 0.485 |
| Mean peeling score (SD) | 0.97 (1.28) | 1.09 (2.13) | 0.842 |
| Mean dryness score (SD) | 7.03 (4.21) | 7.19 (4.91) | 0.924 |
| Mean Burning score (SD) | 0.09 (0.27) | 0.25 (0.68) | 0.405 |

8.2.2 Clinical Response

Clinical response was measured in the course of treatment (Day 3±1), at the end of treatment (EOT) (Day 7±1) and 1 week post EOT (Day 14±1) by assessing the number of lesions, their respective sizes and clinical presentations.

The clinical response rates in the PPC population are summarized in Table 4 and FIG. 1. Clinical success was demonstrated in both of the groups among PPC population at Day 3 (visit 2): being 81% and 79% in the 1% and 4% minocycline groups, respectively. The clinical success at EOT (visit 3) was 92.3% and 100% in the 1% and 4% minocycline groups respectively, and at F/U (visit 4), clinical success was 100% in both groups. As demonstrated in Table 4, the change from baseline was statistically significant in both dose groups at Day 3 (visit 2) and subsequently at EOT (visit 3) and and F/U (visit 4). No significant differences in overall efficacy were found between the 1% and 4% groups.

TABLE 4

Clinical Response by visit (PPC population)

| Clinical Response | 1% | | 4% | | All | |
|---|---|---|---|---|---|---|
| | N | % | N | % | N | % |
| Visit 2 (Day 3) | | | | | | |
| Success | 13 | 81.3 | 11 | 78.6 | 24 | 80.0 |
| P-value (Day 3 vs. baseline) | <0.001 | <0.001 | <0.001 | <0.001 | <0.001 | <0.001 |
| Visit 3 | | | | | | |

TABLE 4-continued

Clinical Response by visit (PPC population)

| Clinical Response | 1% N | 1% % | 4% N | 4% % | All N | All % |
|---|---|---|---|---|---|---|
| (EOT) | | | | | | |
| Success | 12 | 92.3 | 11 | 100.0 | 23 | 95.8 |
| P-value (EOT vs. baseline) | <0.001 | <0.001 | <0.001 | <0.001 | <0.001 | <0.001 |
| Visit 4 (F/U) | | | | | | |
| Success | 12 | 100.0 | 8 | 100.0 | 20 | 100.0 |
| P-value (EOT vs. baseline) | <0.001 | <0.001 | <0.001 | <0.001 | <0.001 | <0.001 |

8.2.3 Bacteriological Response

Table 5 summarizes the occurrence of bacterial isolates in the study patients at Baseline (B), EOT and F/U.

The majority of the infections in both groups were caused by S. aureus (21/28, 75%) of which approximately 40% were MRSA, as shown in Table 5. The total number of bacterial isolates at baseline in the 1% minocycline group was 20, which decreased to 3 at EOT, representing 85% bacteriological success. The total number of bacterial isolates at baseline in the 4% minocycline group was 27, which decreased to 7 at EOT, representing 74% bacteriological success. The respective bacteriological success rates at F/U were 85% in the 1% minocycline group and 85% in the 4% minocycline group.

Notably, the bacteriological success rate for MRSA infections in the PPB population was 100% and there was no recurrence observed at F/U.

TABLE 5

The occurrence of bacterial isolates in the study PPB patients at Baseline (B), EOT and F/U - number of patients (%)

| | 1% B | 1% EOT | 1% F/U | 4% B | 4% EOT | 4% F/U |
|---|---|---|---|---|---|---|
| Staphylococcus aureus | 9 (75.0) | 1 (11.1) | 0 (0) | 12 (75.0) | 1 (12.5) | 2 (40.0) |
| Streptococcus pyogenes | 6 (50.0) | 1 (11.1) | 1 (14.3) | 7 (43.8) | 5 (62.5) | 1 (20.0) |
| MRSA | 4 (33.3) | 0 (0) | 0 (0) | 7 (43.8) | 0 (0) | 0 (0) |
| Other | 1 (8.3) | 1 (11.1) | 2 (28.6) | 1 (6.3) | 1 (12.5) | 1 (20.0) |
| Total number of isolates | 20 | 3 | 3 | 27 | 7 | 4 |

8.2.4 Individual Efficacy Parameters a. Cure

A patient was regarded as cured if there was total absence of treated lesions, or if the treated lesions had become dry without crusts. As shown in Table 6, which displays the cure rate of lesions observed in each visit in the PPC population below, 46% of the patients who received the 1% minocycline were cured at EOT (Visit 3) and 58% were cured at F/U (Visit 4).

TABLE 6

Cure of lesions by visit (PPC population)

| Cure of lesions | 1% N | 1% % | 4% N | 4% % | All N | All % |
|---|---|---|---|---|---|---|
| Visit 2 (Day 3) | | | | | | |
| Cure | 0 | 0 | 1 | 7.1 | 1 | 3.3 |
| Visit 3 (EOT) | | | | | | |
| Cure | 6 | 46.2 | 3 | 27.3 | 9 | 37.5 |
| Visit 4 (F/U) | | | | | | |
| Cure | 7 | 58.3 | 4 | 50.0 | 11 | 55.0 | b. Number of Lesions and Lesion Area

Table 7, details the frequency of lesions per patient at baseline, Day 3, EOT and F/U. It is apparent that most of the patients (about 94%) who received the 1% minocycline had three or more lesions at baseline (38% with 3 lesions and 56% with 4 or more lesions). At EOT this number decreased by half (46%) and at F/U only 8% of the patients had more than three lesions.

TABLE 7

Frequency of lesions per patient (PPC population)

| No. of Lesions per patient | Baseline 1% N | Baseline 1% % | Baseline 4% N | Baseline 4% % | Day 3 1% N | Day 3 1% % | Day 3 4% N | Day 3 4% % | EOT 1% N | EOT 1% % | EOT 4% N | EOT 4% % | F/U 1% N | F/U 1% % | F/U 4% N | F/U 4% % |
|---|---|---|---|---|---|---|---|---|---|---|---|---|---|---|---|---|
| 2 | 1 | 6.3 | 4 | 25.0 | 2 | 12.5 | 4 | 28.6 | 2 | 15.4 | 2 | 18.2 | 3 | 25.0 | 1 | 12.5 |
| 3 | 6 | 37.5 | 4 | 25.0 | 5 | 31.3 | 3 | 21.4 | 2 | 15.4 | 2 | 18.2 | 0 | 0 | 1 | 12.5 |
| ≥4 | 9 | 56.3 | 8 | 50.0 | 9 | 56.3 | 6 | 42.9 | 4 | 30.8 | 3 | 27.3 | 1 | 8.3 | 2 | 25.0 |

N = No. of patients with the specified lesions number

Table 8 demonstrates the total number of lesions that disappeared in each group at different time points (at Baseline, Day 3, EOT and F/U) (Size=0). As shown in Table 8 below the total number of lesions that disappeared increased dramatically when the number of lession lesions that disappeared in baseline is compared to EOT and to F/U in both minocycline groups. It is further demonstrated in Table 8 that these changes at EOT and F/U were statistically significant when compared to baseline in both 1% and 4% minocycline groups.

TABLE 8

Total number of lesions at Day 3, EOT and F/U that disappeared (Size = 0) (PPC population)

|  | 1% | | 4% | | All | |
| --- | --- | --- | --- | --- | --- | --- |
|  | N | % | N | % | N | % |
| Baseline | 0 | 0 | 0 | 0 | 0 | 0 |
| Visit 2 - Day 3 | 2 | 3.1 | 6 | 11.3 | 8 | 6.8 |
| P-value (Day 3 vs. baseline) | 0.333 | | 0.082 | | 0.050 | |
| Visit 3 - EOT | 20 | 39.2 | 17 | 38.6 | 37 | 38.9 |
| P-value (EOT vs. baseline) | 0.003 | | 0.018 | | <0.0001 | |
| Visit 4 - F/U | 42 | 79.2 | 22 | 61.1 | 64 | 71.9 |
| P-value (F/U vs. baseline) | <0.0001 | | 0.015 | | <0.0001 | |

N = No. of lesions that disappeared

Figure 2:
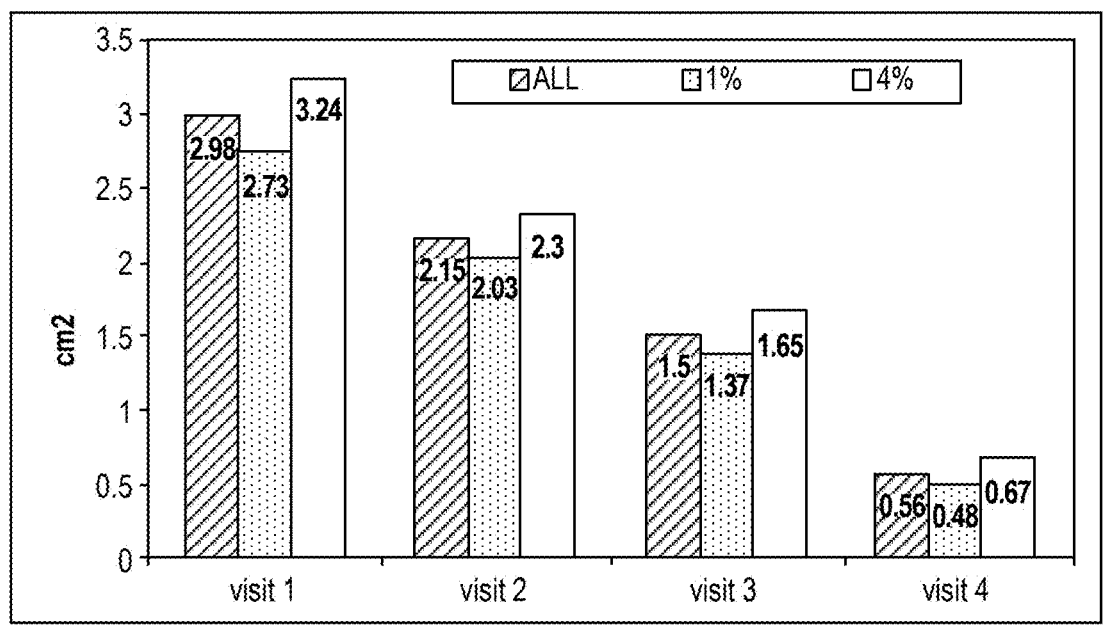
FIG. 2 provides a chart comparing the mean total area of all lesions (per patient) in PPC population by visit.
Figure 3:
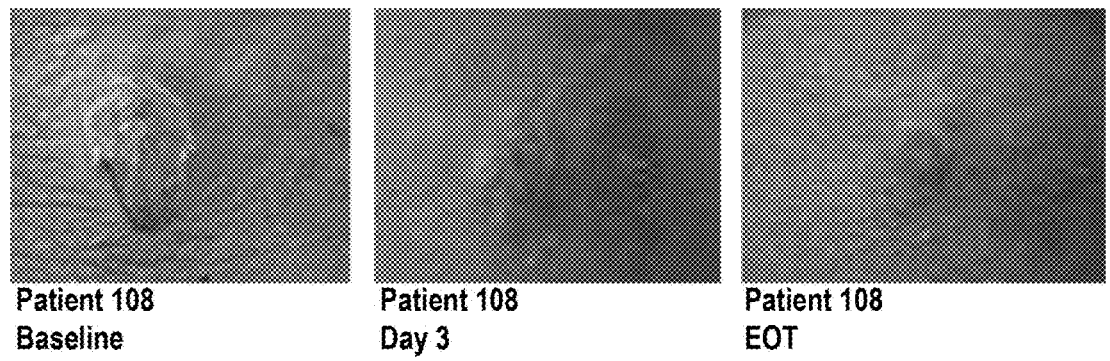
FIG. 3 provides a pictorial example of a *S. aureus* impetigo infection on the upper limb of a 4 year old male observed before and after receiving treatment with minocycline foam 1% at Day 3 and at EOT.
Figure 4:
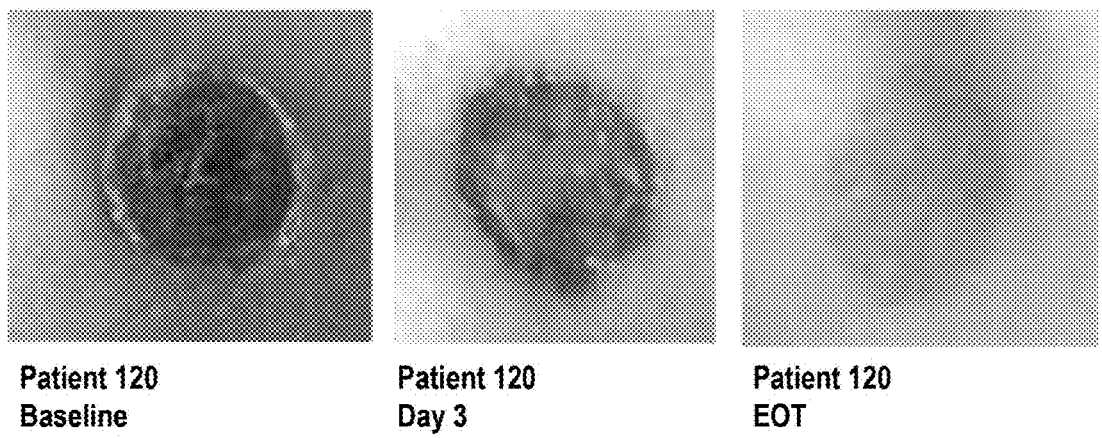
FIG. 4 provides a pictorial example of *S. aureus* impetigo infection on the chest of a 5 year old female observed before and after receiving treatment with minocycline foam 1% at Day 3 and at EOT.
Figure 5:
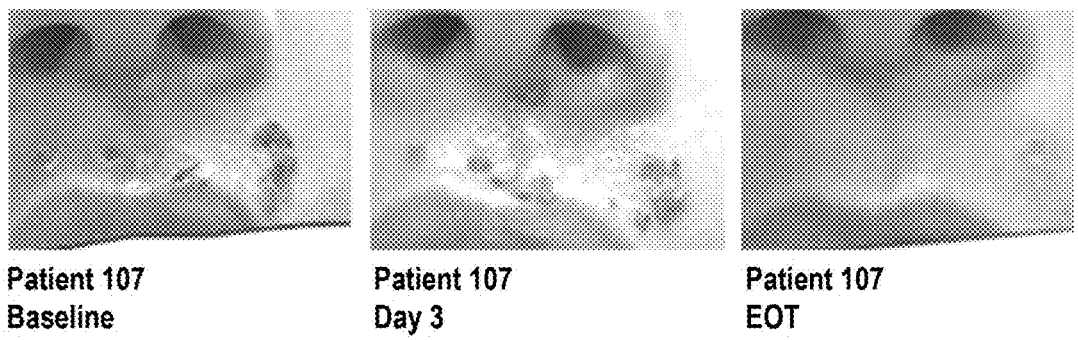
FIG. 5 provides a pictorial example of a *S. pyogenes, S. aureus* and MRSA impetigo infection on the lip of a 3 year old male observed before and after receiving treatment with minocycline foam 4% at Day 3 and at EOT.
Figure 6:
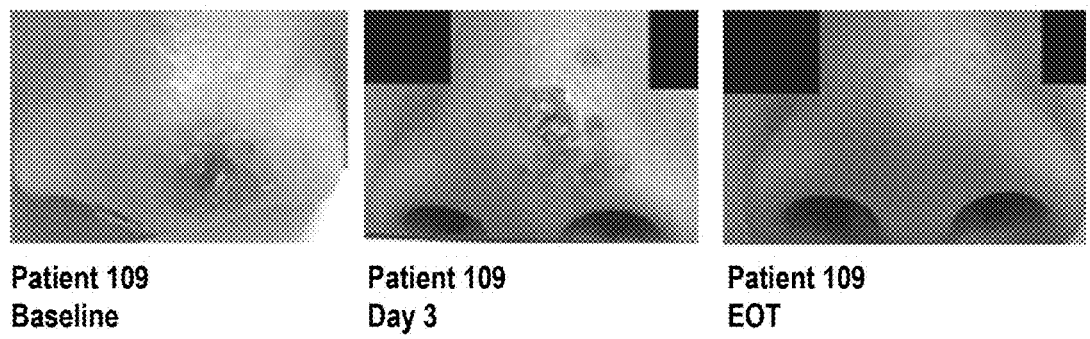
FIG. 6 provides a pictorial example a *S. aureus* and MRSA impetigo infection on the nose of a 6 year old female observed before and after receiving treatment with minocycline foam 4% at Day 3 and at EOT.
Figure 7:
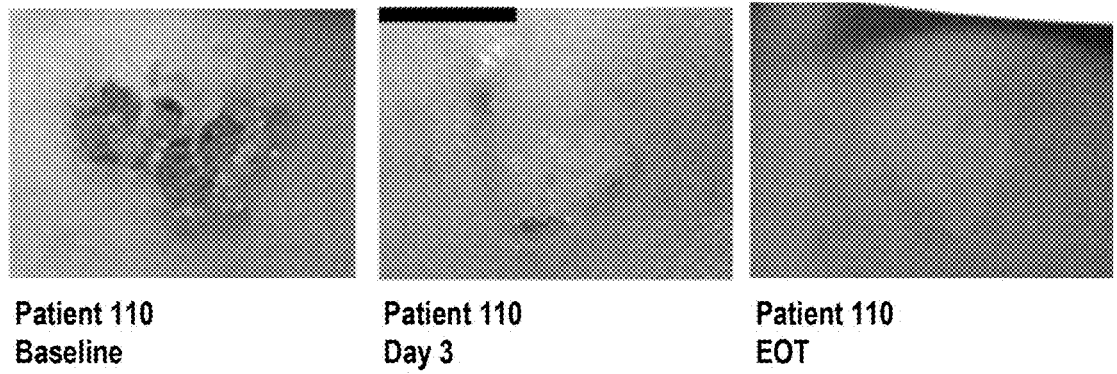
FIG. 7 provides a pictorial example of a *S. aureus* impetigo infection on the face of a 8 year old male observed before and after receiving treatment with minocycline foam 4% at Day 3 and at EOT.
Figure 8:
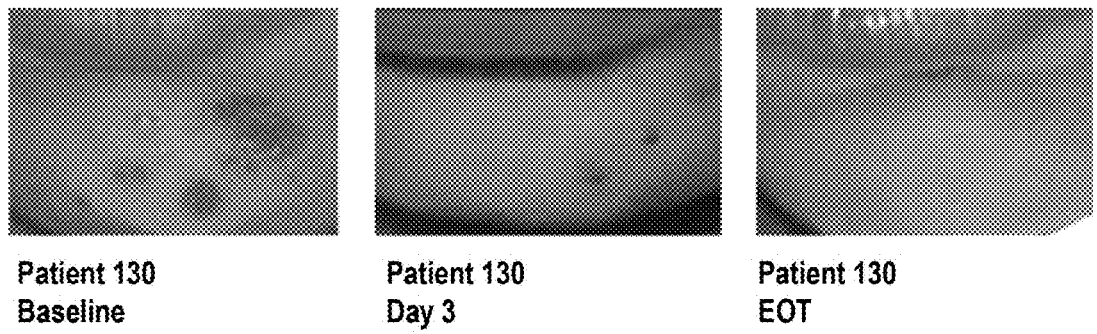
FIG. 8 provides a pictorial example of a *S. pyogenes, S. aureus* and *Acinetobacter* impetigo infection on the chin of of a 4 year old female observed before and after receiving treatment with minocycline foam 4% at Day 3 and at EOT.

FIG. 2 and Table 9 provide the mean total area of lesions per patient at baseline and during the subsequent visits. Table 9 further provides the mean change of area from baseline compared to each visit. As shown in Table 9, at Day 3, 26% and 23% decrease in the lesions area in comparison to baseline lesion area was observed in patients who received the 1% and 4% minocycline groups respectively. As further shown in Table 9, this area decrease was statistically significant. A further decrease in lesion area was observed in patients who received the 1% and 4% minocycline groups, respectively i.e 55% and 47% (at EOT) in the 1% and 4% dosage groups, respectively and 86% and 59% at F/U in the 1% and 4% minocycline groups respectively. FIG. 2 depicts the mean total area of all lesions (per patient) in PPC population as demonstrated in Table 9.

TABLE 9

Decrease of total area of all lesions (per patient) (PPC population)

|  | 1% | | | 4% | | | All | | |
| --- | --- | --- | --- | --- | --- | --- | --- | --- | --- |
|  | N | Mean | P* | N | Mean | P* | N | Mean | P* |
| Mean area (cm$^2$) | | | | | | | | | |
| Baseline | 16 | 2.73 cm$^2$ | | 16 | 3.24 cm$^2$ | | 32 | 2.98 cm$^2$ | |
| Visit 2 | 16 | 2.03 cm$^2$ | | 14 | 2.30 cm$^2$ | | 30 | 2.15 cm$^2$ | |
| Visit 3 | 13 | 1.37 cm$^2$ | | 11 | 1.65 cm$^2$ | | 24 | 1.50 cm$^2$ | |
| Visit 4 | 12 | 0.48 cm$^2$ | | 8 | 0.67 cm$^2$ | | 20 | 0.56 cm$^2$ | |
| Decrease of lesion area per patient (cm$^2$)$^2$ | | | | | | | | | |
| Visit 2 | 16 | −0.70 cm$^2$ | 0.012 | 14 | −0.73 cm$^2$ | 0.002 | 30 | −0.71 cm$^2$ | <.001 |
| Visit 3 | 13 | −1.51 cm$^2$ | <.001 | 11 | −1.51 cm$^2$ | <.001 | 24 | −1.51 cm$^2$ | <.001 |
| Visit 4 | 12 | −2.34 cm$^2$ | <.001 | 8 | −1.92 cm$^2$ | 0.002 | 20 | −2.17 cm$^2$ | <.001 |
| Decrease of lesion area per patient (%)$^3$ | | | | | | | | | |
| Visit 2 | 16 | −26% | | 14 | −23% | | 30 | | |
| Visit 3 | 13 | −55% | | 11 | −47% | | 24 | | |
| Visit 4 | 12 | −86% | | 8 | −59% | | 20 | | |

*P-value for changes vs. Baseline (paired t-test)
$^2$As the number of patients is not the same between visit 2, visit 3 and visit 4 this was taken into consideration in the calculation of the decrease by the satistician.
$^3$These numbers are different than 61/611,232 because they are calculated by dividing the revised decrease in area by the baseline area c. Exudate, Itch, Pain and Erythema As shown in Tables 10a, 10b and 10c, patients were evaluated for seven signs and symptoms further pertaining to efficacy of treatment: erythema, dryness, exudation, peeling, burning, itching and pain on a scale of 0-3: 0=absent, 1=mild, 2=moderate, 3=severe. Exudation (the primary sign of active infection), burning, itching and pain are most relevant to the severity of impetigo. The decrease in the exudation scores upon comparison of baseline to day 3 in both the 1% and 4% minocycline groups was clinically and statistically significant. The exudation score further decreased at EOT and F/U.

At EOT and F/U in the 1% minocycline group the decrease in the severity signs and symptoms such as erythema, dryness, exudation, itching and pain were statistically significant as well.

TABLE 10a

Change of severity signs and symptoms from Day 3 to Baseline (PPC population)

|  | 1% | | | 4% | | | All | | |
| --- | --- | --- | --- | --- | --- | --- | --- | --- | --- |
|  | N | Mean | P | N | Mean | P | N | Mean | P |
| Erythema | 16 | −0.75 | 0.260 | 14 | −1.11 | 0.259 | 30 | −0.92 | 0.104 |
| Dryness | 16 | 0.16 | 0.865 | 14 | −0.64 | 0.621 | 30 | −0.22 | 0.776 |
| Exudation | 16 | −0.72 | 0.008 | 14 | −1.36 | 0.018 | 30 | −1.02 | <.001 |
| Peeling | 16 | 0.59 | 0.182 | 14 | 1.07 | 0.041 | 30 | 0.82 | 0.014 |
| Burning | 16 | 0.16 | 0.474 | 14 | −0.14 | 0.336 | 30 | 0.02 | 0.901 |
| Itching | 16 | −0.91 | 0.081 | 14 | −0.25 | 0.780 | 30 | −0.60 | 0.220 |
| Pain | 16 | −0.63 | 0.190 | 14 | −3.00 | 0.008 | 30 | −1.73 | 0.004 |

TABLE 10b

Change of Efficacy Presentation from
Visit 3 to Baseline (PPC population)

|  | 1% | | | 4% | | | All | | |
| --- | --- | --- | --- | --- | --- | --- | --- | --- | --- |
|  | N | Mean | P | N | Mean | P | N | Mean | P |
| Erythema | 13 | −1.54 | 0.020 | 11 | −0.68 | 0.656 | 24 | −1.15 | 0.133 |
| Dryness | 13 | −3.54 | 0.042 | 11 | −3.77 | 0.027 | 24 | −3.65 | 0.002 |
| Exudation | 13 | −1.00 | 0.001 | 11 | −1.32 | 0.033 | 24 | −1.15 | <.001 |
| Peeling | 13 | −0.62 | 0.059 | 11 | 0.68 | 0.218 | 24 | −0.02 | 0.947 |
| Burning | 13 | −0.12 | 0.190 | 11 | 0.00 | — | 24 | −0.06 | 0.185 |
| Itching | 13 | −2.62 | 0.017 | 11 | −0.77 | 0.595 | 24 | −1.77 | 0.043 |
| Pain | 13 | −0.88 | 0.012 | 11 | −3.18 | 0.028 | 24 | −1.94 | 0.005 |

TABLE 10c

Change of Efficacy Presentation from
Visit 4 to Baseline (PPC population)

|  | 1% | | | 4% | | | All | | |
| --- | --- | --- | --- | --- | --- | --- | --- | --- | --- |
|  | N | Mean | P | N | Mean | P | N | Mean | P |
| Erythema | 12 | −2.08 | 0.005 | 8 | −1.00 | 0.05 | 20 | −1.65 | <.001 |
| Dryness | 12 | −5.00 | 0.001 | 8 | −3.75 | 0..079 | 20 | −4.50 | <.001 |
| Exudation | 12 | −0.83 | 0.023 | 8 | −1.63 | 0.017 | 20 | −1.15 | <.001 |
| Peeling | 12 | −0.46 | 0.283 | 8 | 0.63 | 0.299 | 20 | −0.03 | 0.943 |
| Burning | 12 | 0.13 | 0.660 | 8 | 0.00 | — | 20 | 0.08 | 0.651 |
| Itching | 12 | −3.17 | 0.010 | 8 | −0.13 | 0.913 | 20 | −1.95 | 0.027 |
| Pain | 12 | −1.00 | 0.012 | 8 | −3.81 | 0.044 | 20 | −2.13 | 0.007 | d. Photographic Examples of Successful Treatment of Impetigo Lesions

The following pictorial examples show the baseline, Day 3 and EOT status for the Minocycline 1% (FIGS. 3 and 4), and 4% (FIGS. 5-8) topical foams. In these pictorial examples, the improvement is apparent as is also the restoration of visible, normal cutaneous topographic features, indicating the return of skin integrity.

8.3 Safety and Tolerability

Safety was determined for all randomized patients by interview at each visit. All adverse experiences were determined by the investigator to be not related; possibly related; or related to the study drug.

No clinical recurrences and no adverse events were observed in any of the groups. Minocycline topical foam administered twice daily was well-tolerated, with high rates of clinical and microbiological responses for treating impetigo.

8.4 Satisfaction Questionnaires

Satisfaction questionnaires, answered by the patient's parents at EOT, revealed high satisfaction with treatment, as exemplified in Table 11. In the General Satisfaction category a majority of caregivers (more than 55%) in both groups rated the product as "very satisfactory" or "excellent" and a further 33% and 44% in the 1% and 4% minocycline groups respectively rated it as "moderately satisfactory" raising the general level of satisfaction to over 90%. Likewise, in the Usability category 71% of the caregivers in all groups rated the product as "very satisfactory" or "excellent" and a further 24% in all groups rated it as "moderately satisfactory" raising the general level of usability to over 90%. None of the caregivers rated the product as "unsatisfactory".

TABLE 11.1

Patient Satisfaction Questionnaire

| Patient Satisfaction Questionnaire | 1% | | | | | 4% | | | | | All | | | | | |
| --- | --- | --- | --- | --- | --- | --- | --- | --- | --- | --- | --- | --- | --- | --- | --- | --- |
|  | N | Mean | Std | Median | Min | Max | N | Mean | Std | Median | Min | Max | N | Mean | Std | Median | Min | Max |
| Drug Spreading (1: not at all, 5: excellent) | 12 | 3.7 | 0.9 | 3.0 | 3.0 | 5.0 | 9 | 3.7 | 1.0 | 4.0 | 2.0 | 5.0 | 21 | 3.7 | 0.9 | 3.0 | 2.0 | 5.0 |
| Drug homogeneity (1: not at all easy, 5: excellent) | 10 | 3.6 | 1.0 | 3.5 | 2.0 | 5.0 | 9 | 4.1 | 0.8 | 4.0 | 3.0 | 5.0 | 19 | 3.8 | 0.9 | 4.0 | 2.0 | 5.0 |
| Drug absorption (1: not at all absorbed, 4: very good) | 12 | 3.0 | 0.6 | 3.0 | 2.0 | 4.0 | 8 | 3.4 | 0.5 | 3.0 | 3.0 | 4.0 | 20 | 3.2 | 0.6 | 3.0 | 2.0 | 4.0 |
| Greasy (1: very greasy, 6: not at all) | 12 | 4.6 | 1.0 | 5.0 | 2.0 | 6.0 | 9 | 4.1 | 1.2 | 5.0 | 2.0 | 5.0 | 21 | 4.4 | 1.1 | 5.0 | 2.0 | 6.0 |
| Shiny Skin (1: very shiny, 6: not at all) | 12 | 4.2 | 1.2 | 4.0 | 2.0 | 6.0 | 8 | 3.8 | 1.2 | 4.0 | 2.0 | 6.0 | 20 | 4.0 | 1.2 | 4.0 | 2.0 | 6.0 |
| Sticky Skin (1: very sticky, 6: not at all) | 12 | 4.6 | 1.0 | 5.0 | 3.0 | 6.0 | 9 | 4.4 | 1.0 | 5.0 | 3.0 | 6.0 | 21 | 4.5 | 1.0 | 5.0 | 3.0 | 6.0 |
| Moisted Skin (1: not at all, 5: excellent) | 12 | 2.8 | 0.6 | 3.0 | 2.0 | 4.0 | 9 | 3.0 | 1.5 | 3.0 | 1.0 | 5.0 | 21 | 2.9 | 1.1 | 3.0 | 1.0 | 5.0 |
| General Feeling (1: not at all good, 5: excellent) | 12 | 3.3 | 0.8 | 3.0 | 2.0 | 5.0 | 9 | 3.6 | 1.1 | 4.0 | 2.0 | 5.0 | 21 | 3.4 | 0.9 | 3.0 | 2.0 | 5.0 |
| Odor (1: not at all good, 6: no smell) | 12 | 4.1 | 1.3 | 3.5 | 3.0 | 6.0 | 9 | 4.0 | 1.7 | 4.0 | 1.0 | 6.0 | 21 | 4.0 | 1.5 | 4.0 | 1.0 | 6.0 |
| Use the Pump (1: not at all easy, 5: excellent) | 12 | 3.1 | 0.5 | 3.0 | 2.0 | 4.0 | 9 | 3.9 | 1.1 | 4.0 | 2.0 | 5.0 | 21 | 3.4 | 0.9 | 3.0 | 2.0 | 5.0 |
| Control the amount (1: not at all easy, 5: excellent) | 12 | 3.3 | 0.9 | 3.0 | 1.0 | 4.0 | 9 | 3.1 | 1.5 | 3.0 | 1.0 | 5.0 | 21 | 3.2 | 1.1 | 3.0 | 1.0 | 5.0 |

TABLE 11.1-continued

Patient Satisfaction Questionnaire

| Patient Satisfaction Questionnaire | 1% | | | | | | 4% | | | | | | All | | | | | |
|---|---|---|---|---|---|---|---|---|---|---|---|---|---|---|---|---|---|---|
| | N | Mean | Std | Median | Min | Max | N | Mean | Std | Median | Min | Max | N | Mean | Std | Median | Min | Max |
| Instructions for use (1: not at all clear, 5: excellent) | 12 | 3.6 | 0.7 | 3.5 | 3.0 | 5.0 | 9 | 3.8 | 0.8 | 4.0 | 3.0 | 5.0 | 21 | 3.7 | 0.7 | 4.0 | 3.0 | 5.0 |
| General Satisfaction (1: not at all, 5: excellent) | 12 | 3.8 | 1.0 | 4.0 | 2.0 | 5.0 | 9 | 3.8 | 0.8 | 4.0 | 3.0 | 5.0 | 21 | 3.8 | 0.9 | 4.0 | 2.0 | 5.0 |
| General Satisfaction of the Foam (1: not easy for use, 2: no results, 3: satisfy, 4: very satisfy, 5: excellent) | 12 | 3.9 | 0.5 | 4.0 | 3.0 | 5.0 | 9 | 3.7 | 1.0 | 4.0 | 2.0 | 5.0 | 21 | 3.8 | 0.7 | 4.0 | 2.0 | 5.0 |
| Recommendation (1: definitely yes, 5: definitely not) | 12 | 2.3 | 1.5 | 2.0 | 1.0 | 5.0 | 9 | 1.7 | 0.9 | 1.0 | 1.0 | 3.0 | 21 | 2.0 | 1.3 | 2.0 | 1.0 | 5.0 |

TABLE 11.2

General satisfaction and usability rating, as opined by patients' caregivers at EOT.

| | General satisfaction | | | | | | Usability | | | | | |
|---|---|---|---|---|---|---|---|---|---|---|---|---|
| | 1% | | 4% | | All | | 1% | | 4% | | All | |
| | N | % | N | % | N | % | N | % | N | % | N | % |
| 5 (Excellent) | 4 | 33.3% | 2 | 22.2% | 6 | 28.6% | 1 | 8.3% | 2 | 22.2% | 3 | 14.3% |
| 4 (Very satisfactory) | 3 | 25% | 3 | 33.3% | 6 | 28.6% | 9 | 75% | 3 | 33.3% | 12 | 57.1% |
| 3 (Moderate) | 4 | 33.3% | 4 | 44.4% | 8 | 38.1% | 2 | 16.7% | 3 | 33.3% | 5 | 23.8% |
| 2 (Slight) | 1 | 8.3% | 0 | 0% | 1 | 4.7% | 0 | 0% | 1 | 11.1% | 1 | 4.8% |
| 1 (Unsatisfactory) | 0 | 0% | 0 | 0% | 0 | 0% | 0 | 0% | 0 | 0% | 0 | 0% |

8.5 Discussion

This is the first clinical study to evaluate the safety and efficacy of topical minocycline in treating impetigo. It has been shown that topical minocycline foam is a highly effective and convenient new treatment option for impetigo, with early clinical response being observed on the first visit after 3 days of treatment:

- About 80% clinical success was observed after 3 days of treatment in both groups (Table 4).
- 100% clinical success was observed on Day 7 in 4% minocycline group and on Day 14 in the 1% minocycline group.
- All MRSA infections appeared eradicated at EOT and F/U in both dose groups (Table 5).
- No drug-related side effects were recorded.

These impressive effects were achieved following twice daily topical application of minocyline foam for seven days. In contrast, the currently available topical antibiotics Fucidin (fucidic acid, LEO Pharma) and Bactroban (mupirocin, GSK) require three daily treatments. Comparison of the current study protocol with the studies carried out of Altabax (retapamulin, GSK) shows that the severity of impetigo in the current minocycline foam study was higher than the respective severity in the Altabax studies—with the median numbers of lesions at Baseline (3.5-4 per patient) being significantly higher than the reported baseline numbers in the retapamulin studies ("the majority of patients in both treatment groups in the retapamulin studies presented with only one impetigo lesion"; median=1).

Emerging resistance to mupirocin is a concern not only because it compromises its effectiveness for the treatment of impetigo, but it also compromises the utility of mupirocin for other more serious gram-positive infections. Mupirocin resistance rates range from 1.3% in Latin America to 8.7% in Europe in S. aureus isolates.[4] In coagulase-negative staphylococci isolates, mupirocin resistance rates are higher, ranging from 12.7% in Europe to 38.8% in the United States

[4] Jones R N, Fritsche T R, Sader H S, Ross J E. Activity of retapamulin (SB-275833), a novel pleuromutilin, against selected resistant gram-positive cocci. Antimicrob Agents Chemother. 2006; 50:2583-6.

The effective eradication of MRSA is encouraging and gives rise to a cure, as well as protecting the surrounding infants and children from contracting resistant bacterial infections.

The study population comprised pediatric patients, aged 2-15 years old and yet, the drug was well tolerated and positively rated for its effect and usability by the patients and their caregivers. Not only was it well-tolerated (i.e. did not cause local adverse systemic effects), but it also lead to the rapid reduction of pain and symptoms such exudate and itching, which help minimize the risk for infecting playmates and siblings.)

Thus, topical minocycline foam offers a safe and effective alternative to fucidic acid, mupirocin and retapamulin for the topical treatment of impetigo in children. The ease of use, with twice daily dosing, as well as its broad spectrum of activity, quick onset of clinical effect and the lack of adverse effects, make it an attractive choice. Some initial studies with a single dose each day for seven days indicate that a single daily regime may also be effective. These results warrant additional clinical studies in order to establish the role and best mode of application topical minocycline foam in clinical practice. Further the results can be extrapolated for use with gel and liquid gel delivery formats.

9. Compositions

The below compositions, used in the clinical study, were prepared according to the manufacturing procedures detailed in Example 1.

| Ingredients | Formulations | |
|---|---|---|
| | 244B (1% Minocycline) % w/w | 244A (4% Minocycline) % w/w |
| Light Mineral oil | 4.44 | 1.11 |
| Cyclomethicone | 5.00 | 5.00 |
| Coconut oil | 23.60 | 23.60 |
| Soybean oil | 50.00 | 50.00 |
| Hydrogenated castor oil | 2.00 | 2.00 |
| Beeswax | 2.00 | 2.00 |
| Myristyl alcohol | 2.50 | 2.50 |
| Cetostearyl alcohol | 3.50 | 3.50 |
| Stearyl alcohol | 1.50 | 1.50 |
| Behenyl alcohol | 1.10 | 1.10 |
| Fumed Silica (SiO2) | 0.25 | 0.25 |
| Stearic acid | 3.00 | 3.00 |
| Minocycline HCl (90% potency) | 1.11 | 4.44 |
| Total | 100 | 100 |
| Propellant AP-70 | 12.00 | 12.00 |

All inactive ingredients used in the formulation are intended for topical use and listed in the current FDA Inactive Ingredient Database; concentrations used do not exceed the maximum concentrations given in Database.

Specifications

The 244 A and B product undergoes release in accordance to the physical and chemical specifications, as listed in Table 12.

TABLE 12

Test parameters and Specifications at Release for 244 A and B

| Test Parameter | Specification |
|---|---|
| Assay (% w/w): | |
| Minocycline HCl | 90-120% |
| 4-epi-Minocycline | NMT 6% |
| Appearance: | |
| quality | Good (G) to excellent (E) |
| odor | No odor or a very faint odor |
| color | Yellow, pale yellow |
| Microscopic examination of samples for the presence of crystals | Solely Minocycline crystals |
| Foam density (g/mL) | 0.01-0.30 |
| Shakability | Shakable |
| Collapse time at 36° C. (sec) | >30 |

Stability

The achievement of a long term stable foamable formulation of tetracycline antibiotics described herein, was a major challenge and required both extensive research and creativity.

Figure 9:
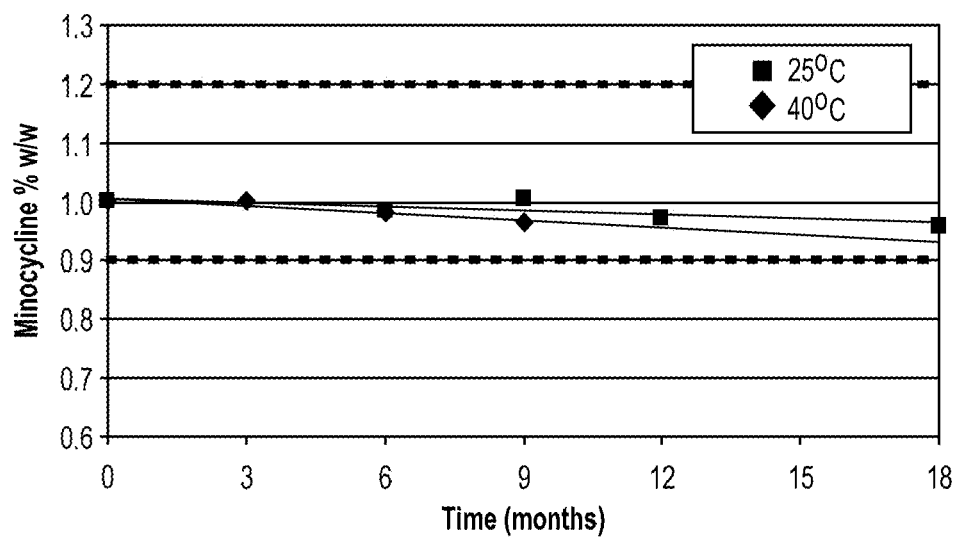
FIG. 9 provides a chart comparing the chemical stability of minocycline foam 1% at 25° C. and 40° C. during a period of 18 months.
Figure 10:
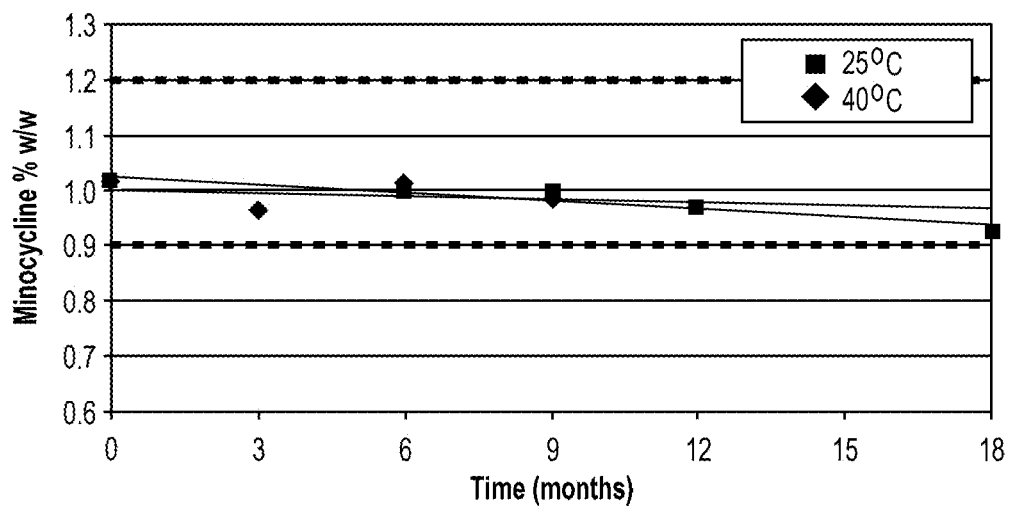
FIG. 10 provides a chart comparing the chemical stability of minocycline foam 4% at 25° C. and 40° C. during a period of 18 months.
Figure 11:
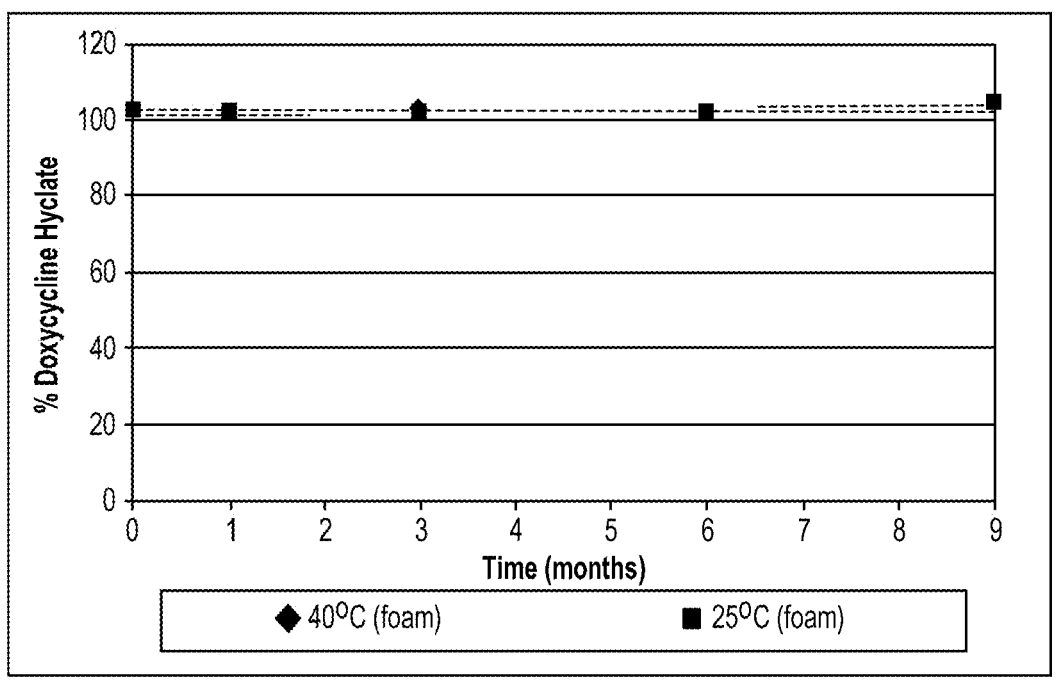
FIG. 11 provides a chart comparing the chemical stability of doxycycline foam 1% at 25° C. and 40° C. during a period of 9 months.

The following examples illustrates the chemical stability of minocycline HCl ("MCH") and doxycycline hyclate in oleaginous formulations, MCH244 and DOX244 as described in Tables 13-17 and FIGS. 9-11 below. In an accelerated stability study, samples were stored at 40° C., and the concentrations of minocycline HCl and doxycycline hyclate were determined by UPLC. The stability test results following 2 months, 3 months, 6 months, 9 months, 12 months, 18 months of storage are shown herein below.

Samples of 244 1% and 4% were stored at 25° C. and 40° C. in order to test physical and chemical stability.

1. Inspection of Formulation in Glass Bottles

The use of pressurized glass bottles enables the inspection of formulations for homogeneity in the presence of propellant. Following 18 months of storage at 25° C. the formulation was found to be re-dispersible, i.e., homogeneous following slight shaking.

2. Stability Following Storage at 25° C. and 40° C.

Storage at 25° C. and 40° C. for 18 months revealed almost no change in the Minocycline concentration.

Test results for chemical stability of minocycline following storage for up to 18 months at 25° C. and 40° C. are summarized in Table 13-14 and Tables 11-12. There was practically no degradation of 244 1% and 4% minocycline following 18 months at 25° C. and also following 9 months at 40° C. These stability results indicate shelf life of more than two years at ambient temperature. Test results for chemical stability of doxycycline following storage for up to 9 months at 25° C. and 40° C. are summarized in Table 15-17. There was practically no degradation of doxycycline following 6 months at 25° C. and at 40° C. These stability results likewise indicate a long shelf life of more than two years at ambient temperature. In one or more embodiments the tetracycline composition has a shelf life of at least 6 months, or at least 9 months, or at least 12 months or at least 15 months, or at least 18 months or at least 21 months or at least 24 months at ambient temperature. In one or more embodiments the tetracycline composition has a shelf life of at least 6 months, or at least 9 months, or at least 12 months or at least 15 months, or at least 18 months or at least 21 months or at least 24 months at 25° C. In one or more embodiments the tetracycline composition has a shelf life of at least 1 month, or at least 3 months, or at least 3 months or at least 6 months, or at least 9 months or at least 12 months 40° C.

TABLE 13

Minocycline content in 244 1% following storage for 18 months at 25° C. and 40° C.

| | Minocycline content (% w/w) | | | | | |
|---|---|---|---|---|---|---|
| Temp | T = 0 | 3 M | 6 M | 9 M | 12 M | 18 M |
| 25° C. | 1.001 | NM | 0.986 | 1.007 | 0.972 | 0.959 |
| 40° C. | 1.001 | 1.002 | 0.983 | 0.965 | NM | NM |

(NM = not measured)

TABLE 14

Minocycline content in FXFM244 4% following storage for 18 months at 25° C. and 40° C. (Lot MCH-244-100825)

| | Minocycline content (% w/w) | | | | | |
|---|---|---|---|---|---|---|
| Temp | T = 0 | 3 M | 6 M | 9 M | 12 M | 18 M |
| 25° C. | 1.012 | NM | 0.998 | 0.998 | 0.972 | 0.925 |
| 40° C. | 1.012 | 0.963 | 1.009 | 0.978 | NM | NM |

Minocycline Physical Stability:

The results for physical stability following storage at 25° C. and 40° C. for 18 months were as follows:

Foam quality: Conformed to the foam quality specification following 9 months storage at 40° C.

Odor: Conformed to the specification and showed no odor following storage at 40° C. for 9 months.

Color: The color of the formulation remained light slightly changed to grey yellow following storage at 40° C. for 9 months. No change was observed at 25° C.

Shakability: Conformed to specifications following storage at 40° C. for 9 months.

Density: No significant change in density was found after storage at 40° C. for 9 months.

| DOX-244-111123 | |
|---|---|
| Ingredient Name | % W/W |
| Coconut oil | 23.60 |
| Mineral oil light | 4.35 |
| Soybean oil | 50.00 |
| Stearic acid | 3.00 |
| Behenyl alcohol | 1.10 |
| Hydrogenated castor oil | 2.00 |
| Beeswax | 2.00 |
| Stearyl alcohol | 1.50 |
| Cetostearyl alcohol | 3.50 |
| Myristyl alcohol | 2.50 |
| Cyclomethicone | 5.00 |
| Silicon dioxide | 0.25 |
| Doxycycline Hyclate | 1.20 |

TABLE 15

Doxycycline % content in DOX-244-111123 PF following storage for 9 months at 5° C. 25° C. 40° C. and 50° C.

| | | Doxycycline content (% w/w) | | | | | | | | |
|---|---|---|---|---|---|---|---|---|---|---|
| | | 1 M | | | 2 M | | 3 M | | 6 M | 9 M |
| Batch/Sample name | T = 0 | 5° C. | 25° C. | 50° C. | 25° C. | 50° C. | 25° C. | 40° C. | 25° C. | 40° C. | 25° C. |
| DOX-244-111123 PF | 1.0220 | 1.031 | 1.022 | NM | NM | NM | 1.010 | 1.031 | 1.017 | 1.025 | 1.053 |
| DOX-244-111123 PFF | 1.0800 | 1.098 | 1.080 | 1.060 | NM | 1.045 | 1.082 | 1.046 | 1.046 | 1.028 | 1.091 |

Collapse time: No change in foam collapse time (the time for the foam to reach half of its initial height) was found in any of the formulation samples tested after storage for 9 months at 40° C.

Microscopic observations: No significant change in the microscopic appearance was noted following storage at 40° C. for 9 months.

Corrosion and deterioration: The coated aluminum surfaces of the can and valve and the plastic housing of the valve appeared fully intact and showed no signs of corrosion or deterioration. No changes in color or deformation were observed.

Doxycycline Physical Stability:

The results for physical stability following storage at 25° C. for 9 months and 40° C. for 6 months were as follows:

Foam quality: At least good quality.

Odor: Showed no or very faint odor.

Collapse time: At least 100 seconds.

Production GMP Compliance

For the purpose of clinical supplies, the production the compositions were performed according to the principles of current good manufacturing practice (c-GMP). Production conditions were aimed to ensure high quality of the product and to prevent any potential cross contamination. The production site was certified by the Israel Ministry of Health as suitable for GMP production and supply of small clinical batches for Phase I and II clinical trials.

TABLE 16

Stability of Doxycyline Foam at 25° C. and 40° C.
%[5] Doxycycline in DOX244 foam product

| Months | 40° C. (foam) | 25° C. (foam) |
|---|---|---|
| 0 | 102.2 | 102.2 |
| 1 | | 102.2 |
| 2 | | |
| 3 | 103.1 | 101.0 |
| 6 | 102.5 | 101.7 |
| 9 | | 105.3 |

TABLE 17

Degradation of Doxycycline at 5° C. 25° C. 40° C. and 50° C.
Degradation product w/w

| | Batch/Sample name | DOX-244-111123 PF | DOX-244-111123 PFF |
|---|---|---|---|
| T0 | RRT 0.75 | 0.003 | 0.004 |
| | RRT 0.85 | 0.010 | 0.011 |
| 1 M | 5° C. RRT 0.75 | 0.003 | 0.003 |
| | 5° C. RRT 0.85 | 0.010 | 0.010 |
| | 25° C. RRT 0.75 | 0.003 | 0.003 |
| | 25° C. RRT 0.85 | 0.010 | 0.010 |
| | 50° C. RRT 0.75 | NM | 0.003 |
| | 50° C. RRT 0.85 | NM | 0.01 |
| 2 M | 50° C. RRT 0.75 | NM | 0.003 |
| | 50° C. RRT 0.85 | NM | 0.009 |
| 3 M | 25° C. RRT 0.75 | 0.003 | 0.004 |
| | 25° C. RRT 0.85 | 0.01 | 0.011 |
| | 40° C. RRT 0.75 | 0.003 | 0.003 |
| | 40° C. RRT 0.85 | 0.01 | 0.01 |
| 6 M | 25° C. RRT 0.75 | 0.003 | 0.003 |
| | 25° C. RRT 0.85 | 0.01 | 0.01 |
| | 40° C. RRT 0.75 | 0.003 | 0.003 |
| | 40° C. RRT 0.85 | 0.01 | 0.01 |
| 9 M | 25° C. RRT 0.75 | 0.003 | 0.003 |
| | 25° C. RRT 0.85 | 0.009 | 0.01 |

What is claimed is:

1. A method for healing of an infected acne lesion without scarring, comprising topically administering at least once daily an effective amount of a minocycline antibiotic foam to an infected acne lesion, wherein the minocycline antibiotic foam is produced from a foamable composition upon addition of a liquefied or compressed gas propellant, the foamable composition comprising:
   (a) 60% to 90% by weight of one or more hydrophobic oils selected from the group consisting of a mineral oil, a soybean oil, a coconut oil, cyclomethicone, and a mixture of two or more thereof;
   (b) a wax selected from the group consisting of a beeswax, a hydrogenated castor oil, and a mixture thereof;
   (c) at least one solid fatty alcohol having a carbon chain length of 14 to 22 carbons;
   (d) at least one solid fatty acid having a carbon chain length of 12 to 28 carbons; and
   (e) 0.2% to 10% by weight of a minocycline; and
wherein the foamable composition does not comprise a surfactant.

2. The method of claim 1, wherein the minocycline is present in a free base form, a salt form, a hydrate form, or a complex form.

3. The method of claim 1, wherein the minocycline is 1 to 4% by weight of the foamable composition.

4. The method of claim 1, wherein the at least one solid fatty alcohol is selected from the group consisting of myristyl alcohol, cetostearyl alcohol, stearyl alcohol, behenyl alcohol, and a mixture of two or more thereof.

5. The method of claim 1, wherein the least one solid fatty acid having a carbon chain length of 12 to 28 carbons comprises stearic acid.

6. The method of claim 1, wherein the foamable composition further comprises fumed silica.

7. The method of claim 1, wherein the minocycline is micronized.

8. The method of claim 1, wherein the foamable composition further comprises an additional active agent.

* * * * *